(12) United States Patent
Lavie et al.

(10) Patent No.: US 8,349,318 B2
(45) Date of Patent: Jan. 8, 2013

(54) USE OF SPECIFICALLY ENGINEERED ENZYMES TO ENHANCE THE EFFICACY OF PRODRUGS

(75) Inventors: Arnon Lavie, Chicago, IL (US); Manfred Konrad, Göttingen (DE)

(73) Assignee: The Board of Trustees of the University of Illinois, Urbana, IL (US)

( * ) Notice: Subject to any disclaimer, the term of this patent is extended or adjusted under 35 U.S.C. 154(b) by 149 days.

(21) Appl. No.: 12/993,660

(22) PCT Filed: May 18, 2009

(86) PCT No.: PCT/US2009/044318
§ 371 (c)(1),
(2), (4) Date: Feb. 10, 2011

(87) PCT Pub. No.: WO2009/143048
PCT Pub. Date: Nov. 26, 2009

(65) Prior Publication Data
US 2011/0129470 A1    Jun. 2, 2011

Related U.S. Application Data

(60) Provisional application No. 61/054,403, filed on May 19, 2008, provisional application No. 61/054,400, filed on May 19, 2008.

(51) Int. Cl.
*A61K 38/54* (2006.01)
*A61K 39/00* (2006.01)
*G01N 33/53* (2006.01)
*C12P 21/06* (2006.01)
*C12N 9/96* (2006.01)
*C07H 21/04* (2006.01)

(52) U.S. Cl. ............... 424/94.3; 424/178.1; 435/7.1; 435/69.1; 435/188; 435/320.1; 530/367.1; 536/23.1

(58) Field of Classification Search ............... 435/69.1, 435/188; 424/178.1, 94.3; 425/7.1; 536/23.1; 530/387.1
See application file for complete search history.

(56) References Cited

U.S. PATENT DOCUMENTS

| 5,914,258 | A | 6/1999 | Wei et al. |
| 6,299,876 | B1 | 10/2001 | Bagshawe |
| 7,419,811 | B2 | 9/2008 | Lavie et al. |
| 2001/0012835 | A1 | 8/2001 | Fine et al. |
| 2007/0037269 | A1 | 2/2007 | Marliere et al. |
| 2007/0258968 | A1 | 11/2007 | Lavie et al. |

FOREIGN PATENT DOCUMENTS

| FR | 2823219 | 10/2002 |
| WO | WO 01/88106 | 11/2001 |
| WO | WO 02/083892 | 10/2002 |

OTHER PUBLICATIONS

Brekke, et al., 2003, Nat. Rev. Drug Discovery 2:52-62.
Adams, et 1985, Nature 318:533-38.
Agarwal et al., 1978, Methods Enzymol. 51:483-490.
Alexander et al., 1987, Mol. Cell. Biol., 7:1436-44.
Appelbaum, 1999, Semin Hematol 36:2-8.
Benoist et al., 1981, Nature 290:304-10.
Billiau, 1988, Immunol. Today 9:37-40.
Brinster et al., 1982, Nature 296:39-42.
Burton et al., 1992, Advances in Immunology 51: 1-84.
Ravetch, et al., 2001 Annu. Rev. Immunol. 19: 275-90.
Carillo et al., 1988 SIAM J. Applied Math., 48:1073-1084.
Caron et al., 1992, Cancer Res. 52:6761-7.
Chothia et al., 1987, J. Mol. Biol. 196: 901-17.
Chothia et al., 1989, Nature 342: 877-83.
Cosman et al., 1984, Nature 312: 768-71.
DeBoer et al., 1983, Proc. Natl. Acad. Sci., 80:21-25.
Otwinowski et al., 1997, Methods Enzymol. 276:307-326.
Desiderio et al., 2001, J. Mol. Biol. 310:603-15.
Doublie, 1997, Methods Enzymol. 276:523-30.
Durbin et al., 1998, Biological Sequence Analysis, Cambridge University Press, 1-325.
Chu et al., 1981, Gene 13:197-202.
Eppstein et al., 1985, Proc. Natl. Acad. Sci. USA 82:3688-3692.
Graham et al., 1973, Virology 52:456-467.
Grosschedl et al., 1984, Cell 38:647-58.
Hammer et al., 1987, Science 235:53-58.
Hanahan, 1985, Nature 315:115-22.
Hatzis et al., 1998, Journal Biol. Chem. 273:30239-30243.
Hendrickson et al., 1997, Methods Enzymol. 276:494-523.
Herrstrom et al., 1998, Mol. Pharmacol. 53:270-273.
Horneff et al., 1991, Clin. Immunol. & Immunopathol. 59:89-103.
Jones et al., 1986, Nature 321:522-25.
Verhoeyen et al., 1988, Science 239:1534-36.
Jones et al., 1991, Acta Cryst. A47:110-119.
Kabsch, 1993, J. Appl. Crystal 26:795-800.
Kang et al., 1991, Proc. Natl. Acad. Sci. 88:11120-23.
Kelsey et al., 1987, Genes and Devel. 1:161-71.
Kohler et al., 1975, Nature 256:495-97.
Kostelny et al., 1992, J. Immunol. 148:1547-1553.
Krumlauf et al., 1985, Mol. Cell. Biol., 5:1639-48.
Langer et al., 1981, J. Biomed. Mater. Res. 15:267-277.
Langer, 1982, Chemtech 12:98-105.
LaPlanche et al., 1986, Nucl. Acids Res., 14:9081-93.
Leder et al., 1986, Cell 45:485-95.
MacDonald, 1987, Hepatology 7:42S-51S.
Mason et al., 1986, Science 234:1372-78.
Medesan et al., 1998, Eur. J. Immunol. 28: 2092-2100.
Mendez et al., 1997, Nature Genetics 15:146-156.
Magram et al., 1985, Nature 315:338-40.
Kollias et al., 1986, Cell 46:89-94.

(Continued)

*Primary Examiner* — Karen Cochrane Carlson
(74) *Attorney, Agent, or Firm* — McDonnell Boehnen Hulbert & Berghoff LLP

(57) ABSTRACT

The invention provides methods for enhancing efficiency of prodrugs by specifically engineered enzymes with altered or enhanced activity and broader substrate specificity towards nucleoside analogs used in cancer chemotherapy, and delivering the enzymes to specific target cells in a patient. The invention also provides modified deoxycytidine kinase (dCK) mutants with such enhanced activities. Furthermore, the invention provides antibody-conjugated enzymes, pharmaceutical composition and kit containing the same, that can be specifically delivered to tumor cells.

67 Claims, 15 Drawing Sheets

OTHER PUBLICATIONS

Navaza, 1994, Acta Cryst. A50:157-163.
Ornitz et al., 1986, Cold Spring Harbor Symp. Quant. Biol. 50:399-409.
Perrakis et al., 1999, Nat. Struct. Biol. 6:458-63.
Pinkert et al., 1987, Genes and Devel. 1:268-76.
Readhead et al., 1987, Cell 48:703-12.
Murshudov et al., 1997, Acta Cryst. D53:240-255.
Sabini et al., 2003, Nat. Struct. Biol. 10:513-519.
Shani, 1985, Nature 314:283-86.
Schier et al., 1996, J. Mol. Biol. 263:551-67.
Yang et al., 1995, J. Mol. Biol. 254:392-403.
Shields et al., 2001, Journal of Biol. Chem. 276: 6591-6604.
Sidman et al., 1983, Biopolymers 22:547-556.
Smal et al., 2006, Nucleosides Nucleotides Nucleic Acids, 25:1141-1146.
Songsivilai et al., 1990, Clin. Exp. Immunol. 79: 315-321.
Stec et al., 1984, J. Am. Chem. Soc., 106:6077-6079.
Stein et al., 1988, Nucl. Acids Res., 16:3209-3221.
Zon et al., 1991, Anti-Cancer Drug Design, 6:539-568.
Stemmer, 1994, Nature 370:389-391.
Swift et al., 1984, Cell 38:639-46.
Telleman et al., 2000, Immunology 100: 245-251.
Terwilliger, 1999, Acta Cryst. Section D, 55:1863-1871.
Thomsen et al., 1984, Proc. Natl. Acad. Sci. USA, 81:659-663.
Tjandra et al., 1990, Immunol Cell Biol. 68:367-76.
Uhlmann et al., 1990, Chemical Reviews, 90:543-584.
van den Beucken et al., 2001, J. Mol. Biol. 310:591-601.
Villa-Kamaroff et al., 1978, Proc. Natl. Acad. Sci. U.S.A., 75:3727-31.
Wagner et al., 1981, Proc. Natl. Acad. Sci. U.S.A. 78:1441-45.
Yamamoto, et al., 1980, Cell 22:787-97.
Zon et al., 1991, Oligonucleotides and Analogues: A Practical Approach, pp. 87-108, Oxford University Press, Oxford England.
McSorley, et al., 2008, FEBS Letters, 582: 720-24.
Hazra et al., Biochemistry, 2009 48:1256-1263.
Bergman et al., 1999, Biochem. Pharmacol. 57: 397-406.
Blackstock et al., 2001, Clin. Cancer Res. 7:3263-8.
Blakey et al., 1997, Exp. Opin. Ther. Patents, 7:966-977.
Estey et al., 1987, Leukemia 1:580-3.
Estey, 2000, Blood 96: 1670-3.
Gandhi et al., 1993, J. Clin. Oncol. 11: 116-24.
Gladstone et al., 2003, Blood, 102: 138(A).
Goan et al., 1999, Cancer Res. 59: 4204-7.
Hapke et al., 1996, Cancer Res. 56: 2343-7.
Hubert et al., 1999, Proc Natl Acad Sci USA 7:4523-8.
Iacoboni et al., 1986, J. Clin. Oncol. 4:1079-88.
Iyidogan et al., 2008, Biochemistry, 47:4711-4720.
Johansson et al., Nature Structural Biology, 8:616-619, 2001.
Kabouridis, 2003, Trends in Biotechnology 21:498-503.
Kakihara et al,, 1998, Leuk. Lymphoma 31:405-9.
Kantarjian et al., 1986, Am. J. Med. 81:387-94.
Kossman et al., 1999, Clin. Can. Res. 5:2748-55.
Knecht et al., 2002, EMBO J. 21:1873-1880.
Lotfi et al., 1999, Clin. Cancer Res. 5:2438-44.
Mansson et al., 2003, Biochem. Pharmacol. 65:237-247.
McSorley et al., 2008, FEBS Letters, 582:720-724.
Owens et al., 1992, Cancer Res. 52:2389-93.
Plunkett et al., 1985, Semin Oncol 12:20-30.
Ruiz van Haperen et al., 1994, Cancer Res. 54: 4138-43.
Sandlie et al., 2003, Nat. Rev. Drug Discovery 2:52-62.
Sequence Search Result-SEQ ID No. 1 (2009).
Stegmann et al., 1995, Blood 85: 1188-94.
Van Rompay, et al., 2000, Pharmacol. Ther. 87: 189-98.
Zhu et al., 2000, J. Biol. Chem. 275: 26727.

SEQUENCE LISTING

```
<160> NUMBER OF SEQ ID NOS: 23

<210> SEQ ID NO 1
<211> LENGTH: 260
<212> TYPE: PRT
<213> ORGANISM: Homo sapiens

<400> SEQUENCE: 1

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Asp Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
```

```
                210                 215                 220
Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 2
<211> LENGTH: 277
<212> TYPE: PRT
<213> ORGANISM: Homo sapiens

<400> SEQUENCE: 2

Met Ala Ala Gly Arg Leu Phe Leu Ser Arg Leu Arg Ala Pro Phe Ser
1               5                   10                  15

Ser Met Ala Lys Ser Pro Leu Glu Gly Val Ser Ser Arg Gly Leu
            20                  25                  30

His Ala Gly Arg Gly Pro Arg Arg Leu Ser Ile Glu Gly Asn Ile Ala
            35                  40                  45

Val Gly Lys Ser Thr Phe Val Lys Leu Leu Thr Lys Thr Tyr Pro Glu
50                  55                  60

Trp His Val Ala Thr Glu Pro Val Ala Thr Trp Gln Asn Ile Gln Ala
65                  70                  75                  80

Ala Gly Asn Gln Lys Ala Cys Thr Ala Gln Ser Leu Gly Asn Leu Leu
                85                  90                  95

Asp Met Met Tyr Arg Glu Pro Ala Arg Trp Ser Tyr Thr Phe Gln Thr
            100                 105                 110

Phe Ser Phe Leu Ser Arg Leu Lys Val Gln Leu Glu Pro Phe Pro Glu
        115                 120                 125

Lys Leu Leu Gln Ala Arg Lys Pro Val Gln Ile Phe Glu Arg Ser Val
130                 135                 140

Tyr Ser Asp Arg Tyr Ile Phe Ala Lys Asn Leu Phe Glu Asn Gly Ser
145                 150                 155                 160

Leu Ser Asp Ile Glu Trp His Ile Tyr Gln Asp Trp His Ser Phe Leu
                165                 170                 175

Leu Trp Glu Phe Ala Ser Arg Ile Thr Leu His Gly Phe Ile Tyr Leu
            180                 185                 190

Gln Ala Ser Pro Gln Val Cys Leu Lys Arg Leu Tyr Gln Arg Ala Arg
        195                 200                 205

Glu Glu Glu Lys Gly Ile Glu Leu Ala Tyr Leu Glu Gln Leu His Gly
210                 215                 220

Gln His Glu Ala Trp Leu Ile His Lys Thr Thr Lys Leu His Phe Glu
225                 230                 235                 240

Ala Leu Met Asn Ile Pro Val Leu Val Leu Asp Val Asn Asp Asp Phe
                245                 250                 255

Ser Glu Glu Val Thr Lys Gln Glu Asp Leu Met Arg Glu Val Asn Thr
            260                 265                 270

Phe Val Lys Asn Leu
        275

<210> SEQ ID NO 3
<211> LENGTH: 250
<212> TYPE: PRT
<213> ORGANISM: Drosophila melanogaster

<400> SEQUENCE: 3
```

```
Met Ala Glu Ala Ala Ser Cys Ala Arg Lys Gly Thr Lys Tyr Ala Glu
1               5                   10                  15

Gly Thr Gln Pro Phe Thr Val Leu Ile Glu Gly Asn Ile Gly Ser Gly
            20                  25                  30

Lys Thr Thr Tyr Leu Asn His Phe Glu Lys Tyr Lys Asn Asp Ile Cys
        35                  40                  45

Leu Leu Thr Glu Pro Val Glu Lys Trp Arg Asn Val Asn Gly Val Asn
50                  55                  60

Leu Leu Glu Leu Met Tyr Lys Asp Pro Lys Lys Trp Ala Met Pro Phe
65                  70                  75                  80

Gln Ser Tyr Val Thr Leu Thr Met Leu Gln Ser His Thr Ala Pro Thr
                85                  90                  95

Asn Lys Lys Leu Lys Ile Met Glu Arg Ser Ile Phe Ser Ala Arg Tyr
            100                 105                 110

Cys Phe Val Glu Asn Met Arg Arg Asn Gly Ser Leu Glu Gln Gly Met
        115                 120                 125

Tyr Asn Thr Leu Glu Glu Trp Tyr Lys Phe Ile Glu Glu Ser Ile His
    130                 135                 140

Val Gln Ala Asp Leu Ile Ile Tyr Leu Arg Thr Ser Pro Glu Val Ala
145                 150                 155                 160

Tyr Glu Arg Ile Arg Gln Arg Ala Arg Ser Glu Glu Ser Cys Val Pro
                165                 170                 175

Leu Lys Tyr Leu Gln Glu Leu His Glu Leu His Glu Asp Trp Leu Ile
            180                 185                 190

His Gln Arg Arg Pro Gln Ser Cys Lys Val Leu Val Leu Asp Ala Asp
        195                 200                 205

Leu Asn Leu Glu Asn Ile Gly Thr Glu Tyr Gln Arg Ser Glu Ser Ser
    210                 215                 220

Ile Phe Asp Ala Ile Ser Ser Asn Gln Gln Pro Ser Pro Val Leu Val
225                 230                 235                 240

Ser Pro Ser Lys Arg Gln Arg Val Ala Arg
                245                 250

<210> SEQ ID NO 4
<211> LENGTH: 232
<212> TYPE: PRT
<213> ORGANISM: Homo sapiens

<400> SEQUENCE: 4

Val Gln Arg Tyr Ala Trp Pro Pro Asp Lys Glu Gln Glu Lys Glu Lys
1               5                   10                  15

Lys Ser Val Ile Cys Val Glu Gly Asn Ile Ala Ser Gly Lys Thr Thr
            20                  25                  30

Cys Leu Glu Phe Phe Ser Asn Ala Thr Asp Val Glu Val Leu Thr Glu
        35                  40                  45

Pro Val Ser Lys Trp Arg Asn Val Arg Gly His Asn Pro Leu Gly Leu
50                  55                  60

Met Tyr His Asp Ala Ser Arg Trp Gly Leu Thr Leu Gln Thr Tyr Val
65                  70                  75                  80

Gln Leu Thr Met Leu Asp Arg His Thr Arg Pro Gln Val Ser Ser Val
                85                  90                  95

Arg Leu Met Glu Arg Ser Ile His Ser Ala Arg Tyr Ile Phe Val Glu
            100                 105                 110

Asn Leu Tyr Arg Ser Gly Lys Met Pro Glu Val Asp Tyr Val Val Leu
        115                 120                 125
```

```
Ser Glu Trp Phe Asp Trp Ile Leu Arg Asn Met Asp Val Ser Val Asp
    130                 135                 140

Leu Ile Val Tyr Leu Arg Thr Asn Pro Glu Thr Cys Tyr Gln Arg Leu
145                 150                 155                 160

Lys Lys Arg Cys Arg Glu Glu Lys Val Ile Pro Leu Glu Tyr Leu
                165                 170                 175

Glu Ala Ile His His Leu His Glu Glu Trp Leu Ile Lys Gly Ser Leu
            180                 185                 190

Phe Pro Met Ala Ala Pro Val Leu Val Ile Glu Ala Asp His His Met
        195                 200                 205

Glu Arg Met Leu Glu Leu Phe Glu Gln Asn Arg Asp Arg Ile Leu Thr
    210                 215                 220

Pro Glu Asn Arg Lys His Cys Pro
225                 230

<210> SEQ ID NO 5
<211> LENGTH: 260
<212> TYPE: PRT
<213> ORGANISM: Artificial Sequence
<220> FEATURE:
<223> OTHER INFORMATION: Synthetic - A100V/R104M/D133A human dCK mutant

<400> SEQUENCE: 5

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
                20                  25                  30

Gly Lys Ser Thr Phe Val Asn Ile Leu Lys Gln Leu Cys Glu Asp Trp
            35                  40                  45

Glu Val Val Pro Glu Pro Val Ala Arg Trp Cys Asn Val Gln Ser Thr
50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Val Cys Leu Ser Met Ile Arg Ala Gln Leu Ala Ser Leu
                100                 105                 110

Asn Gly Lys Leu Lys Asp Ala Glu Lys Pro Val Leu Phe Phe Glu Arg
            115                 120                 125

Ser Val Tyr Ser Ala Arg Tyr Ile Phe Ala Ser Asn Leu Tyr Glu Ser
130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255
```

```
Leu Ser Thr Leu
            260

<210> SEQ ID NO 6
<211> LENGTH: 260
<212> TYPE: PRT
<213> ORGANISM: Artificial Sequence
<220> FEATURE:
<223> OTHER INFORMATION: Synthetic - R104M/D133A human dCK mutant

<400> SEQUENCE: 6

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Met Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 7
<211> LENGTH: 260
<212> TYPE: PRT
<213> ORGANISM: Artificial Sequence
<220> FEATURE:
<223> OTHER INFORMATION: Synthetic - A100V/R104Q/D133A human dCK mutant

<400> SEQUENCE: 7

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30
```

```
Gly Lys Ser Thr Phe Val Asn Ile Leu Lys Gln Leu Cys Glu Asp Trp
            35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Val Cys Leu Ser Gln Ile Arg Ala Gln Leu Ala Ser Leu
                100                 105                 110

Asn Gly Lys Leu Lys Asp Ala Glu Lys Pro Val Leu Phe Phe Glu Arg
            115                 120                 125

Ser Val Tyr Ser Ala Arg Tyr Ile Phe Ala Ser Asn Leu Tyr Glu Ser
        130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
                180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 8
<211> LENGTH: 260
<212> TYPE: PRT
<213> ORGANISM: Artificial Sequence
<220> FEATURE:
<223> OTHER INFORMATION: Synthetic - R104Q/D133A human dCK mutant

<400> SEQUENCE: 8

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
            35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Gln Ile Arg Ala Gln Leu Ala Ser Leu
                100                 105                 110

Asn Gly Lys Leu Lys Asp Ala Glu Lys Pro Val Leu Phe Phe Glu Arg
            115                 120                 125

Ser Val Tyr Ser Ala Arg Tyr Ile Phe Ala Ser Asn Leu Tyr Glu Ser
```

```
            130                 135                 140
Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 9
<211> LENGTH: 260
<212> TYPE: PRT
<213> ORGANISM: Artificial Sequence
<220> FEATURE:
<223> OTHER INFORMATION: Synthetic - A100V/R104L/D133A human dCK mutant

<400> SEQUENCE: 9

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Val Cys Leu Ser Leu Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240
```

```
Asp Phe Lys Asp Lys Tyr Glu Ser Leu Val Glu Lys Val Lys Glu Phe
            245                 250                 255

Leu Ser Thr Leu
            260

<210> SEQ ID NO 10
<211> LENGTH: 260
<212> TYPE: PRT
<213> ORGANISM: Artificial Sequence
<220> FEATURE:
<223> OTHER INFORMATION: Synthetic - R104L/D133A human dCK mutant

<400> SEQUENCE: 10

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Leu Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
            245                 250                 255

Leu Ser Thr Leu
            260

<210> SEQ ID NO 11
<211> LENGTH: 260
<212> TYPE: PRT
<213> ORGANISM: Artificial Sequence
<220> FEATURE:
<223> OTHER INFORMATION: Synthetic - A100V/R104I/D133A human dCK mutant

<400> SEQUENCE: 11

Met Ala Thr Pro Pro Lys Arg Ser Cys Pro Ser Phe Ser Ala Ser Ser
1               5                   10                  15
```

```
Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Val Cys Leu Ser Ile Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 12
<211> LENGTH: 260
<212> TYPE: PRT
<213> ORGANISM: Artificial Sequence
<220> FEATURE:
<223> OTHER INFORMATION: Synthetic - R104I/D133A human dCK mutant

<400> SEQUENCE: 12

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Ile Ile Arg Ala Gln Leu Ala Ser Leu
            100                 105                 110
```

```
Asn Gly Lys Leu Lys Asp Ala Glu Lys Pro Val Leu Phe Glu Arg
            115                 120                 125

Ser Val Tyr Ser Ala Arg Tyr Ile Phe Ala Ser Asn Leu Tyr Glu Ser
        130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 13
<211> LENGTH: 260
<212> TYPE: PRT
<213> ORGANISM: Artificial Sequence
<220> FEATURE:
<223> OTHER INFORMATION: Synthetic - S74E/A100V/R104Q/D133A human dCK
      mutant

<400> SEQUENCE: 13

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Glu Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Val Cys Leu Ser Gln Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205
```

```
His Tyr Lys His Glu Ser Trp Leu Leu His Arg Thr Leu Lys Thr Asn
        210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 14
<211> LENGTH: 260
<212> TYPE: PRT
<213> ORGANISM: Artificial Sequence
<220> FEATURE:
<223> OTHER INFORMATION: Synthetic - S74E/R104Q/D133A human dCK mutant

<400> SEQUENCE: 14

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
                20                  25                  30

Gly Lys Ser Thr Phe Val Asn Ile Leu Lys Gln Leu Cys Glu Asp Trp
            35                  40                  45

Glu Val Val Pro Glu Pro Val Ala Arg Trp Cys Asn Val Gln Ser Thr
50                  55                  60

Gln Asp Glu Phe Glu Glu Leu Thr Met Glu Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Gln Ile Arg Ala Gln Leu Ala Ser Leu
            100                 105                 110

Asn Gly Lys Leu Lys Asp Ala Glu Lys Pro Val Leu Phe Phe Glu Arg
            115                 120                 125

Ser Val Tyr Ser Ala Arg Tyr Ile Phe Ala Ser Asn Leu Tyr Glu Ser
130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
            195                 200                 205

His Tyr Lys His Glu Ser Trp Leu Leu His Arg Thr Leu Lys Thr Asn
        210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 15
<211> LENGTH: 260
<212> TYPE: PRT
<213> ORGANISM: Artificial Sequence
<220> FEATURE:
<223> OTHER INFORMATION: Synthetic - S74E/A100V/R104L/D133A human dCK
```

-continued mutant

<400> SEQUENCE: 15

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Glu Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Val Cys Leu Ser Leu Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 16
<211> LENGTH: 260
<212> TYPE: PRT
<213> ORGANISM: Artificial Sequence
<220> FEATURE:
<223> OTHER INFORMATION: Synthetic - S74E/R104L/D133A human dCK mutant

<400> SEQUENCE: 16

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Glu Gln Lys Asn Gly Gly Asn
65                  70                  75                  80

Val Leu Gln Met Met Tyr Glu Lys Pro Glu Arg Trp Ser Phe Thr Phe
              85                  90                  95

Gln Thr Tyr Ala Cys Leu Ser Leu Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
        260

<210> SEQ ID NO 17
<211> LENGTH: 260
<212> TYPE: PRT
<213> ORGANISM: Artificial Sequence
<220> FEATURE:
<223> OTHER INFORMATION: Synthetic - S74E/A100V/R104I/D133A human dCK
      mutant

<400> SEQUENCE: 17

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Glu Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Val Cys Leu Ser Ile Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

```
Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
            195                 200                 205

His Tyr Lys His Glu Ser Trp Leu Leu His Arg Thr Leu Lys Thr Asn
            210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 18
<211> LENGTH: 260
<212> TYPE: PRT
<213> ORGANISM: Artificial Sequence
<220> FEATURE:
<223> OTHER INFORMATION: Synthetic - S74E/R104I/D133A human dCK mutant

<400> SEQUENCE: 18

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
50                  55                  60

Gln Asp Glu Phe Glu Glu Leu Thr Met Glu Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Ile Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
            195                 200                 205

His Tyr Lys His Glu Ser Trp Leu Leu His Arg Thr Leu Lys Thr Asn
            210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260
```

```
<210> SEQ ID NO 19
<211> LENGTH: 260
<212> TYPE: PRT
<213> ORGANISM: Artificial Sequence
<220> FEATURE:
<223> OTHER INFORMATION: Synthetic - S74E/A100V/R104M/D133A human dCK
      mutant

<400> SEQUENCE: 19

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
                20                  25                  30

Gly Lys Ser Thr Phe Val Asn Ile Leu Lys Gln Leu Cys Glu Asp Trp
            35                  40                  45

Glu Val Val Pro Glu Pro Val Ala Arg Trp Cys Asn Val Gln Ser Thr
50                  55                  60

Gln Asp Glu Phe Glu Glu Leu Thr Met Glu Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Val Cys Leu Ser Met Ile Arg Ala Gln Leu Ala Ser Leu
                100                 105                 110

Asn Gly Lys Leu Lys Asp Ala Glu Lys Pro Val Leu Phe Phe Glu Arg
            115                 120                 125

Ser Val Tyr Ser Ala Arg Tyr Ile Phe Ala Ser Asn Leu Tyr Glu Ser
130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 20
<211> LENGTH: 260
<212> TYPE: PRT
<213> ORGANISM: Artificial Sequence
<220> FEATURE:
<223> OTHER INFORMATION: Synthetic - S74E/R104M/D133A human dCK mutant

<400> SEQUENCE: 20

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
                20                  25                  30

Gly Lys Ser Thr Phe Val Asn Ile Leu Lys Gln Leu Cys Glu Asp Trp
            35                  40                  45
```

```
Glu Val Val Pro Glu Pro Val Ala Arg Trp Cys Asn Val Gln Ser Thr
 50                  55                  60
Gln Asp Glu Phe Glu Glu Leu Thr Met Glu Gln Lys Asn Gly Gly Asn
 65                  70                  75                  80
Val Leu Gln Met Met Tyr Glu Lys Pro Glu Arg Trp Ser Phe Thr Phe
                 85                  90                  95
Gln Thr Tyr Ala Cys Leu Ser Met Ile Arg Ala Gln Leu Ala Ser Leu
                100                 105                 110
Asn Gly Lys Leu Lys Asp Ala Glu Lys Pro Val Leu Phe Phe Glu Arg
            115                 120                 125
Ser Val Tyr Ser Ala Arg Tyr Ile Phe Ala Ser Asn Leu Tyr Glu Ser
130                 135                 140
Glu Cys Met Asn Glu Thr Glu Trp Thr Ile Tyr Gln Asp Trp His Asp
145                 150                 155                 160
Trp Met Asn Asn Gln Phe Gly Gln Ser Leu Glu Leu Asp Gly Ile Ile
                165                 170                 175
Tyr Leu Gln Ala Thr Pro Glu Thr Cys Leu His Arg Ile Tyr Leu Arg
            180                 185                 190
Gly Arg Asn Glu Glu Gln Gly Ile Pro Leu Glu Tyr Leu Glu Lys Leu
        195                 200                 205
His Tyr Lys His Glu Ser Trp Leu Leu His Arg Thr Leu Lys Thr Asn
    210                 215                 220
Phe Asp Tyr Leu Gln Glu Val Pro Ile Leu Thr Leu Asp Val Asn Glu
225                 230                 235                 240
Asp Phe Lys Asp Lys Tyr Glu Ser Leu Val Glu Lys Val Lys Glu Phe
                245                 250                 255
Leu Ser Thr Leu
            260

<210> SEQ ID NO 21
<211> LENGTH: 2618
<212> TYPE: DNA
<213> ORGANISM: Homo sapiens

<400> SEQUENCE: 21
gcggagcgcg cacgcgggaa cccgcgctgg aggcgggcga gggccgaggg gcagctaggg      60
agcgcggctt gaggagggcg gggccgcccc gcaggcccgc cagtgtcctc agctgcctcc     120
gcgcgccaaa gtcaaacccc gacacccgcc ggcgggccgg tgagctcact agctgacccg     180
gcaggtcagg atctggctta gcggcgccgc gagctccagt gcgcgcaccc gtggccgcct     240
cccagccctc tttgccggac gagctctggg ccgccacaag actaaggaat ggccaccccg     300
cccaagagaa gctgcccgtc tttctcagcc agctctgagg ggacccgcat caagaaaatc     360
tccatcgaag gaacatcgc tgcagggaag tcaacatttg tgaatatcct taaacaattg     420
tgtgaagatt gggaagtggt tcctgaacct gttgccagat ggtgcaatgt tcaaagtact     480
caagatgaat ttgaggaact acaatgtct cagaaaaatg gtgggaatgt tcttcagatg     540
atgtatgaga aacctgaacg atggtctttt accttccaaa catatgcctg tctcagtcga     600
ataagagctc agcttgcctc tctgaatggc aagctcaaag atgcagagaa acctgtatta     660
ttttttgaac gatctgtgta tagtgacagg tatattttg catctaattt gtatgaatct     720
```

```
gaatgcatga atgagacaga gtggacaatt tatcaagact ggcatgactg gatgaataac    780
caatttggcc aaagccttga attggatgga atcatttatc ttcaagccac tccagagaca    840
tgcttacata gaatatattt acggggaaga aatgaagagc aaggcattcc tcttgaatat    900
ttagagaagc ttcattataa acatgaaagc tggctcctgc ataggacact gaaaaccaac    960
ttcgattatc ttcaagaggt gcctatctta acactggatg ttaatgaaga ctttaaagac   1020
aaatatgaaa gtctggttga aaaggtcaaa gagttttga gtactttgtg atcttgctga   1080
agactacagg cagccaaatg ttccagata cttcagcttt gtgtatcttc gtaacttcat   1140
attaatataa gtttctttag aaacccaag tttttaatcg ttttgtttt aaggaaaaaa    1200
gatttttaaa atgaatctta tgcaaaactt tttgaccagt ttcttttctt ttgtttttt    1260
tttaaaaaag acatttaaag acaaagacat tatttctcat agcaggaaat gtagaggtag   1320
atggttccag tatcagcata gtgactaaac tacattataa aagatccagc ttccttctgt   1380
cattccctc ttttgtcttc ctcagcaggt tggctttttt ccctggtgcc tctcacttcg   1440
ttggtgacca gtttcttaaa ctgaaagctt taatgttaca tagtaaatgg tagtgtgtcc   1500
tgtgtaaatt agtgtaccta ttaaaagttg caaagtggaa ttaaaggaat ccctagaata   1560
aggattctga agttttattt taaattatta tcttcttaac agtttagtcc cacctcttac   1620
ttcctgcctc agtctgcttt ctctactgtc tggattaatt aggcagcctg ctataaagtt   1680
aaagtcacac atttctattt tgcaaacact gtgattactc tttgctttgt agtttgcttt   1740
gctttgtagg gttctgcttt taagtttttc tcttttcag acaaattact gataaaaatg   1800
atattgctct atatgtaata tatcctgaaa gcattatttt ttgttgaata ggaaataaaa   1860
ttaatgaaga cagaggctag aaagcatcca ttaattaatg agacacactt aactacttat   1920
ctctaaacca tctatgtgaa tatttgtaaa aataatgaat ggactcatct tagttctgta   1980
tataaatata ttttctttct agtttgttta gttaaggtgt gcagtgtttt tcctgtgtat   2040
taaacctttc cattttacgt tttagaaaat tttatgtatt ttaaaataag gggaagagtc   2100
attttcactt ttaaactact attttttcttt ccaagtcatt tttgttttg gtttcttatt   2160
caaagatgat aatttagtgg attaaccagt ccagacgcac tgatctttgc aaaggagact   2220
taatttcaaa tctgtaatta ccatacataa actgtctcat tatacgtatg cattttttta   2280
gtttgttttt gtttggtata aattaatttg ttaattaaat atttcttaag tataaacctt   2340
atgaactaca gtggagctac actcattgaa atgtaatttc agttctaaaa agatgtaata   2400
atcatttag aattaaaatt tattctactt ttaaataaat tatgaatatt aaaggtgaaa   2460
attgtataaa ttactttgat tccatttta gtggagacat atttcagtga ttttttagtaa   2520
cctttaaaaa tgtataatga cttttaaat ttgtagaatt gaaagacgc taataaaaat   2580
ttattattta tttgtcatga ctcaaaaaaa aaaaaaaa                          2618

<210> SEQ ID NO 22
<211> LENGTH: 33
<212> TYPE: DNA
<213> ORGANISM: Artificial Sequence
<220> FEATURE:
<223> OTHER INFORMATION: Synthetic - Human dCK forward PCR primer

<400> SEQUENCE: 22
ggaattccat atggccaccc cgcccaagag aag                                33

<210> SEQ ID NO 23
<211> LENGTH: 30
<212> TYPE: DNA
```

```
<213> ORGANISM: Artificial Sequence
<220> FEATURE:
<223> OTHER INFORMATION: Synthetic - Human dCK reverse PCR primer

<400> SEQUENCE: 23
cgcggatcct cacaaagtac tcaaaaactc                                30
```

USE OF SPECIFICALLY ENGINEERED ENZYMES TO ENHANCE THE EFFICACY OF PRODRUGS

This application is a U.S. National Phase application under 35 U.S.C. §371 of the International Application No. PCT/US2009/044318, filed May 18, 2009. This invention relates to and claims the benefit of priority to U.S. Provisional Application Ser. Nos. 61/054,400, and 61/054,403, both of which were filed May 19, 2008, and International Application No. PCT/US2009/044318, filed May 18, 2009. The disclosure of each of the above applications is hereby incorporated by reference in its entirety.

This invention was made with government support under grant number RO1 CA95687 awarded by the National Cancer Institute and National Institutes of Health. The government has certain rights in the invention.

BACKGROUND OF THE INVENTION

1. Field of the Invention

The invention relates to reagents and methods for enhancing efficacy of prodrugs. Specifically, the invention relates to targeted delivery of enzymes, in particular specifically engineered enzymes, to cells in need thereof, particularly for converting prodrugs to chemotherapeutically active drugs. The invention is particularly directed to targeted delivery of said enzymes to cancer cells of specific tumor types. Specifically, the invention provides genetically-engineered modified human deoxycytidine kinase (dCK) with enhanced activity towards nucleoside analogs used in cancer chemotherapy.

2. Background of the Related Art

Many currently-used chemotherapeutic agents are members of a class of drugs referred to as anti-metabolites. One type of such anti-metabolite are molecules that block or subvert one or more of the metabolic pathways involved in DNA synthesis by mimicking naturally-occurring nucleic acid building blocks. Many of this type of anti-metabolite are nucleoside analogs (NAs). These NAs themselves usually do not possess any therapeutic activity (and thus are properly termed prodrugs) and rely on their conversion, for the most part to the triphosphorylated form, to become active (prodrug-to-drug metabolism).

The efficiency of conversion from the administered nucleoside to the active triphosphorylated form determines the efficacy of these types of prodrugs. The serial phosphorylation of NAs to their triphosphorylated metabolite, via monophosphate and diphosphate intermediates, is catalyzed by human cellular kinases, with deoxycytidine kinase (dCK) playing a major role. dCK transfers a phosphoryl group from ATP (or other triphosphorylated nucleotides) to deoxycytidine (dC). Native dCK has been shown to localize in the cytoplasm, though over-expression of dCK from a transfected construct may result in nuclear localization of dCK (Hatzis et al., 1998, *Journal Biol. Chem.* 273:30239-30243). dCK is required for the phosphorylation of numerous NAs used in chemotherapy, including AraC (1-β-D-arabinofuranosylcytosine; Cytarabine), dFdC (2',2'-difluorodeoxycytidine; Gemcitabine), FaraA (2-fluoro-9-β-D-arabinosyladenine; Fludarabine) and 2CdA (2-chlorodeoxyadenosine, Cladribine) (Van Rompay et al., 2000, *Pharmacol. Ther.* 87:189-98). Therefore, the activity of dCK is one of the factors that determine the sensitivity of cancer (including leukemias and certain solid tumors) to deoxynucleoside toxicity and hence, therapy (Stegmann et al., 1995, Blood 85:1188-94; Lotfi et al., 1999, *Clin. Cancer Res.* 5:2438-44; Kakihara et al., 1998, *Leuk.* *Lymphoma* 31:405-9; Bergman et al., 1999, *Biochem. Pharmacol.* 57:397-406; Goan et al, 1999, *Cancer Res.* 59:4204-7).

There is a direct correlation between dCK enzymatic activity in tumor cell lines and the sensitivity of those cells to the toxicity of nucleoside analog chemotherapeutic prodrugs (Hapke et al., 1996, *Cancer Res.* 56:2343-7). Cells lacking dCK activity are resistant to a variety of drugs, including ara-C, cladribine, fludarabine and gemcitabine (Owens et al., 1992, *Cancer Res.* 52:2389-93; Ruiz van Haperen et al., 1994, *Cancer Res.* 54:4138-43) and drug sensitivity to ara-C can be restored by expressing functional dCK protein in cells that do not express this enzyme natively or in which only mutationally-inactivated forms thereof are expressed (Stegmann et al., 1995, *Blood* 85:1188-94). Moreover, in vivo studies conducted on animal tumors using gemcitabine showed that increased dCK activity, mediated by dCK gene transfer, resulted in enhanced accumulation and prolonged elimination kinetics of gemcitabine triphosphate, and ultimately, to a better tumor response to the prodrug (Blackstock et al., 2001, *Clin. Cancer Res.* 7:3263-8).

More efficient prodrug-to-chemotherapeutic drug conversion, i.e. from NA to NA-triphosphate, would greatly increase the potency of such prodrugs and reduce undesired side effects common in chemotherapeutic treatments (due at least in part to higher concentrations of the drug needed to achieve a therapeutic result, with concomitant toxicity to normal cells and tissues). Higher concentrations of the active metabolites of nucleoside analog prodrugs, particularly in the cancer cells themselves, would result in a better therapeutic index for these prodrugs. In addition, some tumor cells develop resistance to chemotherapeutic agents that are administered as prodrugs and activated by enzymes expressed in target tumor cells, by reducing or eliminating expression of the gene(s) encoding the enzymatic activity. Resistance arising from such down-regulation of cellular gene expression could be overcome by targeted delivery of the enzyme directly to the tumor cell. Additionally, targeted delivery into cancer cells of a modified enzyme that has acquired additional substrate specificity as compared to the wild type enzyme allows the use of additional NAs to treat the targeted cancer cells. Thus, there is a need for more efficient enzymes and enzymes that utilize a wider variety of substrate NAs, especially NAs that are not normally phosphorylated by wild-type cellular enzymes, and for methods of using these enzymes to treat cancer cells.

SUMMARY OF THE INVENTION

The invention provides reagents and methods for targeted delivery of enzymes, in particular specifically engineered human enzymes capable of converting prodrugs to chemotherapeutically-active or activated forms of said prodrugs, to cells in need thereof. The invention in particular embodiments provides said reagents and methods for targeted delivery to cells, most preferably cancer cells, of modified deoxycytidine kinases (dCK), most preferably human dCK, with improved catalytic efficiency or extended or additional substrate specificity compared with wild type dCK, to produce or increase therapeutic effectiveness of nucleoside prodrugs in said cells.

In one aspect, the invention provides a modified human dCK of the invention that has amino acid substitutions at positions 104 and 133 wherein the amino acid positions are numbered according to the wild type dCK sequence (as shown in FIG. 2C, SEQ ID NO:1). In certain particular embodiments, the modified human deoxycytidine kinase of the invention has an amino acid sequence as identified by SEQ ID NO:1, wherein the amino acid residue 104 and the amino acid residue 133 are substituted. Suitable amino acid substitutions at position 104 comprise a methionine, glutamine, asparagine, valine, phenylalanine, isoleucine, leucine, lysine or histidine, more preferably a methionine, glutamine, leucine, isoleucine, valine, or phenylalanine, and most preferably a glutamine, leucine, or isoleucine substitution. Suitable amino acid substitutions at amino acid position 133 comprise an alanine, glycine, valine, threonine, serine, proline, isoleucine, leucine, glutamine, asparagine or histidine, and preferably an alanine, serine, or threonine substitution. In certain embodiments, the modified human dCK has a glutamine substitution at amino acid position 104, and an alanine substitution at position 133. In particular embodiments, the modified human dCK has an amino acid sequence as set forth in SEQ ID NO:8. In other embodiments, the modified human dCK has a leucine substitution at amino acid position 104, and an alanine substitution at position 133. In particular embodiments, the modified human dCK has an amino acid sequence as set forth in SEQ ID NO:10. In yet further embodiments, the modified human dCK has an isoleucine substitution at amino acid position 104, and an alanine substitution at position 133. In particular embodiments, the modified human dCK has an amino acid sequence as set forth in SEQ ID NO:12. In certain embodiments, the modified human dCK of the invention has a sequence that is at least 80%, 85%, 90%, or at least 95% identical to the sequence identified in SEQ ID NO:8, SEQ ID NO:10, or SEQ ID NO:12, wherein the modified human dCK has the specific amino acid substitutions at amino acid positions 104 and 133 as shown in the sequence as set forth in SEQ ID NO:8, SEQ ID NO:10, or SEQ ID NO:12, respectively.

In certain embodiments of this aspect, a modified human dCK of the invention further comprises an amino acid substitution at amino acid position 100. Suitable amino acid substitutions at position 100 comprise a glycine, valine, isoleucine, leucine, threonine, serine, or proline, more preferably a valine, isoleucine, or leucine, and most preferably a valine substitution. In certain embodiments, the modified human dCK has a valine substitution at position 100, a glutamine substitution at amino acid position 104, and an alanine substitution at position 133. In particular embodiments of the aspect, the modified human dCK has an amino acid sequence as set forth in SEQ ID NO:7. In other embodiments of the invention, the human dCK has a valine substitution at position 100, a leucine substitution at amino acid position 104, and an alanine substitution at position 133. In particular embodiments, the modified human dCK has an amino acid sequence as set forth in SEQ ID NO:9. In yet other embodiments, the human dCK has a valine substitution at position 100, an isoleucine substitution at amino acid position 104, and an alanine substitution at position 133. In particular embodiments, the modified human dCK has an amino acid sequence as set forth in SEQ ID NO:11. In certain other embodiments, the modified human dCK of the invention has a sequence that is at least 80%, 85%, 90%, or at least 95% identical to the sequence identified in SEQ ID NO:7, SEQ ID NO:9, or SEQ ID NO:11, wherein the modified human dCK has the specific amino acid substitutions at amino acid positions 100, 104, and 133 as shown in the sequence as set forth in SEQ ID NO:7, SEQ ID NO:9, or SEQ ID NO:11, respectively.

In certain other embodiments of this aspect, a modified human dCK of the invention with amino acid substitutions at positions 104 and 133 further comprises an amino acid substitution at amino acid position 74, most preferably a glutamic acid substitution. In certain embodiments, the modified human dCK has a glutamic acid substitution at position 74, a glutamine substitution at amino acid position 104, and an alanine substitution at position 133. In particular embodiments, the modified human dCK has an amino acid sequence as set forth in SEQ ID NO:14. In other embodiments, the modified human dCK has a glutamic acid substitution at position 74, a leucine substitution at amino acid position 104, and an alanine substitution at position 133. In particular embodiments, the modified human dCK has an amino acid sequence as set forth in SEQ ID NO:16. In certain embodiments, the modified human dCK has a glutamic acid substitution at position 74, an isoleucine substitution at amino acid position 104, and an alanine substitution at position 133. In particular, the modified human dCK has an amino acid sequence as set forth in SEQ ID NO:18. Further, in certain embodiments, the modified human dCK of the invention has a sequence that is at least 80%, 85%, 90%, or at least 95% identical to the sequence identified in SEQ ID NO:14, SEQ ID NO:16, or SEQ ID NO:18, wherein the modified human dCK has the specific amino acid substitutions at amino acid positions 74, 104, and 133 as shown in the sequence as set forth in SEQ ID NO:14, SEQ ID NO:16, or SEQ ID NO:18, respectively.

In yet other embodiments of this aspect, a modified human dCK of the invention with amino acid substitutions at positions 104 and 133 further comprises amino acid substitutions at amino acid positions 74 and 100. Suitable amino acid substitutions at position 100 and position 74 are as described above. In certain embodiments, the modified human dCK has a glutamic acid substitution at position 74, a valine substitution at position 100, a glutamine substitution at amino acid position 104, and an alanine substitution at position 133. In particular embodiments, the modified human dCK has an amino acid sequence as set forth in SEQ ID NO:13. In other embodiments, the modified human dCK has a glutamic acid substitution at position 74, a valine substitution at position 100, a leucine substitution at amino acid position 104, and an alanine substitution at position 133. In particular embodiments, the modified human dCK has an amino acid sequence as set forth in SEQ ID NO:15. In yet other embodiments, the modified human dCK has a glutamic acid substitution at position 74, a valine substitution at position 100, an isoleucine substitution at amino acid position 104, and an alanine substitution at position 133. In certain embodiments, the modified human dCK has an amino acid sequence as set forth in SEQ ID NO:17. In yet other embodiments, the modified human dCK of the invention has a sequence that is at least 80%, 85%, 90%, or at least 95% identical to the sequence identified in SEQ ID NO:13, SEQ ID NO:15, or SEQ ID NO:17, wherein the modified human dCK has the specific amino acid substitutions at amino acid positions 74, 100, 104, and 133 as shown in the sequence as set forth in SEQ ID NO:13, SEQ ID NO:15, or SEQ ID NO:17, respectively.

In another aspect, the invention provides a modified human dCK with amino acid substitutions at positions 74, 104, and 133, wherein the substitution at position 74 is glutamic acid, the substitution at position 104 is methionine, and the substitution at position 133 is alanine In particular embodiments of this aspect, the modified human dCK has an amino acid sequence as set forth in SEQ ID NO:20. In other embodiments, the modified human dCK further comprises an amino acid substitution at amino acid position 100, wherein the substitution at position 100 is valine. In certain embodiments, the modified human dCK has an amino acid sequence as set forth in SEQ ID NO:19.

In a further aspect, the invention provides modified human dCKs that phosphorylate a D-type or L-type thymidine analog. In certain embodiments, the thymidine analog is (E)-5-(2-bromovinyl)-2'-deoxyuridine (BVdU), AraT (1-β-D-arabinofuranosylthymine), L-dT (L-deoxythymidine, Telbivudine), or L-dU (L-deoxyuridine). In certain other embodiments, the thymidine analog is (E)-5-(2-bromovinyl)-2'-deoxyuridine (BVdU). Compositions or pharmaceutical compositions comprising the modified human dCK as described herein are also provided by the invention.

In yet another aspect, the invention provides isolated polynucleotides comprising nucleotide sequences that encode modified human dCKs of the invention. In particular embodiments of this aspect, the isolated polynucleotides encodes a modified human dCK with an amino acid sequence as identified by SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20.

In another aspect, the invention provides expression vectors comprising an isolated polynucleotide of the invention. In still another aspect, the invention provides host cells comprising expression vectors as described herein.

In yet another aspect, the invention provides methods for producing a modified human dCK polypeptide of the invention, comprising the steps of (a) culturing host cells of the invention under conditions effective to allow the expression of the modified dCK polypeptide, and (b) recovering the modified human dCK polypeptide from the cell culture.

The invention also provides said modified enzymes conjugated to an antibody, most preferably a monoclonal antibody or an immunologically-specific fragment thereof that is immunologically specific for and thus capable of recognizing cell surface antigens on cells, preferably tumor cells. In certain embodiments, said enzyme-antibody conjugates specifically recognize cell surface antigens on tumor cells susceptible to the therapeutic effects of said prodrugs, wherein the therapeutic efficacy of said prodrugs are improved thereby. In alternative embodiments, said enzyme-antibody conjugates specifically recognize cell surface antigens on tumor cells not susceptible to the therapeutic effects of said prodrugs, due at least in part to low reactivity of the native wild type enzymes to the prodrugs, lack of sufficient expression or non-expression of the native enzymes, or expression of a chemotherapeutic drug-resistant mutant form of the enzymes in the tumor cell, wherein the therapeutic efficacy of said prodrugs is produced thereby. For each of the particular embodiments of the invention, the enzyme can activate at least one chemotherapeutic agent or prodrug embodiments thereof In specific embodiments, the enzyme is a modified dCK as provided herein and the chemotherapeutic agent is a nucleoside analog that is a substrate of said enzyme. In specific embodiments, the modified dCK has an amino acid sequence as identified by SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20, and preferably SEQ ID NO:15 or SEQ ID NO:16. In certain embodiments, the antibody is capable of being internalized into the interior of the cell that expresses the cell surface marker for which the antibody is immunologically specific. In specific embodiments, the antibody is HuM195 (Protein Design Laboratories, Fremont, Calif.) that is immunologically-specific for the cell surface antigen CD33. In another specific embodiment, the antibody is Trastuzumab, also known by the trade name HERCEPTIN® (Genentech, South San Francisco, Calif.), which is immunologically-specific for the Her2/neu (erbB2) receptor.

The invention further provides compositions or pharmaceutical compositions comprising enzyme-antibody conjugates of the invention, most preferably at a therapeutically-effective concentration, and optionally comprising a pharmaceutical diluent, adjuvant or excipient. In particular embodiments, the enzyme-antibody conjugates of the invention comprise a modified dCK or a genetically engineered species of dCK as disclosed herein, conjugated to an antibody, most preferably a monoclonal antibody that specifically recognizes a cell surface antigen expressed on the surface of a cell, most preferably a tumor cell, and particularly a tumor cell that expresses reduced or absent levels of dCK or expresses a chemotherapeutic drug-resistant mutant dCK. In additional aspects, pharmaceutical compositions according to the invention further comprise a chemotherapeutic agent, preferably a nucleoside analog most preferably one activated by the modified dCK enzyme described herein.

The invention also provides methods of reducing or inhibiting proliferation of a tumor cell, comprising contacting the tumor cell with a prodrug and an enzyme-antibody conjugate or pharmaceutical composition of the invention. In certain embodiments of this aspect, the conjugate or pharmaceutical composition comprises an antibody and a modified human dCK that converts the prodrug into a therapeutically active drug. In specific embodiments, the modified dCK has a sequence as identified by SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20, and most preferably SEQ ID NO:15 or SEQ ID NO:16. In some embodiments, the prodrug is a D-type or L-type thymidine analog, and in specific embodiments, the thymidine analog is (E)-5-(2-bromovinyl)-2'-deoxyuridine (BVdU), L-dT, L-dU, or AraT. In other specific embodiments, the antibody is Trastuzumab or HuM195. In certain embodiments, the tumor cell is a breast tumor cell or a leukemia cell.

The invention further provides kits for inhibiting or reducing proliferation of tumor cells comprising a pharmaceutical composition of the invention comprising modified dCKs or antibody-conjugated modified dCKs, and instructions for use. In certain embodiments of this aspect of the invention, the kits further comprise a prodrug. In some embodiments, the prodrug is a D-type or L-type thymidine analog, and in one specific embodiment, the thymidine analog is (E)-5-(2-bromovinyl)-2'-deoxyuridine (BVdU).

In addition, the invention provides methods of treating a mammal more preferably a human and most preferably a human cancer patient bearing a primary, metastatic or recurrent tumor, or a tumor comprising cells that express natively or in a chemotherapeutic drug resistant embodiment thereof, reduced or absent levels of dCK activity that converts a nucleoside analog to an active drug. In certain embodiments, the cancer is leukemia or breast cancer. In other particular embodiments, the methods according to this aspect of the invention increase the therapeutic efficacy of a chemotherapeutic agent in a cancer patient. In particular embodiments, the patient bears tumor cells that are resistant to a chemotherapeutic agent administered as a prodrug and activated by enzymes expressed in target tumor cells, wherein said resistant tumor cells express an inactive mutant form of, or express at reduced levels of, gene or genes encoding the enzymatic activity. In particular embodiments, the methods according to this aspect of the invention reduce drug-resistance in tumor cells borne by the cancer patient.

In further embodiments of this aspect of the invention, the methods comprise the steps of: (a) administering to the patient a pharmaceutical composition of the invention comprising an antibody-conjugated enzyme capable of activating a prodrug to a chemotherapeutic drug effective against cancer cells comprising said tumor; and (b) administering the prodrug to the patient, wherein the prodrug is activated by the enzyme inside the cell. In particular embodiments, the pharmaceutical composition comprises an antibody-enzyme conjugate wherein the enzyme is a modified dCK according to the invention. In other particular embodiments, the antibody comprised in the pharmaceutical composition is preferably a monoclonal antibody immunologically specific for a cell surface antigen expressed on the surface of a tumor cell, particularly a tumor cell that expresses, natively or in a chemotherapeutic drug-resistant embodiment thereof, low or reduced levels of dCK activity. In particular embodiments, the prodrug is a nucleoside analog, and preferably the nucleoside analog is a cytidine analog, or a thymidine analog that is activated to an effective chemotherapeutic agent by the modified dCK of the current invention. Most preferably, the thymidine analog is D-dT, L-dT or (E)-5-(2-bromovinyl)-2'-deoxyuridine (BVdU). In certain embodiments, the antibody is capable of being internalized into the interior of the cell expressing the cell surface marker for which the antibody is immunologically specific.

In another aspect, the invention provides modified human dCKs for use in therapies in treating cancer, including without limitation, melanoma, lymphoma, plasmacytoma, sarcoma, glioma, thymoma, leukemia, breast cancer, prostate cancer, colon cancer, esophageal cancer, brain cancer, lung cancer, ovarian cancer, cervical cancer or liver cancer. In particular embodiment, the cancer is leukemia or breast cancer. In certain embodiments of this aspect, the modified human dCKs are conjugated to antibodies, preferably monoclonal antibodies that are immunologically specific for a cell surface antigen expressed on the surface of a tumor cell, particularly a tumor cell that expresses, natively or in a chemotherapeutic drug-resistant embodiment thereof, reduced or absent levels of dCK. In another aspect, the invention provides the use of modified human dCKs in the manufacture of medicaments for the treatment of cancer, preferably leukemia or breast cancer. In yet another aspect, the invention provides the use of modified human dCK-antibody conjugates in the manufacture of medicaments for the treatment of cancer, preferably leukemia or breast cancer.

The reagents, compositions, pharmaceutical compositions and formulations and methods of the invention are advantageous inter alia because they render cells, particularly and specifically tumor cells, sensitive to the cytotoxic or cytostatic effects of nucleoside analog chemotherapy. The invention is advantageous in increasing chemotherapeutic sensitivity of tumor cells to a NA, especially in tumor cells that are natively resistant to the nucleoside analog-based therapies or that have acquired or developed said resistance, because the enzyme activity responsible for converting a nucleoside prodrug such as Ara-C to the triphosphate form is absent or expressed at much reduced levels in said cells. The invention is also advantageous in sensitizing cells to a NA to which the cells normally are not sensitive. The invention is further advantageous because it permits specific accumulation of said nucleoside analogs in targeted cells, wherein embodiments comprising antibody-enzyme conjugates direct the enzyme to cells, most preferably tumor cells, expressing a cell-surface marker recognized by the antibody. In these embodiments, said specifically-targeted cells, preferably tumor cells, exhibit differentially greater enzyme activity than non-targeted, preferably non-tumor, cells. Phosphorylated nucleoside analogs specifically accumulate in said targeted cells as the result of enzyme activity, wherein the triphosphate form of the analog cannot freely exit the cell through the plasma membrane. Thus, the invention advantageously provides a way to target, localize and accumulate chemotherapeutic drugs to the most desired target cells, i.e. tumor cells.

Suitable embodiments of the present invention will become evident from the following more detailed description of certain advantageous embodiments and the claims.

DETAILED DESCRIPTION OF THE INVENTION

This invention provides reagents that are isolated dCK enzymes, preferably human dCK enzymes and more preferably human dCK enzymes comprising genetically-engineered or naturally-occurring mutant species thereof having an increased enzymatic activity and/or additional substrate specificity for converting a prodrug, most preferably an anticancer prodrug into a drug species having a biological, most preferably an anticancer cell effect. Advantageously, the reagents comprise antibody-enzyme conjugates. In particular embodiments, the antibody is capable of being internalized into the interior of the cell expressing the cell surface marker for which the antibody is immunologically specific.

The invention provides reagents comprising dCK variants with altered preferably improved activity and methods of suing such reagents for targeted delivery of an enzyme that can convert a prodrug to a chemotherapeutically-active species thereof in a target cell. Human dCK plays an essential role in the activation of medicinally relevant nucleoside analogs (NAs), such as AraC and gemcitabine, which are extensively used for the treatment of hematological malignancies and some types of solid tumors. In certain specific embodiments, the wild type human dCK comprises the sequence as identified in SEQ ID NO:1; and the modified dCK of the invention comprises specific substitutions at amino acid positions 104, 133 and/or 74 and 100 as described herein. Modified dCKs with conservative amino acid substitutions at positions other than 74, 100, 104 and 133 while retaining dCK activity are also encompassed by the invention.

Figure 1:
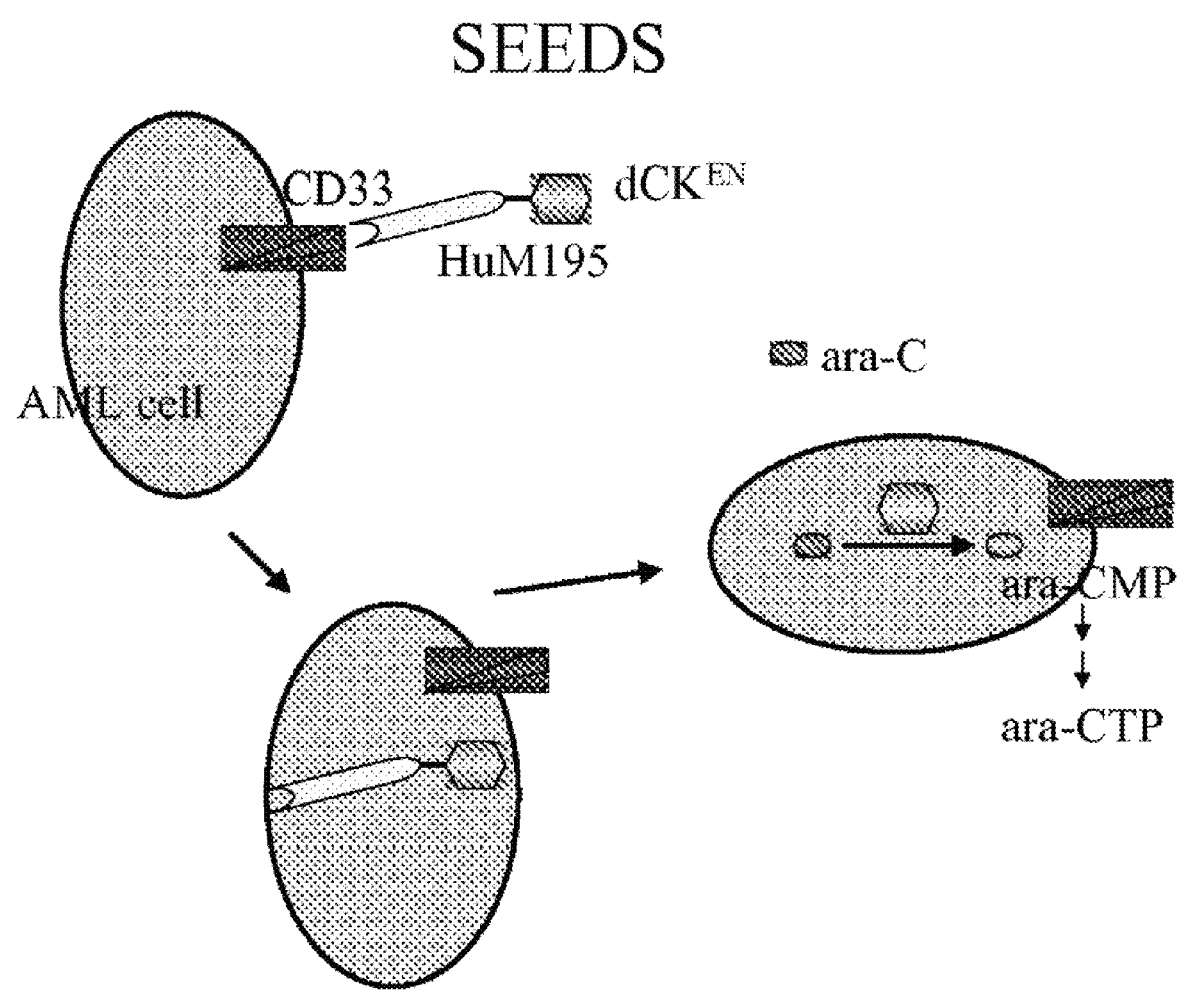
FIG. 1 is a schematic representation of certain aspects of the reagents and methods disclosed herein, termed "selective enhanced enzyme delivery system (SEEDS)".

In one embodiment, a modified dCK of the invention can be used to increase the efficacy of nucleoside analogs, such as AraC or cladribine. Thus, in one aspect, the invention provides a modified, more efficient deoxycytidiune kinase (dCK) that improves and augments the accumulated levels of phosphorylated NAs, such as AraC, in the cells. FIG. 1 shows a schematic diagram of an exemplary embodiment of the invention. In FIG. 1, dCK$^{EN}$ is an engineered form of deoxycytidine kinase (dCK). dCK$^{EN}$ was designed, as described herein, to phosphorylate nucleoside analog drugs, such as AraC and gemcitabine, more efficiently, e.g., at lower extracellular concentrations, or with a greater enzymatic activity. As provided herein, the enzyme is conjugated, most advantageously covalently linked, to an antibody, preferably a monoclonal antibody or immunologically-specific fragment thereof, and in particular embodiments a human or humanized antibody immunologically specific for a cell surface antigen expressed on the cell surface of a eukaryotic cell, specifically a human cell and in particular a human tumor cell. In certain particularly advantageous embodiments, the antibody is capable of being internalized into the interior of the cell expressing the cell surface marker for which the antibody is immunologically specific. Alternatively, the modified dCK can be introduced into target cells by introducing into the cells polynucleotides encoding the modified dCK of the invention using gene delivery techniques known in the art or described herein.

Thus, in one embodiment, the invention provides methods for sensitizing tumor cells that are non-responsive to particular drugs by generating an antibody-conjugated enzyme that will deliver the enzyme to the tumor cells, thereby expressing the enzyme that can activate the particular drug in the cells. A non-responsive cell can be, for example, a cell that normally does not express or expresses an insufficient amount of the necessary enzyme, a cell that expresses a defective or inefficient enzyme, and/or a cell that has acquired resistance to a particular drug (i.e. continues to grow in the presence of a drug that previously diminished or inhibited growth of the cell).

As used herein, a modified dCK having "additional substrate specificity," "extended substrate specificity," "broader substrate specificity," or "a broader spectrum of substrate specificity" refers to a modified dCK that is able to phosphorylate nucleoside analogs or other prodrugs that the wild type dCK is unable to phosphorylate. In one embodiment of the invention, the modified human dCK acquired additional substrate specificity for thymidine and thymidine analogs, such as BVdU. Delivery into tumor cells of such modified human dCK sensitizes the cells to the growth inhibitory effect of thymidine analog prodrugs such as BVdU.

Disclosed herein are particular embodiments of modified human dCK species having increased kinase activity. Those with skill in the art will appreciate that other modified species having increased kinase activity can be produced using the methods disclosed herein, and fall within the scope of the instant disclosure. Included within said modified species are preferably species genetically engineered to have increased activity, but naturally-occurring variants of human dCK are explicitly considered to fall within the scope of the instant disclosure.

The invention provides methods of using such genetically-engineered or naturally-occurring mutant species of human dCK enzymes. In the practice of these methods of this invention, a nucleoside analog prodrug such as AraC is administered to a patient concomitantly with antibody-enzyme conjugate administration. AraC is among the most active agents in treating acute myeloid leukemia (AML) (Estey 2000, *Blood* 96:1670-3). The cytotoxic activity of AraC, however, is dependent on its intracellular conversion to its active metabolite AraCTP. Sampling of blood during and after AraC therapy in patients with AML has illustrated that AraCTP levels are highly relevant to prognosis and response to therapy (Estey et al., 1987, *Leukemia* 1:580-3; Iacoboni et al., 1986, *J. Clin. Oncol.* 4:1079-88). Statistically significant correlations have been reported between response to AraC, and the rate of AraCTP elimination and the area under the curve (AUC) of AraCTP accumulation (Plunkett et al., 1985, *Semin Oncol* 12:20-30; Kantarjian et al., 1986, *Am. J. Med.* 81:387-94). This demonstrates the importance of AraCTP accumulation and retention in treatment outcome. Thus, augmentation of AraCTP levels in leukemia blasts is desirable (Gandhi et al, 1993, *J. Clin. Oncol.* 11:116-24).

Delivery of the enzyme to the interior of the targeted cell provides increased enzymatic activity directly thereto, and accelerates conversion of the prodrug to its monophosphate form inside the cell. It is understood in the art that this monophosphorylation of the prodrug is the rate-limiting step, and that subsequent conversion of the monophosphate form to the triphosphate nucleotide is more efficient in comparison. Thus, the practice of the methods of the invention with these antibody-enzyme conjugates reduces a metabolic bottleneck in the prodrug's activation and facilitates the conversion of NA prodrugs to NA monophosphates, and the increased high concentration of nucleoside analogue NA-triphosphate in the targeted cell results in increased cytotoxicity in the cell.

In certain embodiments, an antibody suitable for use in the invention can be an antibody that is known to recognize antigens specific to a certain cell type including, but not limited to, antibodies described in Sandlie and Brekke (2003, *Nat. Rev. Drug Discovery* 2:52-62). Alternatively, antibodies useful in the invention can be generated to recognize a desired antigen using techniques described herein. In certain aspects of these embodiments, the antibody can internalize or be internalized within the target cell (i.e. enter the target cell through the cell membrane) so that an enzyme conjugated to the antibody is active in the cytoplasm of the target cell. In other aspects, the antibody can bind to a target cell but not internalize, so that a conjugated enzyme is not internalized within the target cell but can activate prodrugs that will enter the target cell in an activated state. In still other aspects, the antibody can be engineered to comprise a Protein Transduction Domain (PTD), which is a short stretch of amino acid residues, mainly basic amino acids such as a polymeric arginine peptide that can carry a protein inside a cell (see, for example, Kabouridis, 2003, *Trends in Biotechnology* 21:498-503). All references cited in this application are expressly incorporated by reference herein for any purpose.

In certain embodiments, an antibody-conjugated enzyme of the invention can be used to target a specific tumor cell that is deficient or lacks an active enzyme necessary for efficient drug activity. For example, a modified species of dCK of the invention can be conjugated to an antibody (such as HERCEPTIN®) that specifically recognizes antigens on a breast tumor cell, which normally does not express dCK. Alternatively, the conjugate specifically targets the tumor cell to provide augmented activity in the cell that expresses normal levels of wild-type dCK. The breast tumor cell can then be contacted with a nucleoside analog, thereby providing an anti-tumor effect on said cell. In particular embodiments, antibody-conjugated enzymes of the invention can be designed to target a particular tumor cell type by choosing an antibody that specifically recognizes antigens on that tumor cell. For example, for prostate cancer, antibodies can be chosen that recognize STEAP (six-transmembrane epithelial antigen of the prostate; Hubert et al., 1999, *Proc Natl Acad Sci USA.* 7:4523-8).

In certain particular embodiments, the antibody is a humanized monoclonal antibody termed HuM195 (Protein Design Laboratories, Fremont, Calif.) that is immunologically specific for cell surface marker protein CD33. CD33 is primarily expressed in acute myelogenous leukemia (AML) cells, and not in normal or stem cells, thus providing targeting specificity to human tumor cells. Accordingly, said embodiments are particularly advantageous for delivering the modified dCK proteins of the invention to human leukemia cells. Importantly, this antibody has the ability to internalize into the cell.

Conventional techniques may be used for recombinant DNA preparation, oligonucleotide synthesis, and in vitro cell and tissue culture and transformation (e.g., electroporation, lipofection). Enzymatic reactions and purification techniques may be performed according to manufacturer's specifications or as commonly accomplished in the art or as described herein. The aforesaid techniques and procedures may be performed according to conventional methods well known in the art and as described in various references cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic DNA, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence. In one aspect, the present invention provides an isolated polynucleotide comprising a nucleotide sequence encoding the modified human deoxycytidine kinase described herein.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially free from proteins or polypeptides or other contaminants that are found in its natural environment that would interfere with its use (therapeutic, diagnostic, prophylactic, research or otherwise).

The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. Thus, a "polypeptide" or a "protein" can comprise one (termed "a monomer") or a plurality (termed "a multimer") of amino acid chains. The terms "polypeptide" and "protein" specifically encompass deoxycytidine kinase (dCK) and modified forms thereof, and particularly genetically-engineered species of dCK produced as disclosed herein, or sequences that have deletions from, additions to, and/or substitutions of one or more amino acid of dCK or a modified dCK of the invention.

The term "polypeptide fragment" refers to a polypeptide, which can be monomeric or multimeric, having an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long; it will be recognized that "peptides" are typically comprise less than about 100 amino acids and "polypeptides" or "proteins" are larger, comprising more than about 100 amino acids. It will be appreciated that in certain embodiments, peptide or polypeptide fragments are at least 5, 6, 8, 10, 14, 20, 50, 70, 100, 110, 150, 200, 250, 300, 350, 400, or 450 amino acids long. Particularly useful polypeptide fragments include functional domains, including binding domains.

The term "naturally-occurring" as used herein and applied to an object refers to the fact that the object can be found in nature. For example, a polypeptide or polynucleotide sequence that is present in an organism (including viruses) that can be isolated from a source in nature and that has not been intentionally modified by man is naturally-occurring.

The term "operably linked" means that the components to which the term is applied are in a relationship that allows them to carry out their inherent functions under suitable conditions. For example, a transcription control sequence "operably linked" to a protein coding sequence is covalently ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as used herein means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "oligonucleotide" referred to herein includes naturally occurring, and modified nucleotides linked together by naturally occurring, and/or non-naturally occurring oligonucleotide linkages. Oligonucleotides are a polynucleotide subset comprising members that are generally single-stranded and have a length of 200 bases or fewer. In certain embodiments, oligonucleotides are 10 to 60 bases in length. In certain embodiments, oligonucleotides are 12, 13, 14, 15, 16, 17, 18, 19, or 20 to 40 bases in length. Oligonucleotides may be single stranded or double stranded, e.g. for use in the construction of a gene mutant. Oligonucleotides of the invention may be sense or antisense oligonucleotides with reference to a protein-coding sequence.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

The term "recombinant expression construct" as used herein is a replicable DNA construct in which a DNA sequence encoding a protein or polypeptide according to the invention is operably linked to suitable control sequences capable of effecting the expression of the protein or polypeptide in a suitable host cell. The need for such control sequences will vary depending upon the host selected and the transformation method chosen. Generally, control sequences include a transcriptional promoter, an optional operator or enhancer sequence to control or regulate transcription, a sequence encoding suitable mRNA ribosomal binding sites, and sequences which control the termination of transcription and translation, and in mammalian cells, sequences that direct 5' terminal capping and 3' terminal polyadenylation of the primary transcript. Amplification vectors, on the other hand, do not require expression control domains. All that is needed is the ability to replicate in a host, usually conferred by an origin of replication, and a selection gene to facilitate recognition of transformants. See, Sambrook et al., 2001, *Molecular Cloning: A Laboratory Manual* (Cold Spring Harbor Press: New York).

The term "host cell" is used to refer to a cell into which has been introduced, or is capable of being introduced with a nucleic acid sequence and further expresses or is capable of expressing a selected gene of interest. The term includes the progeny of the parent cell, whether or not the progeny is identical in morphology or in genetic make-up to the original parent, so long as the selected gene is present.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $\leq 10^{-7}$ or $10^{-8}$ M. In some embodiments, the equilibrium dissociation constant may be $\leq 10^{-9}$ M or $\leq 10^{-10}$ M.

The term "identity," as known in the art, refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is used in the art with regard to a related concept, but in contrast to "identity," "similarity" refers to a measure of relatedness, which includes both identical matches and conservative substitution matches. If two polypeptide sequences have, for example, $^{10}/_{20}$ identical amino acids, and the remainder are all non-conservative substitutions, then the percent identity and similarity would both be 50%. If in the same example, there are five more positions where there are conservative substitutions, then the percent identity remains 50%, but the percent similarity would be 75% ($^{15}/_{20}$). Therefore, in cases where there are conservative substitutions, the percent similarity between two polypeptides will be higher than the percent identity between those two polypeptides. Identity and similarity of related nucleic acids and polypeptides can be readily calculated by methods known in the art. Such methods include, but are not limited to, those described in COMPUTATIONAL MOLECULAR BIOLOGY, (Lesk, ed.), 1988, Oxford University Press, New York; BIOCOMPUTING: INFORMATICS AND GENOME PROJECTS, (Smith, D. W., ed.), 1993, Academic Press, New York; COMPUTER ANALYSIS OF SEQUENCE DATA, Part 1, (Griffin, A. M., and Griffin, H. G., eds.), 1994, Humana Press, New Jersey; von Heinje, G., SEQUENCE ANALYSIS IN MOLECULAR BIOLOGY, 1987, Academic Press; SEQUENCE ANALYSIS PRIMER, (Gribskov and Devereux, eds.), 1991, M. Stockton Press, New York; Carillo et al., 1988, *SIAM J. Applied Math.*, 48:1073; and Durbin et al., 1998, BIOLOGICAL SEQUENCE ANALYSIS, Cambridge University Press.

Exemplary conservative amino acid substitutions are set forth in Table 1. A skilled artisan will be able to determine suitable conservative amino acid substitutions at amino acid position other than the active site of the enzyme without altering the enzymatic activity.

TABLE 1

| Original Residues | Exemplary Substitutions | Preferred Substitutions |
|---|---|---|
| Ala | Val, Leu, Ile | Val |
| Arg | Lys, Gln, Asn | Lys |

TABLE 1-continued

| Original Residues | Exemplary Substitutions | Preferred Substitutions |
|---|---|---|
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

As used herein, the terms "label" or "labeled" refers to incorporation of a detectable marker, e.g., by incorporation of a radiolabeled amino acid, or attachment to a polypeptide or nucleic acid of a fluorescent marker, a chemiluminescent marker or an enzyme having a detectable activity, or attachment to a polypeptide of biotin moieties that can be detected by labeled avidin (e.g., streptavidin preferably comprising a detectable marker such as a fluorescent marker, a chemiluminescent marker or an enzymatic activity that can be detected, inter alia, by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to, the following: radioisotopes or radionuclides (e.g., $^{3}H$, $^{14}C$, $^{15}N$, $^{35}S$, $^{90}Y$, $^{99m}Tc$, $^{111}In$, $^{125}I$, $^{131}I$), fluorescent labels (e.g., fluorescein isothiocyanate or FITC, rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, or epitope tags). In certain embodiments, labels are attached by spacer arms (such as $(CH_2)_n$, where n<about 20) of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "agent" is used herein to denote a chemical compound, a mixture of chemical compounds, a biological macromolecule, or an extract made from biological materials.

The term "pharmaceutical agent or drug" as used herein refers to a chemical compound or composition capable of inducing a desired therapeutic effect when properly administered to a patient.

The term "prodrug," "prodrug to a chemotherapeutic agent" or "chemotherapeutic prodrug" as used herein refers to a nucleoside analog, which upon phosphorylation, converts to a chemotherapeutic agent, particularly a chemotherapeutic agent that inhibits tumor growth.

The term "chemotherapeutic agent," "chemotherapeutic drug," "chemotherapeutically active drug" or "active drug" as used herein refers to an activated or phosphorlylated nucleoside analog. A "nucleoside analog", includes without limitation AraC (1-β-D-arabinofuranosylcytosine; Cytarabine), AraT (1-β-D-arabinofuranosylthymine), dFdC (2',2'-difurodeoxycytidine; Gemcitabine), FaraA (2-fluoro-9-β-D-arabinosyladenine; Fludarabine), ddC (2',3'-dideoxycytidine; Zalcitabine), 3TC (2'-deoxy-3'-thiacytidine; Lamivudine), 2CdA (2-chlorodeoxyadenosine, Cladribine), L-dT (L-deoxythymidine, Telbivudine), L-dU (L-deoxyuridine), or BVdU ((E)-5-(2-bromovinyl)-2'-deoxyuridine).

Treatment of a cancer patient, as described herein, encompasses alleviation of at least one cancer symptom of the cancer, a reduction in cancer severity, or the delay or prevention of progression of the cancer. Treatment need not mean that the cancer is totally cured. A useful therapeutic agent of the invention needs only to reduce the severity of a cancer, reduce the severity of a symptom or symptoms associated with the cancer or its treatment, or provide improvement to a patient's quality of life, or delay or prevent progression of the cancer.

The invention encompasses a method of treating an animal, preferably a human with cancer comprising administering to the cancer patient a modified dCK or an antibody-conjugated dCK of the invention, more preferably a pharmaceutical composition of the invention comprising a modified dCK or an antibody-conjugated dCK of the invention, in an amount and for a time sufficient to induce a sustained improvement, when compared to the patient or tumor before treatment, of an indicator that reflects the severity of a particular cancer or the severity of symptoms caused by the cancer or that delays or prevents progression of the cancer. The invention does not exclude possible treatment with other therapeutic agents before, after, and/or during treatment with the antibody-conjugated enzyme of the invention, a pharmaceutical composition of the invention, or a modified deoxycytidine kinase (dCK) of the invention.

As used herein, the term "substantially pure" or "substantially purified" means a compound or species that is the predominant species present (i.e., on a molar basis it is more abundant than any other individual species in the composition). In certain embodiments, a substantially purified fraction is a composition wherein the species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

The term "patient" as used herein includes human and animal subjects, but human patients are preferred, and most preferred are human cancer patients.

Unless otherwise required by context, singular terms shall include pluralities.

As used herein, the term "antibody" or "antibody peptide(s)" refers to a monomeric or multimeric protein comprising one or more polypeptide chains. An antibody can bind specifically to an antigen and may be able to inhibit or modulate the biological activity of the antigen. "Antibodies" include naturally occurring antibodies, which are described below. In certain embodiments, antibodies are produced by recombinant DNA techniques. In additional embodiments, the term "antibodies" encompasses fragments of naturally-occurring or synthetic antibodies that are produced by enzymatic or chemical cleavage of naturally occurring antibodies. Antibody fragments include, but are not limited to, F(ab), F(ab'), F(ab')$_2$, Fv, and single chain Fv fragments. Antibodies and antibody fragments as these terms are used herein also include single-chain, chimeric, humanized, fully human, polyclonal, and monoclonal antibodies. At a minimum, an antibody, as meant herein, comprises a polypeptide that can bind specifically to an antigen wherein the antibody comprises all or part of a light or heavy chain variable region. The techniques of preparing and using antibodies are well known in the art and are generally provided in commonly used reference books, for example, ANTIBODIES: A LABORATORY MANUAL, Harlow and Lane (eds.), Cold Spring Harbor Laboratory Press, 1988).

A variable region comprises at least three heavy or light chain complementarity determining regions (CDRs, also known as hypervariable regions, designated CDR1, CDR2, and CDR3 by Kabat et al., 1991, SEQUENCES OF PROTEINS OF IMMUNOLOGICAL INTEREST, Public Health Service N.I.H., Bethesda, Md.; see also Chothia and Lesk, 1987, *J. Mol. Biol.* 196: 901-17; Chothia et al., 1989, *Nature* 342: 877-83) embedded within a framework region (designated framework regions 1-4, FR1, FR2, FR3, and FR4, by Kabat et al., supra; see also Chothia and Lesk, supra). The CDRs and the framework segments are interspersed as follows, starting at the amino terminus of the variable region: FR1-CDR1-FR2-CDR2-FR3-CDR3-FR4.

The term "heavy chain" includes any immunoglobulin polypeptide having sufficient variable region sequence to confer binding specificity for a particular antigen. The term "light chain" includes any immunoglobulin polypeptide having sufficient variable region sequence to confer binding specificity for a particular antigen. Such a heavy or light chain may, but need not, bind to an antigen in the absence of a light chain, if it is a heavy chain, or a heavy chain, if it is a light chain. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxyl-terminus. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof. An F(ab) fragment is comprised of one light chain and the $C_H1$ and variable regions of one heavy chain. The heavy chain of an F(ab) molecule cannot form a disulfide bond with another heavy chain molecule. An F(ab') fragment contains one light chain and one heavy chain that contains more of the constant region, between the $C_H1$ and $C_H2$ domains, such that an interchain disulfide bond can be formed between two heavy chains to form an F(ab')$_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203. In certain embodiments, the invention provides conjugates of enzymes with F(ab), F(ab'), F(ab')$_2$, single-chain variable fragments, or other antibody fragments that specifically bind to the target antigens.

As used herein, the term "fully human antibodies" comprise amino acid sequences encoded only by polynucleotides that are ultimately of human origin or amino acid sequences that are identical to such sequences. For example, inter alia, antibodies encoded by human immunoglobulin-encoding DNA inserted into a mouse genome produced in a transgenic mouse are fully human antibodies since they are encoded by DNA that is ultimately of human origin. In this situation, human immunoglobulin-encoding DNA can be rearranged (to encode an antibody) within the mouse, and somatic mutations may also occur. Antibodies encoded by originally human DNA that has undergone such changes in a mouse are fully human antibodies as the term is used herein. The use of such transgenic mice makes it possible to select fully human antibodies against a human antigen. One of skill in the art will appreciate that fully human antibodies are advantageous for use as therapeutics, particularly to treat chronic diseases, since they are unlikely to precipitate an immune response against themselves. In contrast, many non-human antibodies are known to precipitate an immune response against themselves when used in humans, a situation that makes chronic use of such antibodies in humans inadvisable. Fully human antibodies thus solve a long-standing problem faced in using antibodies to treat chronic conditions, including human diseases. See e.g. Billiau, 1988, *Immunol. Today* 9:37-40; Horneff et al., 1991, *Clin. Immunol. & Immunopathol.* 59:89-103; Tjandra et al., 1990, *Immunol & Cell Biol.* 68:367-76.

In a humanized antibody, the entire antibody, except the CDRs, is encoded by a polynucleotide of human origin or is identical to such an antibody except within its CDRs. The CDRs, which are encoded by nucleic acids originating in a non-human organism, are grafted into the β-sheet framework of a human antibody variable region to create an antibody, the specificity of which is determined by the engrafted CDRs. The creation of such antibodies is described in, e.g., WO 92/11018, Jones et al., 1986, *Nature* 321:522-25, Verhoeyen et al., 1988, *Science* 239:1534-36. In contrast, a chimeric antibody comprises a human constant region (which is encoded by a polynucleotide of human origin or is identical to such a human constant region) and a non-human variable region. The creation of such antibodies is described in, e.g., U.S. Pat. No. 5,681,722.

A bivalent antibody other than a "multispecific" or "multifunctional" antibody, in certain embodiments, is understood to comprise binding sites having identical antigenic specificity. A bispecific or bifunctional antibody typically is an artificial hybrid antibody having two different heavy chain/light chain pairs and two different binding sites. Bispecific antibodies may be produced by a variety of methods including, but not limited to, fusion of hybridomas or linking of F(ab') fragments. See, e.g., Songsivilai & Lachmann, 1990, *Clin. Exp. Immunol.* 79: 315-321; Kostelny et al., 1992, *J. Immunol.* 148:1547-1553.

In additional embodiments, antibody variants can include antibodies comprising a modified Fc fragment or a modified heavy chain constant region. An Fc fragment or a heavy chain constant region can be modified by mutation to confer on an antibody altered characteristics. See, for example, Burton and Woof, 1992, *Advances in Immunology* 51: 1-84; Ravetch and Bolland, 2001, *Annu. Rev. Immunol.* 19: 275-90; Shields et al., 2001, *Journal of Biol. Chem.* 276: 6591-6604; Telleman and Junghans, 2000, *Immunology* 100: 245-251; Medesan et al., 1998, *Eur. J. Immunol.* 28: 2092-2100; all of which are incorporated herein by reference). Such mutations can include substitutions, additions, deletions, or any combination thereof, and are typically produced by site-directed mutagenesis using one or more mutagenic oligonucleotide(s) according to methods described herein, as well as according to methods known in the art (see, for example, Maniatis et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

Additional antibody variants include cysteine variants wherein one or more cysteine residues are deleted from or substituted for another amino acid (e.g., serine) compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Antibodies can be matured in vitro to produce antibodies with altered properties, such as a higher affinity for an antigen or a lower dissociation constant. Variation of only residues within the complementarity determining regions (CDRs), particularly the CDR3s, can result in altered antibodies that bind to the same antigen, but with greater affinity. See e.g. Schier et al., 1996, *J. Mol. Biol.* 263:551-67; Yang et al., 1995, *J. Mol. Biol.* 254:392-403. The invention encompasses antibodies created by a variety of in vitro selection schemes, such as affinity maturation and/or chain shuffling (Kang et al., 1991, *Proc. Natl. Acad. Sci.* 88:11120-23), or DNA shuffling (Stemmer, 1994, *Nature* 370:389-391), by which antibodies may be selected to have advantageous properties. In many schemes, a known antibody is randomized at certain positions, often within the CDRs, in vitro and subjected to a selection process whereby antibodies with desired properties, such as increased affinity for a certain antigen, can be isolated. See e.g. van den Beucken et al., 2001, *J. Mol. Biol.* 310:591-601; Desiderio et al., 2001, *J. Mol. Biol.* 310:603-15; Yang et al., 1995, *J. Mol. Biol.* 254:392-403; Schier et al., 1996, *J. Mol. Biol.* 263:551-67. Typically, such mutated antibodies may comprise several altered residues in one or more CDRs, depending on the design of the mutagenesis and selection steps. See e.g. van den Beucken et al., supra.

Preferred antibodies of the invention are specific for antigens present on the cell surface of target cells, most preferably tumor cells. Most preferred embodiments of said antibodies are not immunogenic, and are capable of being internalized within the target tumor cells. The antibodies chosen for conjugation to a particular enzyme will depend on the type of cancer cell that is to be targeted. Said antibodies are preferably conjugated to an enzyme that catalyzes production of a biologically-active drug from a prodrug having reduced or little activity compare with the active drug. In certain embodiments of this invention, the antibodies are conjugated to deoxycytidine kinase (dCK), more preferably human dCK and most preferably modified human deoxycytidine kinase as disclosed herein. Antibodies used in such conjugates most preferably are effectively internalized within a targeted cell. Such antibodies are known, such as HuM195 used in acute myelogenous leukaemia (AML) therapy and BL22 used in therapy of B-cell malignancies (Caron et al., 1992, *Cancer Res.* 52:6761-7; Appelbaum, 1999, *Semin Hematol* 36:2-8). Alternatively, such antibodies can be designed to identify specific cells.

In a particular embodiment, the invention provides covalent conjugates of a humanized anti-CD33 monoclonal antibody, which can be used to target leukemia blast cells, most preferably acute myelogenous leukaemia blast cells. In additional embodiments, the invention provides antibody-conjugated enzymes that can target any tumor cell by choosing an antibody that will bind to antigens on that tumor cell. For example, in addition to anti-CD33 antibodies for leukaemia cells, anti-CD20 (such as RITUXAN®) antibodies can be used to target tumor cells of Non-Hodgkin's lymphoma, HERCEPTIN® antibodies can be used to target breast tumor cells, and anti-CC49 antibodies (such as B72.3) can be used to target colorectal, ovarian, and breast tumor cells. Non-limiting examples of these and additional antibodies useful for designing antibody-conjugated enzymes of the invention are described in Sandlie and Brekke (2003, *Nat. Rev. Drug Discovery* 2:52-62). In particularly advantageous embodiments, antibody-conjugated enzymes according to the invention are effectively delivered into a targeted cell.

Antibodies of the invention can be polyclonal or monoclonal and/or may be recombinant antibodies. In certain embodiments, fully human antibodies of the invention are prepared, for example, by immunization of transgenic animals capable of producing human antibodies (see, for example, International Patent Application, Publication WO 93/12227).

Antibodies of the invention can be prepared using transgenic mice that have a substantial portion of the human antibody producing locus inserted in antibody-producing cells of the mice, and that are further engineered to be deficient in producing endogenous, murine, antibodies. Such mice are capable of producing human immunoglobulin molecules and antibodies and do not produce or produce substantially reduced amounts of murine immunoglobulin molecules and antibodies. Technologies utilized for achieving this result are disclosed in the patents, applications, and references disclosed in the specification herein. In certain embodiments, the skilled worker may employ methods as disclosed in International Patent Application Publication No. WO 98/24893, which is hereby incorporated by reference for any purpose. See also Mendez et al., 1997, *Nature Genetics* 15:146-156, which is hereby incorporated by reference for any purpose. The human antibody repertoire in these mouse strains yields high affinity antibodies against any antigens of interest, including human antigens. Using the hybridoma technology, antigen-specific human monoclonal antibodies with the desired specificity can be produced and selected.

The monoclonal antibodies (mAbs) of the invention can be produced by a variety of techniques, including conventional monoclonal antibody methodology, e.g., the standard somatic cell hybridization technique of Kohler and Milstein (1975, *Nature* 256:495). Although somatic cell hybridization procedures are preferred, in principle, other techniques for producing monoclonal antibodies can be employed, e.g., viral or oncogenic transformation of B-lymphocytes. A conventional animal system useful for preparing hybridomas is the mouse. Hybridoma production in the mouse is very well established, and immunization protocols and techniques for isolation of immunized splenocytes for fusion are well known in the art. Fusion partners (e.g., murine myeloma cells) and fusion procedures are also known.

In certain embodiments, conservative modifications to the heavy chains and light chains of an antibody suitable for use in the invention (and corresponding modifications to the encoding nucleotides) can produce antibodies having functional and chemical characteristics similar to those of the wild type antibody. In contrast, substantial modifications in the functional and/or chemical characteristics of an antibody may be accomplished by selecting substitutions in the amino acid sequence of the heavy and light chains that differ significantly in their effect on maintaining (a) the structure of the molecular backbone in the area of the substitution, for example, as a β sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position.

Conjugation of an antibody to an enzyme can be accomplished using techniques as described in the Examples below.

The structures of human dCK in complex with dC-ADP, ara-C-ADP.Mg, and gemcitabine-ADP.Mg have been determined and are described herein. These structures were advantageously used to elucidate the structures of the human dCK enzyme and phosphorylation kinetics observed with various cytosine-analogs and suggested specific modifications to the current arsenal of prodrugs that may improve phosphorylation by dCK, thereby providing an improved therapeutic index. Further, the dCK complexes described herein provide a starting point for structure-based design of mutant dCK enzymes with enhanced activity or additional substrate specificity, which can be used, for example, in gene therapy applications.

In one aspect, the invention provides a dCK mutant having equal or greater catalytic activity than naturally-occurring wild type enzyme. In another aspect, the invention provides modified dCK that acquired substrate specificity, especially specificity for thymidine, that is absent in the naturally-occurring wild type dCK. In a further aspect, the invention provides methods for treating tumor cell comprising contacting the tumor cell with a thymidine analog and the modified dCK of the invention, preferably the antibody conjugated-modified dCK, that phosphorylates the thymidine analog once inside the cell.

Described in co-owned U.S. patent application Ser. No. 10/791,155 (now issued U.S. Pat. No. 7,419,811) and Ser. No. 11/760,399 (published as U.S. Patent Application Publication No. 20070258968) are dCK mutants having R104M/D133A substitutions or A100V/R104M/D133A substitutions. Both mutant dCKs exhibited additional substrate specificity for thymidine. The disclosures of U.S. Pat. No. 7,419,811 and U.S. Patent Application Publication No. 20070258968 are herein incorporated by reference in their entireties.

It was unexpectedly discovered in the instant application that mutant dCK of the invention with substitutions at positions 104 and 133 with amino acids other than those described in U.S. Pat. No. 7,419,811 and U.S. Patent Application Publication No. 20070258968 also acquired enhanced activity towards nucleoside analogs as compared to wild type dCK. Particular embodiments of the modified dCK enzymes of the invention include mutants wherein the substitution at amino acid position 104 is glutamine, asparagine, valine, phenylalanine, methionine, isoleucine, leucine, lysine, or histidine, more preferably glutamine, leucine, isoleucine, valine, or phenylalanine, and most preferably glutamine, leucine, or isoleucine, and wherein the substitution at amino acid position 133 is alanine, glycine, valine, methionine, threonine, serine, isoleucine, leucine, glutamine, asparagine, or histidine, more preferably alanine, valine, methionine, isoleucine, leucine, or glutamine, and most preferably alanine In further particular embodiments, the modified dCK of the invention comprises additional mutations at amino acid positions 74 and/or 100, wherein the substitution at amino acid position 74 is preferably glutamic acid, and the substitution at amino acid position 100 is glycine, valine, isoleucine, leucine, threonine, or proline, more preferably valine, isoleucine, or leucine, and most preferably valine.

It was further surprisingly discovered that modified dCKs with substitutions other than methionine at position 104 exhibited unique characteristics. For example, while both dCK R104M/D133A and dCK R104L/D133A exhibited superior activity than wild-type dCK with D-dC or D-dT as the substrate, the R104L/D133A variant showed higher activities than the R104M/D133A variant with a purine substrate, such as D-dG and D-dA. Further, the R104L/D133A variant showed higher efficiency (as defined by $k_{cat}/K_m$) than the R104M/D133A variant with a thymidine substrate, such as D-dT and L-dT (see Table 9).

Modified human dCKs with conservative amino acid substitutions at positions other than 74, 100, 104, and 133 or other active sites of the enzyme while retaining dCK activity are also encompassed within the scope of the invention. What constitutes a conservative amino acid substitution is well understood by one of ordinary skill in the art, and is further described in Table 1.

The structural information provided herein can be used to design additional dCK mutants with enhanced activity towards clinically important nucleoside analogs (NAs), which can be used in modulating conventional chemotherapy. Hematopoietic progenitor cell assays as disclosed herein can be used to examine the effect of such modified dCK mutants on the cytotoxicity of NAs such as AraC or BVdU.

Nucleic acid molecules (or polynucleotides) encoding the amino acid sequence of deoxycytidine kinase (dCK) or a modified dCK that has a better catalytic efficiency and/or a broader substrate specificity than wild type dCK are encompassed by the invention. Such polynucleotides can be inserted into an appropriate expression vector using conventional recombinant genetic techniques. The vector is typically selected to be functional in the particular host cell employed (i.e., the vector is compatible with the host cell machinery such that amplification of the gene and/or expression of the gene can occur). For a review of expression vectors, see METH. ENZ. 185 (Goeddel, ed.), 1990, Academic Press.

The invention also provides expression vectors comprising polynucleotides encoding the modified dCK as described herein. Typically, recombinant expression constructs comprising expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a sequence encoding an epitope tag, a ribosome binding site, a polyadenylation sequence, a polylinker region for inserting the nucleic acid encoding the polypeptide to be expressed, and a selectable marker element. Each of these sequences is discussed below.

Optionally, the construct may contain a "tag"-encoding sequence, i.e., an oligonucleotide molecule located at the 5' or 3' end of a modified dCK polypeptide coding sequence; the oligonucleotide sequence encodes polyHis (such as hexa-His), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the dCK or modified dCK of the invention from the host cell. Affinity purification can be accomplished, for example, by column chromatography using antibodies against the tag as an affinity matrix. Optionally, the tag can subsequently be removed from the purified dCK or modified dCK polypeptide by various means such as using certain peptidases for cleavage. For example, human dCK can be tagged with a His tag, which can be cleaved with thrombin.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the constructs provided by the invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of commercially-available prokaryotic expression vectors, and is useful for amplifying the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Preferred selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as dCK or a modified species of dCK polypeptide. As a result, increased quantities of a polypeptide such as dCK or a modified dCK polypeptide species are synthesized from the amplified DNA.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors comprising the recombinant expression constructs of the invention will typically contain a promoter that is recognized by the host organism and operably linked to the molecule encoding dCK or a modified dCK polypeptide species. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe genes to which they are operably linked, that is, with little or no control over regulation of gene expression. A large number of promoters, recognized by a variety of potential host cells, are well known. A suitable promoter is operably linked to the DNA encoding heavy chain or light chain comprising dCK or a modified dCK polypeptide of the invention by removing the promoter from the source DNA by restriction enzyme digestion and inserting the desired promoter sequence into the vector.

Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-10); CMV promoter (Thomsen et al., 1984, *Proc. Natl. Acad. USA* 81:659-663); the promoter contained in the 3' long terminal repeat of Rous sarcoma virus (Yamamoto, et al., 1980, *Cell* 22:787-97); herpes thymidine kinase promoter (Wagner et al., 1981, *Proc. Natl. Acad. Sci. U.S.A.* 78:1444-45); promoter and regulatory sequences from the metallothionine gene (Brinster et al., 1982, *Nature* 296: 39-42); and prokaryotic promoters such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region that is active in pancreatic beta cells (Hanahan, 1985, *Nature* 315:115-22); the immunoglobulin gene control region that is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region that is active in testicular, breast, lymphoid and mast cells (Leder et al., 1986, *Cell* 45:485-95); the albumin gene control region that is active in liver (Pinkert et al., 1987, *Genes and Devel.* 1:268-76); the alpha-feto-protein gene control region that is active in liver (Krumlauf et al., 1985, *Mol. Cell. Biol.*, 5:1639-48; Hammer et al., 1987, *Science* 235:53-58); the alpha 1-antitrypsin gene control region that is active in liver (Kelsey et al., 1987, *Genes and Devel.* 1:161-71); the beta-globin gene control region that is active in myeloid cells (Mogram et al., 1985, *Nature* 315:338-40; Kollias et al., 1986, *Cell* 46:89-94); the myelin basic protein gene control region that is active in oligodendrocyte cells in the brain (Readhead et al., 1987, *Cell* 48:703-12); the myosin light chain-2 gene control region that is active in skeletal muscle (Sani, 1985, *Nature* 314:283-86); and the gonadotropic releasing hormone gene control region that is active in the hypothalamus (Mason et al., 1986, *Science* 234:1372-78).

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

An enhancer sequence may be inserted into the vector to increase transcription of DNA encoding dCK or a modified dCK polypeptide of the invention by higher eukaryotes. Enhancers are cis-acting elements of DNA, usually about 10-300 by in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter.

Recombinant expression constructs of the invention may be produced from a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

In another aspect, the invention provides host cells that produce the modified dCKs. After the recombinant expression construct has been produced and a nucleic acid molecule encoding a dCK or a modified dCK polypeptide has been inserted into the proper site of the vector, the completed construct is advantageously inserted into a suitable host cell for amplification and/or polypeptide expression. The transformation of an expression vector for a dCK or a modified dCK polypeptide into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

A sequence encoding an appropriate native or heterologous signal sequence (leader sequence or signal peptide) can be incorporated into an expression vector, to promote extracellular secretion of the polypeptide. The choice of signal peptide or leader depends on the type of host cells in which the polypeptide is produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al. (1984, *Nature* 312: 768); the interleukin-4 receptor signal peptide described in EP Patent No. 0 367 566; the type I interleukin-1 receptor signal peptide described in U.S. Pat. No. 4,968,607; the type II interleukin-1 receptor signal peptide described in EP Patent No. 0 460 846.

A host cell, when cultured under appropriate conditions, will synthesize dCK or a modified dCK polypeptide that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. In addition, dCK can be expressed in a bacterial expression system using, for example, BL21(DE3) competent cells.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produced a dCK or a modified dCK polypeptide. In another embodiment, a cell line from the B cell lineage that does not make its own antibody but has a capacity to make and secrete a heterologous antibody can be selected.

In some embodiments, the invention provides compositions comprising a modified dCK or an antibody-conjugated dCK. In certain particular embodiments, the composition is a pharmaceutical composition comprising a therapeutically effective amount of one or a plurality of the antibody-enzyme conjugates of the invention together with a pharmaceutically acceptable diluent, carrier, solubilizer, emulsifier, preservative, and/or adjuvant. Preferably, acceptable formulation materials are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition, without affecting the enzymatic activity of the modified dCK. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18$^{th}$ Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In particular embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, pharmaceutical compositions, antibody-conjugated enzymes, and/or modified enzymes of the invention, may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, dCK or modified dCK polypeptide or an antibody-conjugated enzyme of the invention may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired modified dCK polypeptide or an antibody-conjugated enzyme of the invention in a pharmaceutically acceptable vehicle. A particularly suitable vehicle for parenteral injection is sterile distilled water in which the modified dCK polypeptide or an antibody-conjugated enzyme of the invention is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, modified dCK polypeptide or an antibody-conjugated enzyme of the invention are advantageously formulated as a dry, inhalable powder. In particular embodiments, modified dCK polypeptide or antibody-conjugated enzyme inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Modified dCK polypeptides or antibody-conjugated enzymes of the invention that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the modified dCK polypeptide or an antibody-conjugated enzyme of the invention. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of modified dCK polypeptides or antibody-conjugated enzymes of the invention in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving modified dCK polypeptides or antibody-conjugated enzymes of the invention in sustained- or controlled-delivery formulations. Techniques for formulating a variety of other sustained- or controlled-delivery means, such as liposome carriers, bioerodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 22:547-556), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(-)-3-hydroxybutyric acid (European Patent Application Publication No. EP 133,988). Sustained release compositions may also include liposomes that can be prepared by any of several methods known in the art. See e.g., Eppstein et al., 1985, *Proc. Natl. Acad. Sci. USA* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation, and optionally instructions for use. In certain embodiments of this invention, kits containing single and multi-chambered pre-filled syringes (e.g., liquid syringes and lyosyringes) are provided.

The therapeutically effective amount of a modified dCK polypeptide- or an antibody-conjugated enzyme of the invention-containing pharmaceutical composition to be employed will depend, for example, upon the therapeutic context and objectives. One skilled in the art will appreciate that the appropriate dosage levels for treatment will vary depending, in part, upon the molecule delivered, the indication for which the modified dCK polypeptide or an antibody-conjugated enzyme of the invention is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In particular embodiments, the dosage may range from 0.1 µg/kg up to about 30 mg/kg, optionally from 1 µg/kg up to about 30 mg/kg or from 10 µg/kg up to about 5 mg/kg.

It will be recognized by one of skill in the art that the amount of drug required for therapeutic effect on administration will, of course, vary with the agent chosen, the nature and severity of the condition and the mammal undergoing treatment, and is ultimately at the discretion of the physician. It will also be appreciated that the optimal course of treatment and the number of doses given, can be ascertained by those skilled in the art using conventional course of treatment determination tests.

Dosing frequency will depend upon the pharmacokinetic parameters of the particular modified dCK polypeptide or antibody-conjugated enzyme of the invention in the formulation used. Typically, a clinician administers the composition until a dosage is reached that achieves the desired effect. The composition may therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, the antibodies of the invention can be administered to patients throughout an extended time period. Chronic administration of an antibody-modified dCK conjugate of the invention minimizes the adverse immune or allergic response commonly associated with antibodies that are raised against a human antigen in a non-human animal, for example, a non-fully human antibody or non-human antibody produced in a non-human species.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use pharmaceutical compositions of the invention according to the invention ex vivo. In such instances, cells, tissues or organs that have been removed from the patient are exposed to pharmaceutical compositions of the invention after which the cells, tissues and/or organs are subsequently implanted back into the patient.

In particular, modified dCK polypeptides or antibody-conjugated enzymes of the invention can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

The Examples, which follow, are illustrative of specific embodiments of the invention, and various uses thereof. They are set forth for explanatory purposes only, and are not to be taken as limiting the invention.

EXAMPLES

Example 1

Crystallization of Human Deoxycytidine Kinase (dCK)

Human dCK was amplified from a cDNA library (Invitrogen, Carlsbad, Calif.) and cloned into the pET14b vector as described in U.S. Pat. No. 7,419,811 and U.S. Patent Application Publication No. 20070258968, the disclosures of both of which are herein incorporated by reference in their entireties. Primer oligonucleotides (forward primer SEQ ID NO:22, reverse primer SEQ ID NO:23) were designed based on the published DNA sequence, introducing suitable endonuclease restriction sites at either end to facilitate direct cloning into the pET14b bacterial expression vector (available from, for example, Novagen, San Diego, Calif.). Clone integrity was verified by automated DNA sequencing. The cDNA sequence of human dCK is shown in GenBank Accession No. NM_000788.2 (SEQ ID NO:21). BL21(DE3) *E. coli* (available from, for example, Strategene, La Jolla, Calif.) carrying the recombinant plasmid coding for histidine-tagged dCK was grown in 2YT media at 37° C., induced with 0.1 mM isopropyl-beta-D-thiogalactopyranoside (IPTG) and harvested after 8 hours. The cell pellet was lysed by sonication, and loaded on a TALON $Co^{2+}$-affinity column (Clontech, Palo Alto, Calif.). After washing and elution with imidazole, the His-tag was cleaved by thrombin. The protein was further purified on an ion-exchange column and a gel filtration column (S-200). Selenomethionine-substituted protein was produced by following an established protocol (Doublie, 1997, *Methods Enzymol.* 276:523-30).

Crystals of human dCK in complex with nucleosides and nucleotides (dC and ADP, ara-C and ADP, gemcitabine and ADP) were grown by the vapor diffusion method using either the sitting-drop or the hanging-drop geometry. Nucleotides were from Sigma (St. Louis, Mo.) except for gemcitabine, which was a gift from Eli Lilly & Co (Indianapolis, Ind.). After formation of the respective complex by mixing dC (or ara-C or gemcitabine) together with ADP (final concentration of 5 mM each) and the dialyzed enzyme solution (12 mg ml$^{-1}$ dCK, 5 mM $MgCl_2$, 20 mM Hepes, pH 7.5, 5 mM DTT, 100 µM dC/ara-C/gemcitabine), 2 µl of the premixed solution were added to 2 µl of the reservoir solution and left to equilibrate at 20° C. against the reservoir. Tetragonal crystals were obtained from sitting-drops using a reservoir solution that contained 0.95-1.0 M citrate trisodium dihydrate and 100 mM Hepes, pH 7.5, or from hanging-drops using 20% (w/v) PEG1K, 100 mM magnesium acetate, and 100 mM Tris, pH 9.0. At times, the citrate condition also gave orthogonal crystals. Typically, crystals grew within one week to dimensions of 200×100×100 µm$^3$.

Crystals were transferred to a cryoprotectant solution that in the case of the citrate condition was made of mineral oil (Sigma) while for the crystals grown in PEG it was composed of the mother liquor and 10% (w/v) xylitol-10% (w/v) sucrose. Once the crystals were mounted in loops, they were frozen by directly immersing them in liquid nitrogen. X-ray data were collected at the Advanced Photon Source using the BioCARS beamlines BM-C and BM-D, and the SERCAT beamline ID-22. The data were indexed, scaled and merged using the programs XDS and XSCALE (Kabsch, 1993, *J. Appl. Crystal* 24:795-800) or Denzo and Scalepack (Otwinowski and Minor, 1997, *Methods Enzymol.* 276:307-326). Data collection statistics for all data sets are shown in Table 2.

TABLE 2

| | Data collection, phasing, and refinement statistics | | | | | |
|---|---|---|---|---|---|---|
| | MAD | | | dC-ADP | dC-ADP | Ara-C-ADP-Mg | gemcitabine-ADP-Mg |
| | Data collection statistics | | | | | | |
| Beamline | | 14-BM-D | | 14-BM-C | 14-BM-C | 22-ID | 22-ID |
| Wavelength (Å) | 0.97997 | 0.97973 | 0.95705 | 0.9 | 0.9 | 1.0 | 1.0 |
| Temperature (K) | | 100 | | 100 | 100 | 100 | 100 |
| Resolution (Å) | | 2.3 | | 1.96 | 2.2 | 1.6 | 1.9 |
| Observed reflections | 257787 | 257933 | 258286 | 270973 | 219344 | 487680 | 326066 |
| Unique reflections | 24032 | 23928 | 24055 | 39237 | 15406 | 41313 | 27499 |

TABLE 2-continued

Data collection, phasing, and refinement statistics

|  | MAD | | | dC-ADP | dC-ADP | Ara-C-ADP-Mg | gemcitabine-ADP-Mg |
|---|---|---|---|---|---|---|---|
| Completeness (%, overall/last shell) | 94.5 (64.0) | 94.0 (61.8) | 94.6 (64.8) | 97.4 (67.8) | 95.9 (78.2) | 99.0 (99.6) | 99.5 (99.4) |
|  |  |  |  | (1.96-2.0 Å) | (2.2-2.3 Å) | (1.6-1.7 Å) | (1.9-1.95 Å) |
| Rsym (%, overall/last shell) | 4.5 (31.1) | 4.7 (32.1) | 4.6 (33.1) | 4.5 (29.1) | 6.4 (15.6) | 5.2 (51.1) | 5.4 (53.3) |
| I/σ(I) (overall/last shell) | 29.5 (3.3) | 27.8 (3.1) | 28.9 (2.8) | 23.7 (3.3) | 28.2 (7.5) | 23.1 (4.9) | 24.2 (4.7) |
| Space group |  | $P4_32_12$ |  | $C222_1$ | $P4_32_12$ | $P4_32_12$ | $P4_32_12$ |
| Unit cell (Å) |  |  |  |  |  |  |  |
| a= |  | 79.64 |  | 52.74 | 80.00 | 80.72 | 80.20 |
| b= |  | 79.64 |  | 132.92 | 80.00 | 80.72 | 80.20 |
| c= |  | 93.71 |  | 157.64 | 93.95 | 94.28 | 94.60 |
| Molecules per au |  | 1 |  | 2 | 1 | 1 | 1 |
|  | Phasing statistics | | | | | | |
| Heavy atom sites (Se) |  | 4 |  |  |  |  |  |
| Figure of Merit |  | 0.54 |  |  |  |  |  |
|  |  |  |  | Refinement statistics | | | |
| $R_{factor}/R_{free}$ (%) |  |  |  | 16.1/20.3 | 22.1/28.0 | 17.3/19.7 | 17.9/20.7 |
| Resolution range (Å) |  |  |  | 20-1.96 | 20-2.2 | 20-1.6 | 20-1.9 |
| No. of atoms/molecules |  |  |  |  |  |  |  |
| protein |  |  |  | (A) 1990 (B) 1830 | 1869 | 1982 | 1892 |
| nucleoside |  |  |  | 16 × 2 | 16 | 17 | 18 |
| ADP |  |  |  | 27 × 2 | 27 | 27 | 27 |
| waters |  |  |  | 333 | 131 | 173 | 141 |
| R.m.s. deviation |  |  |  |  |  |  |  |
| bond length (Å) |  |  |  | 0.020 | 0.021 | 0.018 | 0.021 |
| bond angles (Å) |  |  |  | 1.922 | 1.885 | 1.770 | 1.966 |
| Average B-factor (Å$^2$) |  |  |  |  |  |  |  |
| protein (main chain) |  |  |  | (A) 27 (B) 28 | 43 | 27 | 34 |
| protein (side chain) |  |  |  | (A) 29 (B) 31 | 44 | 30 | 37 |
| ADP |  |  |  | (A) 22 (B) 23 | 37 | 22 | 30 |
| nucleoside |  |  |  | (A) 20 (B) 22 | 33 | 20 | 26 |
| waters |  |  |  | 37 | 47 | 37 | 41 |

Structure Determination and Refinement

The structure of human dCK was solved using the Multi-wavelength Anomalous Dispersion (MAD) method (Hendrickson and Ogata, 1997, *Methods Enzymol.* 276:494-523). Using data from the inflection, the peak, and the remote wavelengths, 4 selenium atoms were located using SOLVE (Terwilliger, 1999, *Acta Cryst.* D55:1863-1871). The map calculated from the experimental phases enabled the generation of a model of dCK in O (Jones et al., 1991, *Acta Cryst.* A47:110-119). Refinement was carried out using the programs CNS (Brünger, 1993, *X-PLOR: a system for X-ray crystallography and NMR*, Yale University Press, New Haven, Conn.) and REFMAC (Murshudov et al., 1997, *Acta Cryst.* D53:240-255). Data for the MAD data set were collected to 2.3 Å resolution. A partially built model into the MAD electron density was used to solve the tetragonal crystals. The electron density for dCK extended to the last residue (Leu260), while the N-terminus (residues 1 to 19) was flexible and could not be modeled. Deoxycytidine and ADP were modeled in the electron density map after most of the protein main chain and side chain atoms were built and refined. The ligands were refined without conformational torsion-angle restraints in order to prevent bias towards a particular ring conformation for the sugars. The final model of the complex of dCK with dC and ADP was used as starting model for the refinement of the other structures in the tetragonal space group, and to solve the structure of dCK that crystallized in the orthorhombic space group using AMoRe molecular replacement (Navaza, 1994, *Acta Cryst.* A50:157-163).

Data for the Ara-C-ADP.Mg and the gemcitabine-ADP.Mg complexes were collected to 1.6 Å and 1.9 Å resolution, respectively, on the crystals grown in PEG. Calculation of difference maps clearly showed the presence of substituents on the second position of the deoxyribose moiety of dC: an ara hydroxyl group in the case of ara-C, and two fluorine atoms in the case of gemcitabine. The ligands were modelled into the electron density maps after simulated annealing and refinement of the protein model. Water molecules were then automatically added using Arp/wARP (Perrakis et al., 1999, *Nat. Struct. Biol.* 6:458-63).

Analysis of Structural Information of Human dCK

The structural information of human dCK was useful in developing modified dCKs with enhanced activity. Human dCK (FIGS. 2A and 2B) consists of 260 amino acid residues with a calculated molecular weight of 30.5 kDa. The structure was solved using the multiwavelength anomalous diffraction (MAD) method (Hendrickson and Ogata, 1997, *Methods Enzymol.* 276:494-523) on selenomethionine-containing protein. It is a homodimeric globular protein with a fold similar to that described for the *Drosophila melanogaster* nucleoside kinase (dNK) and human dGK (Johansson et al., 2001, *Nat. Struct. Biol.* 8:616-20). Each monomer has a five-stranded parallel β-sheet core surrounded by ten α helices. Helix α4 and α7 from each monomer create a four-helix bundle dimer interface.

In humans, four spatially segregated enzymes accomplish the first step in the salvage pathway of deoxyribonucleoside triphosphate synthesis. The mitochondrial kinases dGK and thymidine kinase 2 (TK2) supply the precursors for mitochondrial DNA synthesis, and dCK and thymidine kinase 1 (TK1) do the same for nuclear DNA. Since ultimately dCK and TK1 must provide all four DNA triphosphates, it is not surprising that dCK, in addition to phosphorylating deoxycytidine (dC), also efficiently phosphorylates deoxyguanosine (dG) and deoxyadenosine (dA). In fact, apart from the thymidine-specific TK1, deoxyribonucleoside kinases are characterized by their ability to phosphorylate substrates of different base constituents. Notably, dNK, the only deoxyribonucleoside kinase in *Drosophila*, phosphorylates all four physiological deoxyribonucleosides (Knecht et al., 2002, *EMBO J.* 21:1873-1880).

Figure 2:
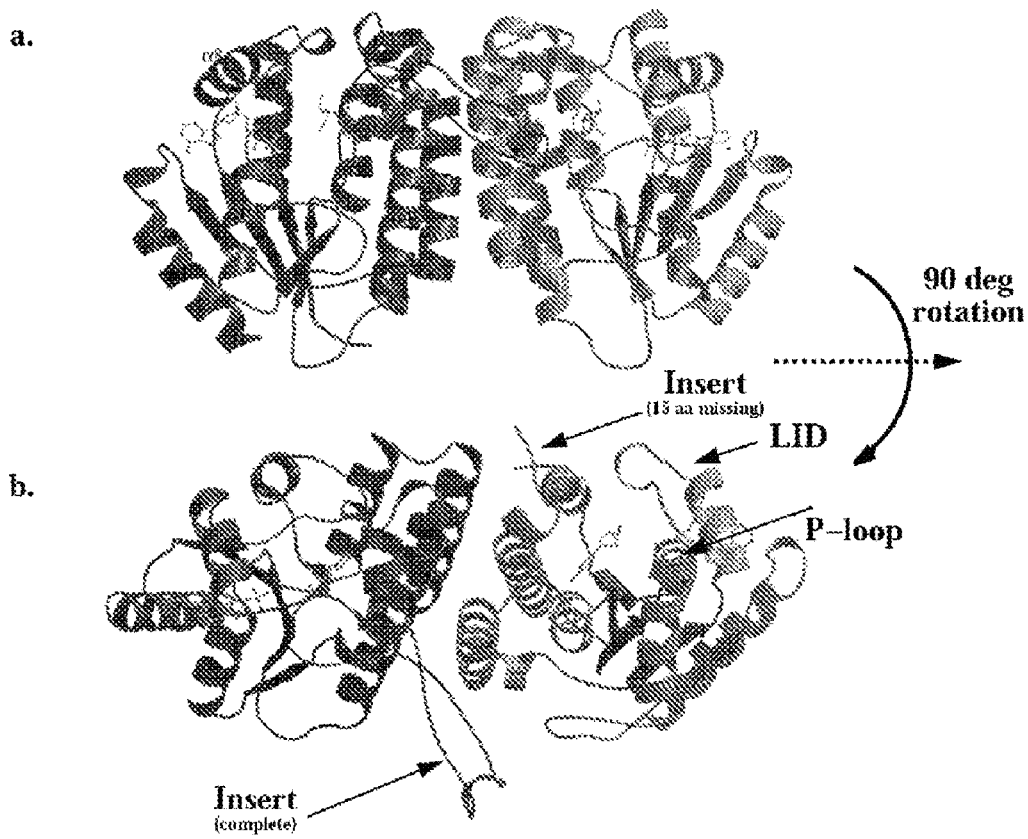
FIG. 2A is a ribbon diagram of human deoxycytidine kinase (dCK), a dimeric protein, in the presence of deoxycytidine (dC) and ADP.
FIG. 2B shows another view of the structure of human dCK in the presence of dC and ADP, rotated through 90 degrees from the view shown in FIG. 2A; the dashed arrow is the axis of rotation. The root mean square distance (r.m.s.d.) between Cα atoms of dCK and dGK or dNK is 1.17 Å, over 175 Cα atoms, and 1.20 Å over 178 atoms, respectively.
FIG. 2C shows a sequence alignment of human dCK (SEQ ID NO: 1), human dGK (SEQ ID NO: 2), Drosophila dNK (SEQ ID NO: 3) and human mitochondrial TK2 (SEQ ID NO: 4).
Figure 3:
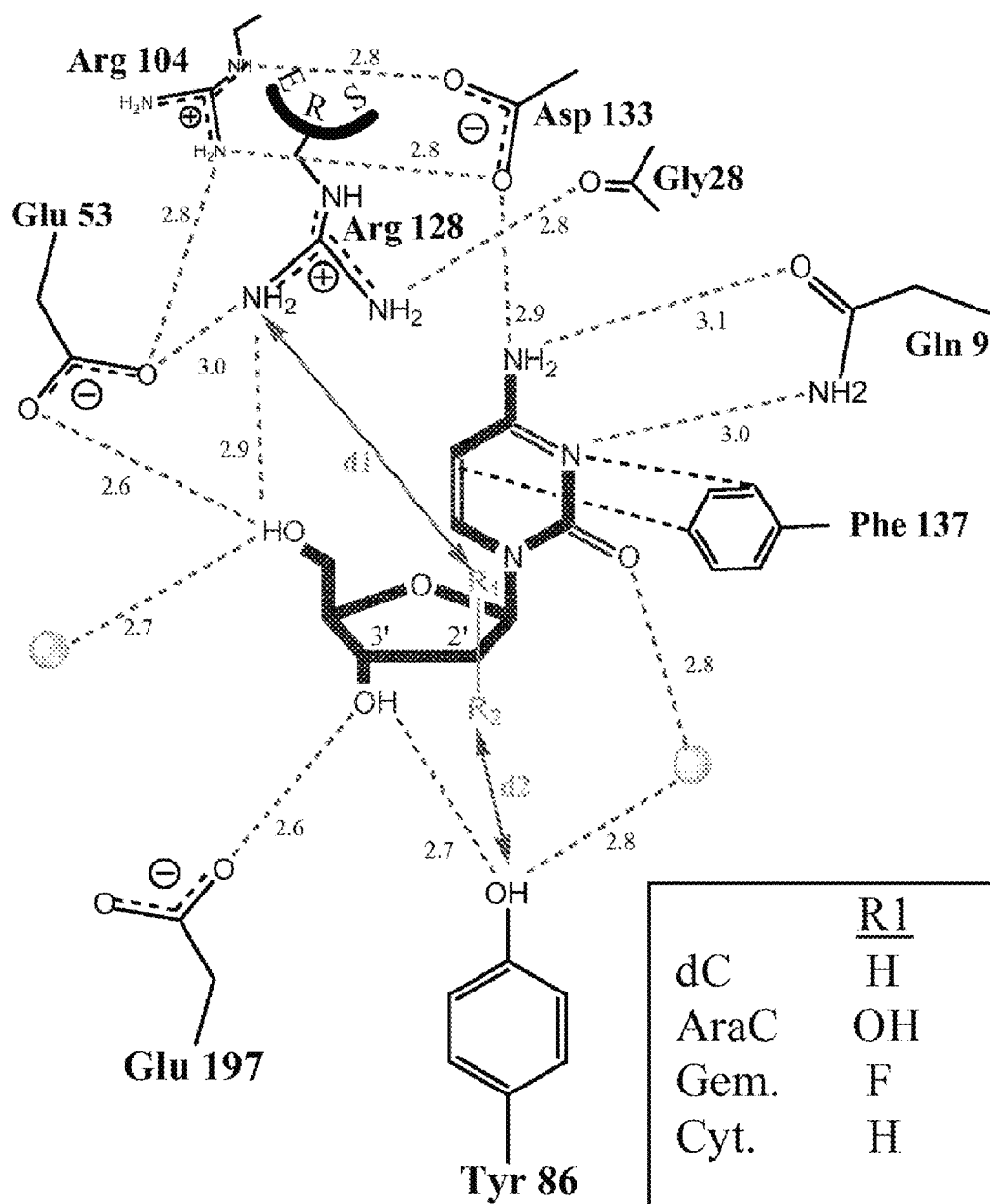
FIG. 3 is a schematic representation of the interactions made by the bound nucleoside with dCK. Arg128 of the enzyme reactive site (ERS) motif interacts with the putative base, Glu53, which is proposed to accept the proton from the substrate's 5'-hydroxyl, and with the 2'-arabinosyl ($R_1$) substituent in ara-C (a hydroxyl (OH) group) or in gemcitabine (a fluorine atom). In the case of gemcitabine, an additional interaction is possible between the 2'-ribosyl ($R_2$) fluorine atom and Tyr86. Interactions present only with the prodrugs are labeled as d1 and d2. All distances are in angstroms.

The ability of dCK to accommodate multiple substrates that are of opposite hydrogen bonding character was due to the conserved Gln97 (FIG. 2C). The hydrogen bond donating and accepting moieties of the glutamine side chain rotated and positioned themselves according to the nature of the base bound. In the structures with cytosine nucleosides, the side chain of Gln97 acted as a hydrogen bond donor, via its amide group, to the cytosine N3 atom, and as a hydrogen bond acceptor, via the carbonyl group, to the cytosine amino group (FIG. 3). This cytosine amino group also interacted with the side chain of Asp133. Discrimination by dCK against the pyrimidines thymidine and deoxyuridine was achieved because of the inability of Asp133 to perform favourable hydrogen bonding interactions in the case of a thymine or uracil base.

Adding to the discrimination against thymidine (but not deoxyuridine) is a predicted steric clash between Arg104 and the thymine methyl group. Support of this interpretation comes from mutation experiments on dNK done by Knecht et al. (2002, *EMBO J.* 21:1873-1880) and from kinetic results with a dCK triple mutant designed. In this mutant, the discriminating residues Arg104 and Asp133 were changed to a methionine and an alanine, respectively. The dCK mutant gained the ability to phosphorylate thymidine or D-type or L-type thymidine analogs. Further interactions made between the cytosine base and dCK included a hydrophobic interaction to Phe137, and a hydrogen bond to a water molecule that bridged the base and Tyr86. The interaction with Tyr86 effected deoxyribose—versus ribonucleosides discrimination.

Figure 4:
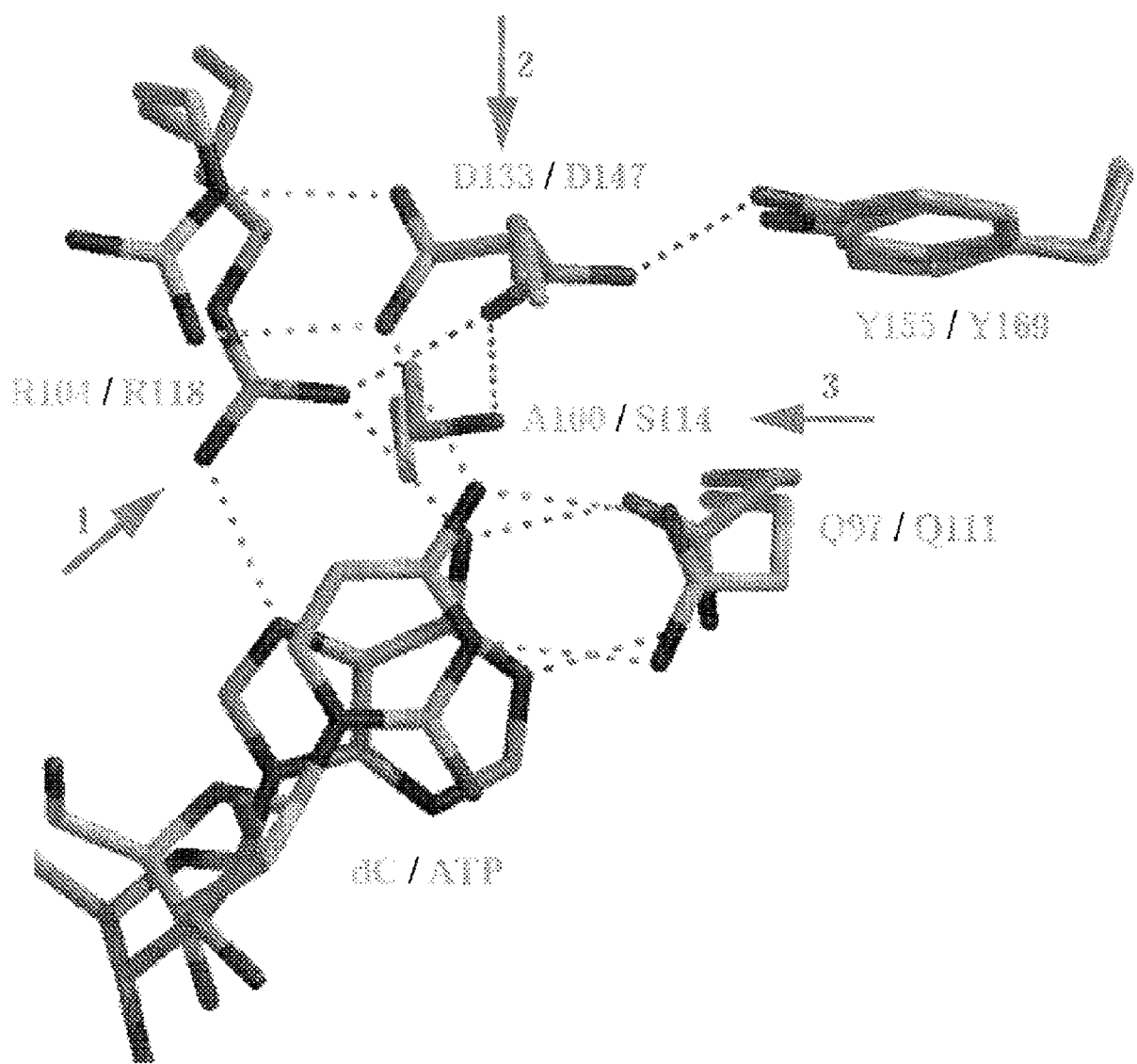
FIG. 4 shows superposition of dCK- and dGK-active site residues.

While both dCK and dGK phosphorylate dA and dG, only dCK is capable of phosphorylating dC and its analogs such as Ara-C (Herrstrom et al., 1998, *Mol. Pharmacol.* 53:270-273). The structures of dCK with dC revealed that in order to accommodate dC, Arg104 assumed a different conformation to that of Arg118 observed in the structure of dGK (FIG. 4, arrow 1). An aspartic acid residue in both the dCK and dGK structures interacted with the above-mentioned arginine (FIG. 4, arrow 2). However, only in dGK was a serine at position 114 able to participate in this network, adding to its stabilization. In contrast, in dCK at the position of the dGK-Ser114 was an alanine residue (FIG. 4, arrow 3). By having an alanine instead of a serine, the hydrogen-bonding network holding rigid the aspartic acid and arginine residues was weaker, allowing for a less extended conformation of Arg104 with a concomitant change in conformation for Asp133 upon dC binding. At the same time, upon purine binding to dCK, a change in the Arg104 to an extended conformation as observed in the dGK structure was still possible. The conserved tyrosine in position 155 supplied an important hydrogen bond to Asp133 in the conformation compatible with purine binding.

A common feature among the nucleoside kinases is the stabilization of the sugar 3'-hydroxyl group by a conserved Tyr-Glu pair (dCK-$Y_{86}E_{197}$; dGK-$Y_{100}E_{211}$; dNK-$Y_{70}E_{172}$) (Johansson et al., 2001, *Nat. Struct. Biol.* 8:616-20). Due to proximity of the tyrosine hydroxyl group to the 2'-sugar position, this residue functions to favor deoxyribonucleosides over ribonucleosides. The isosteric substitutions of protons by fluorines at the 2'-position in gemcitabine put one of these fluorines at an interacting distance to the tyrosine hydroxyl group. Even a slightly larger substituent at this position resulted in some steric repulsion, as evidenced by the high $K_M$ of cytidine in comparison to that of deoxycytidine (Table 2).

Figure 5:
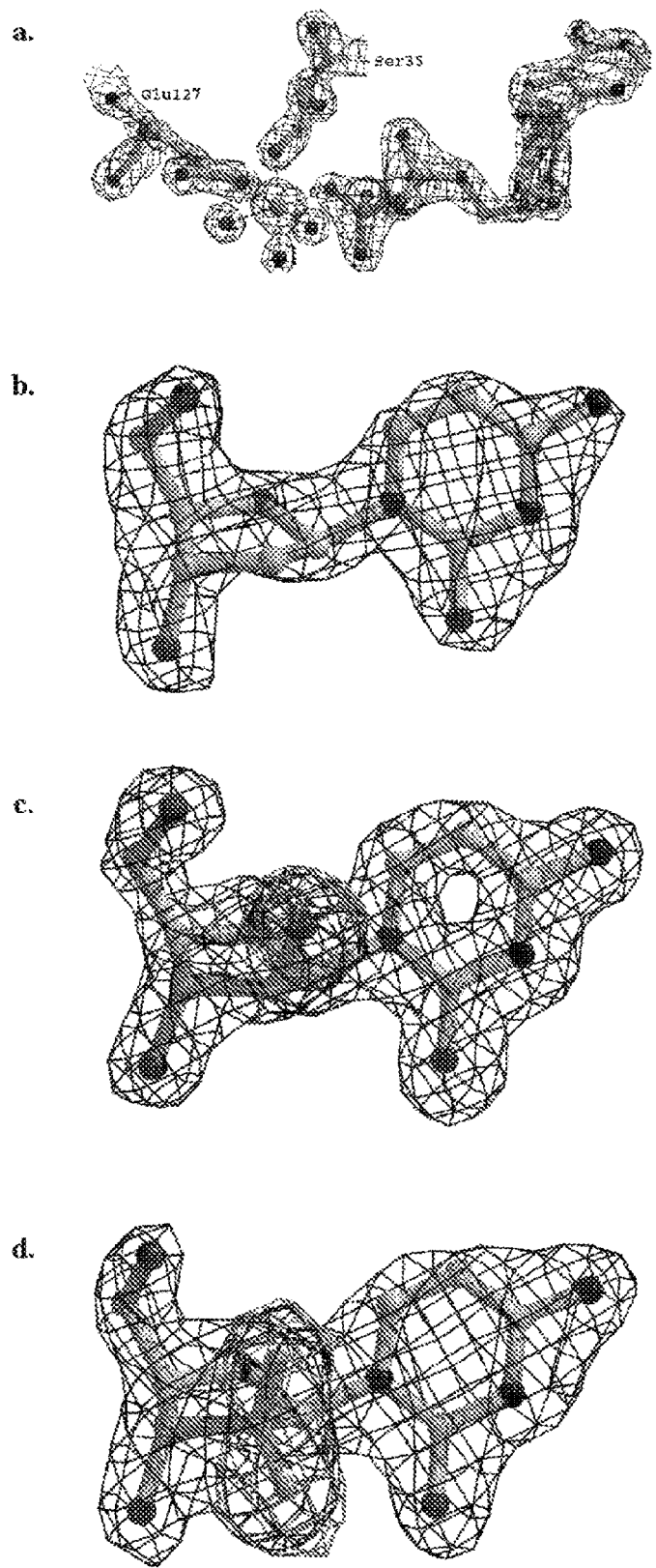
FIG. 5A shows an electron density map of dCK bound to an ADP molecule with an octahedral coordinated magnesium atom.
FIG. 5B shows an electron density map of dCK bound to deoxycytidine.
FIG. 5C shows an electron density map of dCK bound to AraC.
FIG. 5D shows an electron density map of dCK bound to gemcitabine.

The structures of dCK with Ara-C-ADP.Mg and the one with gemcitabine-ADP.Mg (FIG. 5) were both similar to the dC-ADP complex, with a root mean square deviation of 0.66 Å and 0.63 Å, respectively. Compared to the structure with dC bound in the active site, the hydroxyl group in the 2'-position of the arabinofuranosyl sugar in Ara-C provided an additional 3.0 Å (d1, FIG. 3) hydrogen bond to the conserved Arg128 of the ERS motif (FIG. 2C). A similar interaction (2.9 Å) with Arg128 was formed by the fluorine atom ($R_1$) of gemcitabine, while the other fluorine ($R_2$) made a 2.7 Å hydrogen bond with Tyr86 (d2, FIG. 3).

The proton from the sugar 5'-hydroxyl could be accepted by a nearby base (either prior to the O5' nucleophilic attack on the ATP γ-phosphate, or after the formation of the O—P bond). The conserved Glu53 at hydrogen bonding distance to the sugar 5'-hydroxyl group (2.6 Å via OE2) and to NH1 of Arg128 (3.0 Å via OE1) (FIG. 3) was a very likely candidate for the fulfilment of this role as base. In the three complexes, the atomic positions of Glu53, Arg128 and the nucleosides or prodrugs were identical within experimental error, suggesting that the origin of the increased dCK activity towards the two cytosine analogs resulted from the interactions of Arg128 to R1 and of Tyr86 to R2.

Both Ara-C and gemcitabine possess the Arg128 to R1 interaction and the increase in enzymatic efficiency for the two prodrugs was similar demonstrating that this interaction plays a predominant role. Assuming that the observed steady-state kinetic rate reflected the phosphoryl transfer step, then the increased rate for Ara-C/gemcitabine could be explained as follows: in the presence of dC, the interaction between Glu53 and Arg128 was not weakened by the substrate. However, a hydrogen-bond acceptor at the 2'-arabinosyl position, as present in Ara-C and gemcitabine, competed with Glu53 for the Arg128 interaction. A weaker Glu53-Arg128 interaction would potentiate the proton accepting ability of the carboxylic acid group from the O5'-hydroxyl. As a result, the nucleoside 5'-hydroxyl group would become more nucleophilic and hence the $k_{cat}$ for Ara-C and gemcitabine phosphorylation was increased.

The positive influence of hydrogen-bonding acceptor substituents at the 2'-arabinosyl position on dCK activity was also supported by the recent discovery that the purine drug 2-chloro-2'-arabino-fluoro-2'-deoxyadenosine, clofarabine, a new derivative of cladribine that is currently undergoing phase II clinical trial for pediatric leukemia, is ~3-fold more efficient substrate for dCK than cladribine (Lotfi et al., 1999, *Clin. Cancer Res.* 5:2438-44; Mansson et al., 2003, *Biochem. Pharmacol.* 65:237-247). On the basis of the structures presented here, this improvement was likely caused by the interaction of the 2'-arabino-fluorine atom of clofarabine with Arg128, thus improving the ability of Glu53 to function as a base.

Another important interaction involved in the stabilization and positioning of the nucleoside sugar was made by the 3'-hydroxyl group. The complexes with Ara-C and gemcitabine were crystallized under the same conditions as that of dC. However, with the antiviral drug 2',3'-dideoxy-cytidine (ddC) no crystals were obtained. This may suggest that weak ddC binding ($K_M$ of 407 µM versus 6.2 µM for dC, Table 2) did not induce the same enzyme conformation necessary to promote crystal growth. A likely explanation for such behavior could be found in the lack of the 3'-hydroxyl group in ddC. Indeed, in all the dC, ara-C and gemcitabine structures, the 3'-hydroxyl group was held in place by Glu197 and Tyr86 (FIG. 3), which are strictly conserved residues within the deoxyribonucleoside kinases dCK, dGK, TK2 and dNK (FIG. 2C).

Thus, modified prodrug molecules that include a hydrogen bond acceptor(s) at the 2'-position (e.g. hydroxyl group or fluorine in the 2'-arabinosyl position, or fluorines in both 2'-positions) would counter the low phosphorylation efficiency of ddC, and hence increase its antiviral effect.

Improving dCK Catalytic Efficiency dCK is an inefficient enzyme as a result of a very slow $k_{cat}$ (0.03 sec$^{-1}$; Table 3). In contrast, dNK exhibits a 2,500-fold higher efficiency for dC phosphorylation resulting mainly from its faster $k_{cat}$ (16.5 sec$^{-1}$) (Knecht et al., 2002, *EMBO J.* 21:1873-1880). With the goal of making dCK more active key active site residues in dCK were mutated to those found in dNK. First, the structures of human dCK and the *drosophila* dNK were overlaid. This permitted residues likely to be important for catalysis to be identified. It was expected that residues present in dNK but absent in dCK and identified in this manner would also identify residues involved in or responsible for dNK's higher enzymatic rate. Since Arg104 plays a role in the already mentioned active site hydrogen-bonding network, its mutation to the uncharged methionine was combined with the compensatory change of Asp133 to an alanine The amino acid sequence of the resulting mutant dCK with Arg104Met and Asp133Ala substitutions (dCK-R104M/D133A) is shown in SEQ ID NO:6. In alternative embodiments, Ala100 was changed to a valine as is found in dNK. The amino acid sequence of the resulting mutant dCK with Ala100Val, Arg104Met and Asp133Ala substitutions (dCK-A/100V/R104M/D133A) is shown in SEQ ID NO:5.

Steady-state kinetic assays were performed by determining deoxycytidine kinase activity using a colorimetric assay (Agarwal et al., 1978, *Methods Enzymol.* 51:483-490) in 50 mM Tris/HCl, pH 7.5, 100 mM KCl, 5 mM MgCl$_2$, at 37° C. The concentration of dCK was 0.4 µM, ATP.Mg 1 mM, while for the nucleosides and the nucleoside analogs a range of concentrations between 10 µM and 1 mM were used unless indicated otherwise. All experiments were performed in duplicates.

The steady-state kinetic experiments using Ara-C, gemcitabine and dC as substrates showed that there was a 10-fold increase in the $k_{cat}$ but only a slight increase in $K_M$ for the two prodrugs compared to dC (Table 3). Overall there was a ~4-fold higher enzymatic efficiency for dCK with Ara-C and gemcitabine.

Table 3 demonstrates that the A100V/R104M/D133A human dCK mutant was more active than wild-type enzyme: efficiency towards dC increased by 50-fold, towards gemcitabine by 4-fold, with no significant change for Ara-C (Table 3).

TABLE 3

Steady State Kinetic Data

| Nucleoside | $K_M$ (µM) | $k_{cat}$ (sec$^{-1}$) | $k_{cat}/K_M$ (M$^{-1}$ sec$^{-1}$) |
|---|---|---|---|
| Wild Type dCK | | | |
| dC | 6.2 | 0.03 | 4.8 × 10$^{-3}$ |
| ddC | 406.8 | 0.18 | 0.4 × 10$^{-3}$ |
| cytidine | 382.7 | 0.74 | 1.9 × 10$^{-3}$ |
| Ara-C | 15.5 | 0.26 | 16.8 × 10$^{-3}$ |
| gemcitabine | 22.0 | 0.37 | 16.8 × 10$^{-3}$ |
| A100V/R104M/D133A-dCK | | | |
| dC | 4 | 0.93 | 232.5 × 10$^{-3}$ |
| Ara-C | 102 | 1.73 | 17.0 × 10$^{-3}$ |
| gemcitabine | 50 | 3.52 | 70.4 × 10$^{-3}$ |

It was discovered that dCK with the R104M and D133A substitutions, with or without the A100V substitution (as will be shown below), exhibited improved activity in phosphorylating cytidine or cytidine analogs.

Not only did the above mentioned mutation improve the activity of modified dCK in phosphorylating cytidine or cytidine analog, both dCK R104M/D133A and dCK A100V/R104M/D133A acquire additional activity in phosphorylating thymidine and thymidine analogs. Thymidine analogs useful in the current invention include without limitation, 2'-3'-didehydro-2'-3'-dideoxythymidine (Stavudine), Azidothymidine (AZT), Bromodeoxyuridine (BrdU), and (E)-5-(2-bromovinyl)-2'-deoxyuridine (BVdU). As shown in the examples below, dCK mutants with the R104M and D133A mutations, are able to phosphorylate thymidine and thymidine analogs, such as BVdU, whereas wild type dCK cannot.

In conclusion, the high-resolution structures of dCK in complex with dC and two clinically used prodrugs revealed determinants of substrate specificity. Moreover, the structures are useful as starting point for the design of modified dCK that has enhanced enzymatic activity and/or extended substrate specificity for additional nucleoside analogs.

Example 2

Conjugation of HuM195 to dCK

In-vitro purified dCK was chemically conjugated to HuM195 (Protein Design Laboratories, Fremont, Calif.). A purification protocol was used to obtain only the conjugate, which was performed as follows. A Sepharose S-200 column (Amersham Biosciences), a column that separate macromolecules according to size was used, wherein the first peak to elute for the column was the HuM195-dCK conjugate. Only this peak was collected, and concentrated to ~3 mg/ml. The activity of the conjugate was verified using a colorimetric spectrophotometric assay. As a proof of concept, a standard protein conjugation technique was used for the conjugation of wild type dCK with HuM195. Conjugation of enzymes to antibodies involves formation of a stable covalent linkage between an enzyme and an antigen specific monoclonal or polyclonal antibody in which neither the antigen-combining site of the antibody nor the active site of the enzyme is functionally altered. Briefly, the enzyme dCK was dialyzed against 2 liters of 0.1 M phosphate buffer overnight at 4° C. while stirring gently. Afterward, the phosphate buffer was replaced and dialysis was continued for 2 hours. Then M-maleimido benzoyl-N-hydroxysuccinimide ester in dimethyl formamide (MBS/DMF) solution was added to the monoclonal antibody HuM195 (MBS/antibody ratio 120:1) and the mixture was stirred gently at room temperature for 30 minutes. The solution was then filtered and loaded on the Hi Prep 26/10 desalting column, which was pre-equilibrated with 100 ml phosphate buffer. The first peak was collected and concentrated into 1.5 ml; the second peak contained free MBS. The concentrated first peak was pooled with dialyzed enzyme (enzyme antibody weight ratio was 4:1) and stirred for 2 hours at room temperature. After 2 hours, the solution was filtered and injected into Superdex 200 gel filtration column. The first peak, which was the HuM195 TMPK conjugation product, was eluted and concentrated. A gel electrophoresis was then run and the conjugation product is confirmed. The same method can be used to generate antibody-conjugates of other in vitro purified dCK mutants or other antibodies described herein.

HuM195-dCK activity was determined using a colorimetric assay in 50 mM Tris/HCl, pH7.5, 100 mM KCl, 5mM $MgCl_2$, at 37° C. The concentrations used were: HuM195-dCK 0.4 μM, ATP Mg 1 mM, and the nucleosides and nucleoside analogs in a range of concentrations between 10 μM and 1 mM. All experiments were performed in duplicate. Kinetic data were evaluated using the program Sigma Plot 2000 and were best described by the Michaelis—Menten equation $v=V_{max} \times [S]/(K_m+[S])$. Modified dCK of the current invention can be conjugated to an antibody following the same procedure.

Example 3

Testing the HuM195-dCK Conjugate in CD33 Positive Cell Lines

Figure 6:
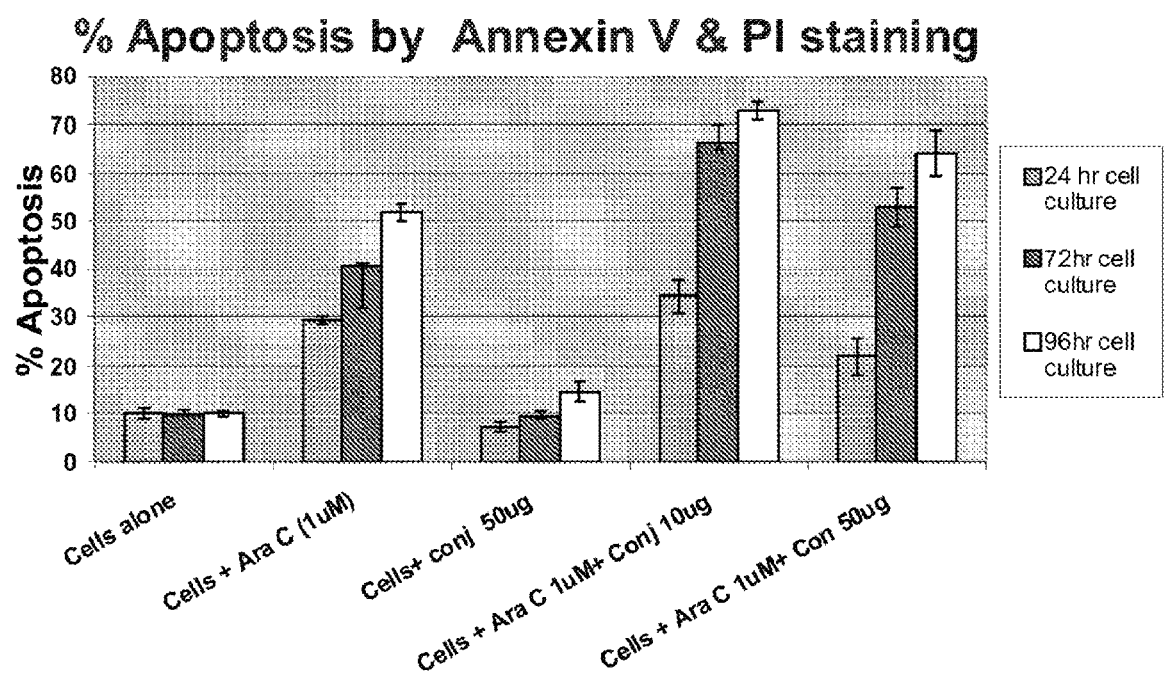
FIG. 6 depicts a graph demonstrating an increased percentage of apoptotic HL60 cells treated with AraC alone, the dCK-antibody conjugate alone, or in combination.

The HuM195 antibody will only bind and internalize to cells expressing CD33. Thus, the HL60 cell line (derived from AML cells) and the NB4 cell line, which are CD33 positive, were used to test the activity of the HuM195-dCK system in live cells. The cells were treated with AraC, the HuM195-dCK conjugate, or the combination of HuM195-dCK and the AraC. Annexin V and propidium iodide (PI) staining was used to identify apoptotic cells. As shown in FIG. 6, cells alone as a control had about 10% cell death, AraC at 1 μM increased cell death as a function of time, with ~50% cell death after 96 hours, the conjugate by itself was not toxic, and the conjugate in combination of AraC results in the most efficient cell death (~70% killing after 96 hours). The combination of AraC with the conjugate results in 20% more killing than AraC alone.

Figure 7:
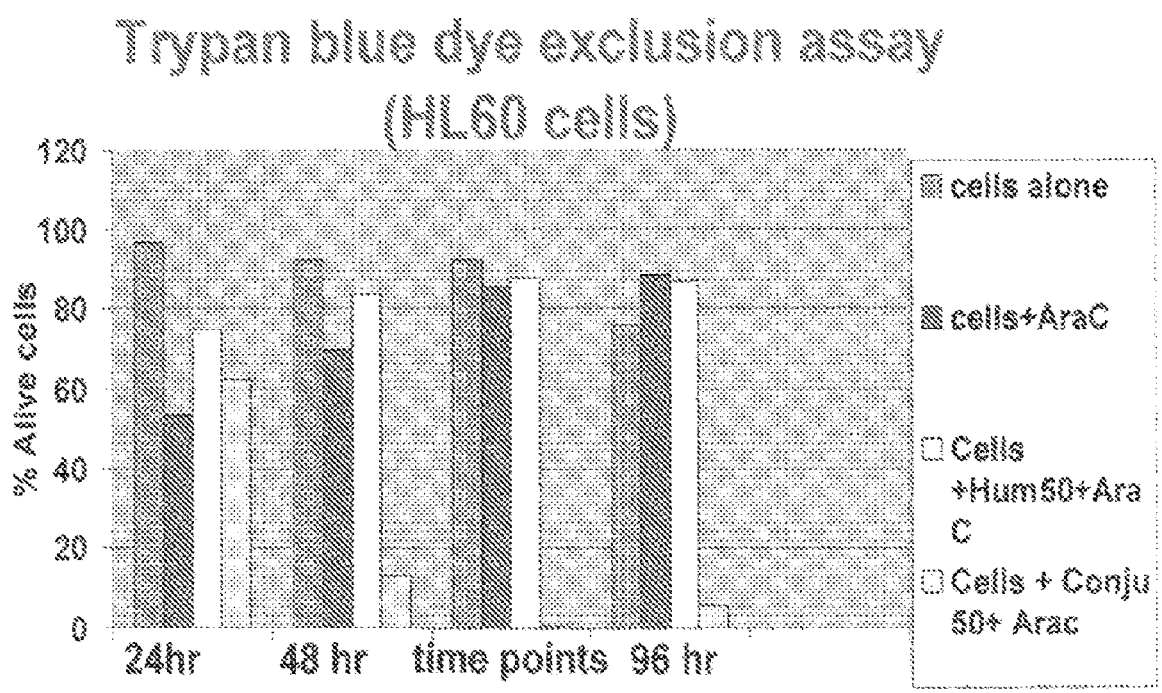
FIG. 7 depicts a graph demonstrating HL60 cell death assayed by trypan blue staining after treatment with AraC or dCK-antibody conjugate, alone or in combination.

In addition, a trypan blue exclusion assay was performed on cells treated with AraC, the HuM195-dCK conjugate, or the combination of HuM195-dCK and the AraC (FIG. 7). In the trypan blue assay, a large number of positively stained cells correspond to a large number of dead cells. As expected, the cells treated with a combination of the conjugate and AraC showed the most effective cell killing.

Figure 8:
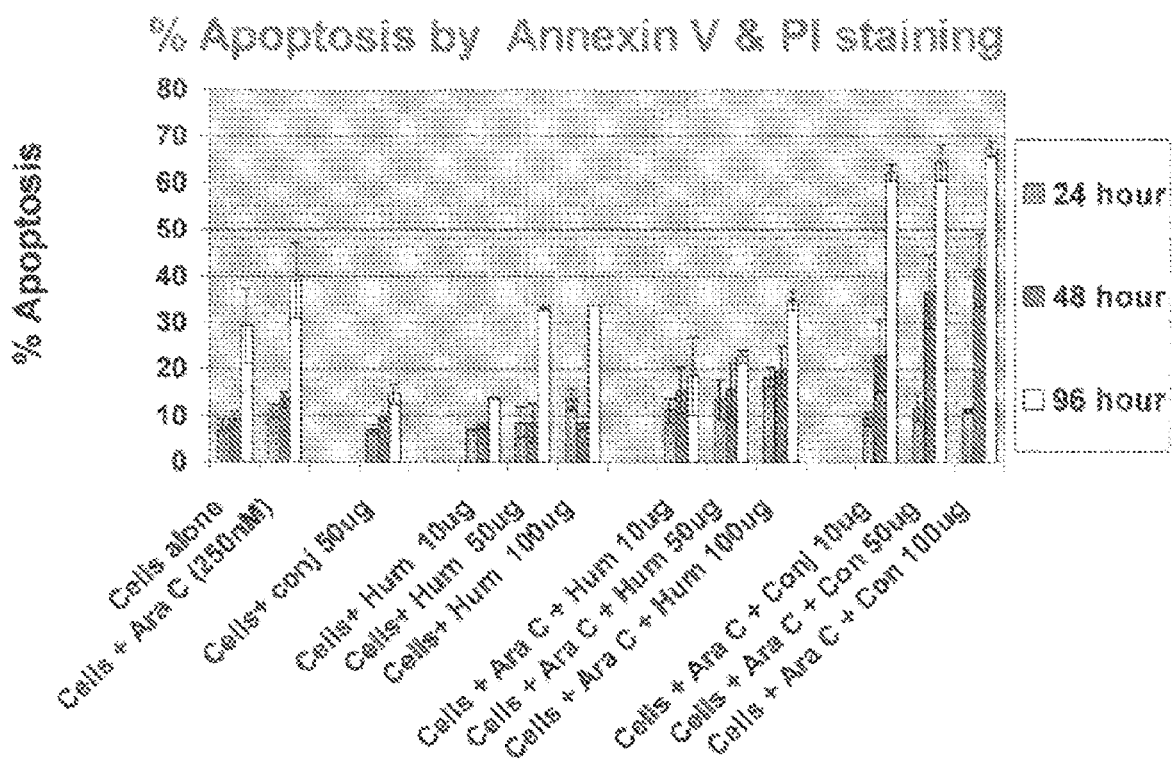
FIG. 8 depicts a graph demonstrating an increased percentage of apoptotic NB4 cells treated with AraC or the dCK-antibody conjugate, alone or in combination.

The NB4 cells were also treated with AraC, the HuM195-dCK conjugate, or the combination of HuM195-dCK and the AraC, and an apoptosis assay was performed as above. The AraC dose used, however, was decreased from 1000 nM to 250 nM. The results were similar to those observed in the HL60 cells (FIG. 8). The conjugate with AraC (right bars) achieve ~65% cell killing after 96 hours, whereas AraC alone was below 40%.

Example 4

Verifying CD33-Positive Cell Specificity of HuM195-dCK

Figure 9A:
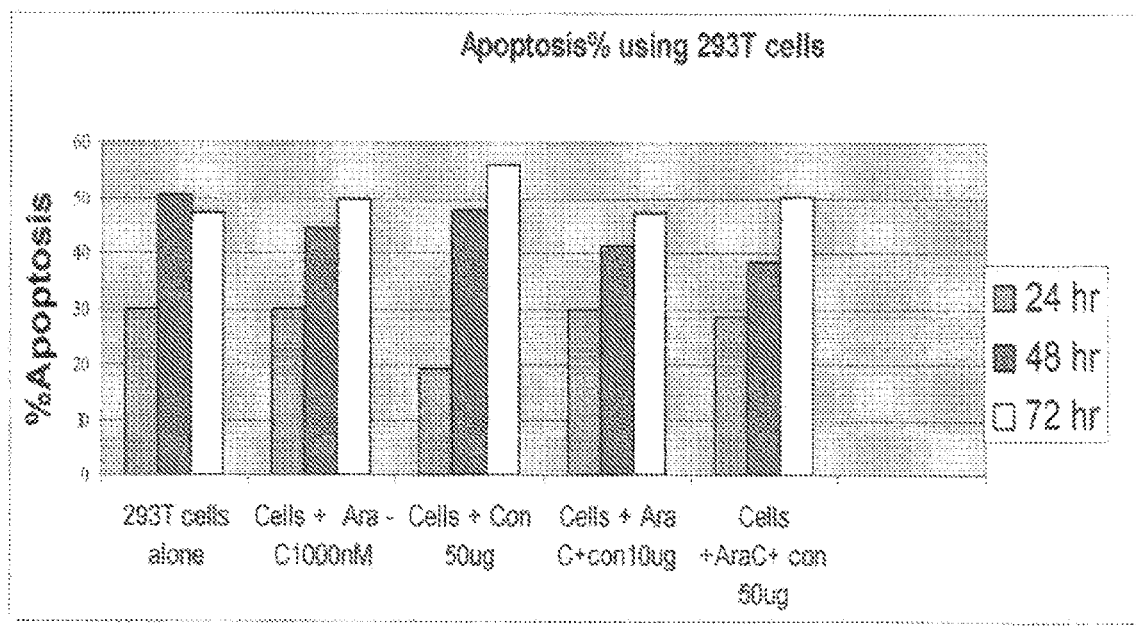
FIG. 9A depicts a graph demonstrating the percentage of apoptotic 293T cells treated with AraC or the dCK-antibody conjugate, alone or in combination.
Figure 9B:
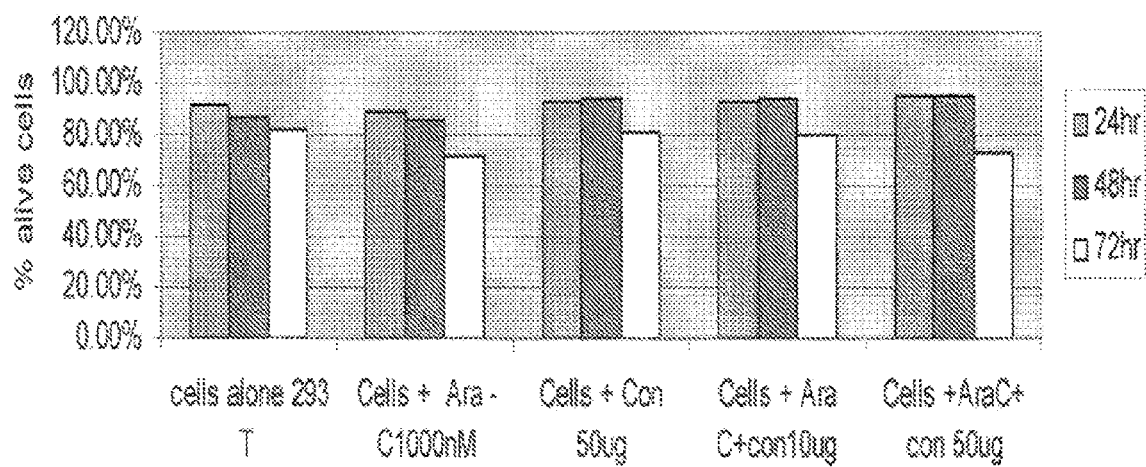
FIG. 9B depicts a graph demonstrating 293T cell death after treatment with AraC or the dCK-antibody conjugate, alone or in combination.

To verify that the HuM195-dCK conjugate was only delivered to CD33 positive cells, experiments were repeated with CD33 negative cells (293T cells). Flow cytometry (FIG. 9A) and a trypan blue exclusion assay (FIG. 9B) were used to determine AraC-mediated cell killing. In both assays, similar killing efficiency for AraC and for the combination of AraC and the conjugate was observed. Thus, the conjugate did not enter the 293T cells as expected.

Example 5

Verifying HuM195-dCK Activity in Mouse Models of Leukemia

To verify the activity of the HuM195-dCK conjugate in mammals, C.B-17-SCID/SCID mice are used. The mice are irradiated with 300 cGY total body irradiation and after 2-4 hours of observation are injected intravenously via tail vein with $1 \times 10^7$ HL60 cells diluted in 0.1 ml of HBSS. A total of 20 control mice are used and the treated mice are injected intraperitoneally as follows: Group A: No treatment; Group B: Ara-C 1.0 μg/day (n=10); Group C: Ara-C 1.0 μg/day as well as the conjugate at varying doses of 10 and 50 μg/day (n=10 each); and Group D: conjugate alone 10 and 50 μg/day (n=10 each).

Group A is the control animals without any treatment. Group B reveals the therapeutic effect of Ara-C alone. Group D tests for the effect of the conjugate. Group C shows the synergistic effect of adding the conjugate to the Ara-C.

The mice are examined daily for overall activity and for presence of masses. Moribund mice are sacrificed. Samples from various mouse organs are removed and the tissues are fixed in formaldehyde embedded in paraffin and are examined under microscope. The median survival of the control mice is compared with the mice treated with Ara-C alone, Ara-C and conjugate and conjugate alone. Mice living more than 150 days are sacrificed and examined at autopsy for evidence of any HL60 related tumors in various organs including their bone marrow.

Example 6

Assays for Enzymatic Activities of Modified dCK with Substitutions at Amino Acid Position 104

A series of dCK mutants were generated with amino acid substitutions at positions 104 and 133. Hydrophobic amino acid substitutions other than methionine at position 104 were tested in the backbone of D133A substitution. Amino acids with small side chain were not considered because replacing an arginine residue with a small amino acid would likely result in destabilization of the structure of the protein. Instead, phenylalanine, leucine, isoleucine, and valine were considered. Additionally, glutamine substitution at position 104 was tested, as it is uncharged and large enough to substitute the arginine, but small enough to make space for the thymine base. Lastly, replacement of arginine by the more flexible lysine was also tested. Mutants were generated and purified in a single step by metal-affinity chromatography, yielding preparations of >95% purity. The N-terminal His-tag was not cleaved since previous experiments have shown that the tag does not influence the kinetic behavior of the protein (data not shown). In the following experiments, saturating concentration of ATP (1 mM) and a low nucleoside concentration of 200 μM were used for the purpose of screening for mutants that have relatively low nucleoside $K_m$ values.

a. Activity of Mutants Toward the Physiological Substrates of dCK: dC, dA and dG In contrast to dCK, the enzyme dNK is able to phosphorylate all four bases with $k_{cat}$ values varying from 14 to 20 sec$^{-1}$. dNK is a more efficient enzyme as compared to dCK: for dCK, the $k_{cat}$ is 0.04 sec$^{-1}$ for pyrimidine dC, and ~2.5 sec$^{-1}$ for purines substrates dA and dG (see below). Table 4 shows unexpectedly that not all hydrophobic amino acid substitutions at position 104 produced the same result: among all the mutants tested that had a alaine at position 133 and a hydrophobic amino acid substitution at

TABLE 4

Kinetic characterization of dCK variants with mutations at positions 104 and 133 with respect to the physiological nucleoside substrates

| Mutant | $^a k_{obs}$ D-dC | Rel $k_{obs}$ | $k_{obs}$ D-dG | Rel $k_{obs}$ | $k_{obs}$ D-dA | Rel $k_{obs}$ |
|---|---|---|---|---|---|---|
| WT | 0.03 ± 0.01$^b$ | 1 | 0.94 ± 0.18 | 1 | 1.19 ± 0.01 | 1 |
| R104M/D133A | 1.84 ± 0.04 | 61 | 0.18 ± 0.01 | 0.19 | 0.37 ± 0.01 | 0.31 |
| R104L/D133A | 0.27 ± 0.09 | 9 | 0.30 ± 0.01 | 0.32 | 3.45 ± 0.16 | 2.9 |
| R104I/D133A | 0.06 ± 0.01 | 2 | 0.08 ± 0.01 | 0.08 | 0.21 ± 0.01 | 0.18 |
| R104Q/D133A | 0.08 ± 0.01 | 2.7 | 0.06 ± 0.01 | 0.06 | 0.18 ± 0.04 | 0.15 |
| R104V/D133A | <0.005 | | <0.005 | | <0.005 | |
| R104F/D133A | <0.005 | | <0.005 | | <0.005 | |
| R104K/D133A | <0.005 | | <0.005 | | <0.005 | |

$^a k_{obs}$ are in sec$^{-1}$ determined for a nucleoside concentration of 200 μM
$^b$Standard deviation position 104, dCK R104M/D133A and dCK R104L/D133A were the most active when a physiological substrate was used. At the sensitivity threshold of the assay, the mutant dCK R104F/D133A showed no activity, presumably due to the bulkiness of the phenyl group that was unable to fit in the space previously occupied by the more linear arginine. Mutants with other beta-branched side chains also showed little or no activity—the isoleucine variant being significantly lower than the leucine counterpart, though still more active than wild-type dCK with D-dC as the substrate, and the valine variant below the activity cut-off.

While the $k_{cat}$ of dNK is relatively similar between different nucleosides (14 to 20 sec$^{-1}$), the R104M/D133A and R104L/D133A mutants showed selective rate enhancement for specific nucleosides as compared to wild type dCK. The dCK R104M/D133A variant is >60-fold faster ($k_{obs}$:$k_{cat}$ determined at 200 μM nucleoside) with the pyrimidine dC in comparison to wild-type dCK. In contrast, $k_{obs}$ with the purines dA and dG were lower in the mutant than the wild-type. It is thus suggested that dCK R104M/D133A prefers pyrimidine substrates over purines. In contrast, the dCK R104L/D133A variant preferred dA, while exhibited a ~10-fold lower $k_{obs}$ values for dC and dG (though it is still more active than wild type dCK for dC). These results suggested that the residue at position 104 can affect the rate as well as substrate preference of the enzyme.

b. Activity of Mutants Toward the dC Analogs AraC and Gemcitabine

Nucleoside analogs, such as AraC and gemcitabine, have been used for the treatment of hematological malignancies and some types of solid tumors. Wild-type dCK phosphorylates both of these dC analogs at similar rate, with a 10-13 fold higher $k_{obs}$ as compared to dC as substrate (compare Table 4 with Table 5). Similar to the results shown in Table 4, dCK R104M/D133A and R104L/D133A were more active than wild-type when a non-physiological dC analog was used (Table 5).

TABLE 5

Kinetic characterization of dCK variants with mutations at positions 104 and 133 with respect to the non-physiological substrates AraC and Gemcitabine

| Mutant | $^a k_{obs}$ AraC | Rel $k_{obs}$ | $k_{obs}$ Gem | Rel $k_{obs}$ |
|---|---|---|---|---|
| WT | 0.30 ± 0.04$^b$ | 1.00 | 0.39 ± 0.01 | 1.00 |
| R104M/D133A | 0.84 ± 0.02 | 1.70 | 2.39 ± 0.07 | 5.80 |
| R104L/D133A | 0.64 ± 0.06 | 0.35 | 2.04 ± 0.03 | 5.20 |
| R104I/D133A | 0.07 ± 0.01 | 0.25 | 0.21 ± 0.08 | 0.53 |
| R104Q/D133A | 0.18 ± 0.01 | 0.60 | 0.17 ± 0.04 | 0.43 |

TABLE 5-continued

Kinetic characterization of dCK variants with mutations at positions 104 and 133 with respect to the non-physiological substrates AraC and Gemcitabine

| Mutant | $^a k_{obs}$ AraC | Rel $k_{obs}$ | $k_{obs}$ Gem | Rel $k_{obs}$ |
|---|---|---|---|---|
| R104V/D133A | <0.005 | | <0.005 | |
| R104F/D133A | <0.005 | | <0.005 | |
| R104K/D133A | <0.005 | | <0.005 | |

$^a k_{obs}$ are in sec$^{-1}$ determined for a nucleoside concentration of 200 μM
$^b$Standard deviation Different from the wild-type enzyme, which showed no preference between AraC and gemcitabine, the R104M/D133A and R104L/D133A variants showed preference between AraC and gemcitabine: gemcitabine was phosphorylated noticeably faster (5- to 6-fold), but AraC was only slightly better, by the mutants than by the wild-type. Thus, these dCK variants have gained a preference for gemcitabine, despite the fact that the structural elements that differentiate AraC from gemcitabine are confined to the sugar moiety, and the site of the mutation at position 104 is not in close proximity to the sugar moiety in the substrate binding site. Under the same experimental conditions, the mutants that exhibited undetectable activity with the physiological substrates also showed no activity with the nucleoside analogs.

Example 7

Enzymatic Activity of dCK R104M/D133A in Phosphorylating Thymidine Analogs

Several dCK mutants disclosed herein showed unique kinetic properties with respect to clinically-important nucleoside analogs. In addition to enhanced kinetic rate with conventional substrate compounds such as gemcitabine and AraC, the dCK mutants A100V/R104M/D133A and R104M/D133A have acquired the ability to phosphorylate thymine-based nucleoside analogs. Wild-type dCK does not phosphorylate thymine or thymine-related nucleosides.

(E)-5-(2-bromovinyl)-2'-deoxyuridine (BVdU) is a thymidine analog used for the treatment of oral herpes infections. To attain pharmacological activity, this compound must be phosphorylated. Human enzymes are very poor at phosphorylating this nucleoside analog, whereas the herpes thymidine kinase does so efficiently. This is the basis for the selectivity of this compound against herpes infections.

To assess the feasibility of using BVdU as a target therapy for cancer treatment, the in vitro kinetics of BVdU phosphorylation by dCK R104M/D133A was measured. BVdU at a concentration of 200 μM was incubated with 350 nM dCK R104M/D133A at 37° C. in the presence of 1 mM ATP. An enzyme-coupled colorimetric assay was used to determine the rate of phosphoryl transfer by modified dCK (see FIG. 10). The principle of the assay is described below using dC as an exemplary substrate.

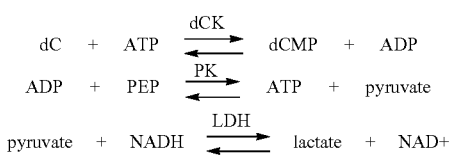

Figure 10:
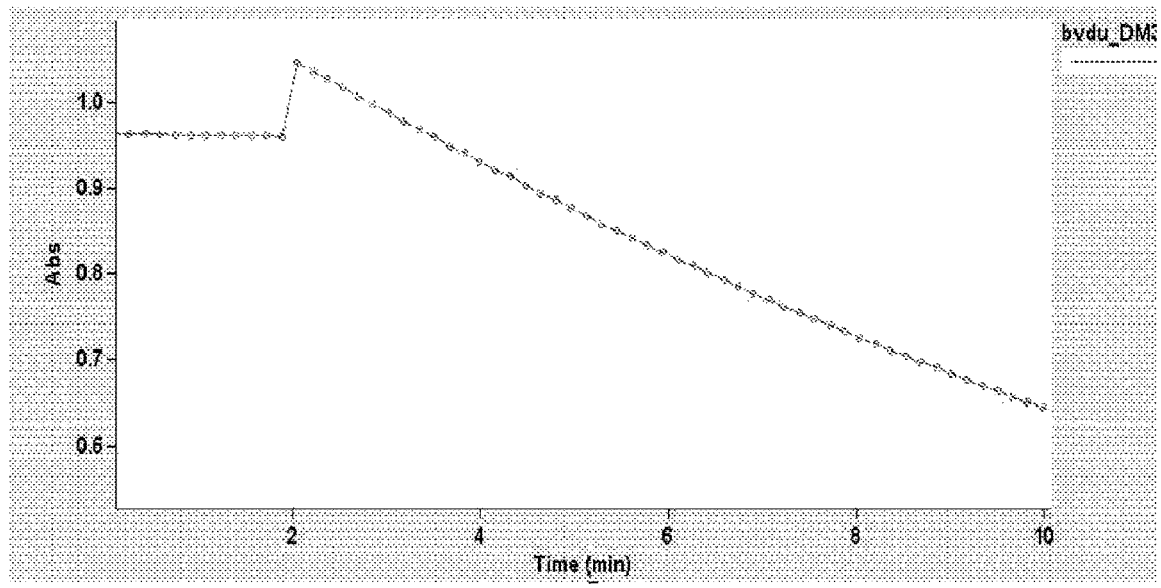
FIG. 10 depicts a graph showing the kinetics of phosphorylation of (E)-5-(2-bromovinyl)-2'-deoxyuridine (BVdU) by dCK R104M/D133A mutant.

The kinetic assay mixture contains, in addition to modified dCK and ATP, a nucleoside or nucleoside analog (e.g., dC or BVdU), pyruvate kinase (PK), lactate dehydrogenase (LDH), and small molecules phosphoenolpyruvate (PEP) and NADH. Modified dCK phosphorylates nucleoside dC or a nucleoside analog such as BVdU, and converts ATP to ADP. The enzyme PK converts ADP and PEP to ATP and pyruvate, respectively. Pyruvate thus produced becomes a substrate for LDH, which converts pyruvate to lactate and concomitantly NADH to NAD+. NADH absorbs at wavelength 340 nm, while NAD+ does not. Therefore, as the reaction proceeds, the concentration of NADH is reduced, and the absorbance at 340 nm is decreased. The reduction in absorbance indicates production of $NAD^+$, as a result of production of ADP, which is a marker for phosphoryl transfer catalyzed by dCK. The graph in FIG. 10 shows absorbance at 340 nm as a function of time, from which the kinetics of the phosphorylation reaction can be calculated. Based on these results, a turnover number ($k_{cat}$) of 0.43 $sec^{-1}$ can be calculated for the phosphorylation of BVdU by dCK R104M/D133A.

Example 8

Capacity of Antibody-Conjugated dCK R104M/D133A to Convert BVdU into a Toxic Metabolite in a Cell An in vitro $k_{cat}$ of 0.43 $sec^{-1}$ of dCK R104M/D133A implies that the presence of this enzyme in human cells will catalyze the conversion of BVdU to BVdU-monophosphate, thus allowing BVdU to exert a cytotoxic effect on the cells. To test the ability of the mutant dCK in reducing cell proliferation in the presence of BVdU, exemplary HERCEPTIN® (Genentech, South San Francisco, Calif.)—dCK R104M/D133A conjugate was delivered into a breast cancer-derived cell line SKBR-3. The cells were then exposed to varying amount of BVdU for 96 hours. The ability of the antibody-mutant dCK to phosphorylate BVdU was reflected by the reduced levels of cell viability compared with untreated control cells. Cell viability was measured using the MTS cytotoxicity assay according to the manufacturer's instructions (Promega). In short, the tetrazolium compound (3-(4,5-dimethylthiazol-2-yl)-5-(3-carboxymethoxyphenyl)-2-(4-sulfophenyl)-2H-tetrazolium, inner salt; MTS) was added to the cells. MTS was reduced by cellular dehydrogenase into formazan, which is soluble in tissue culture medium. Measuring formazan absorbance at a wavelength of 492 nm reflected levels of dehydrogenase enzyme activity found in metabolically-active cells. Since the production of formazan is proportional to the number of living cells, the intensity of the produced color is a good indication of the viability of the cells.

Figure 11:
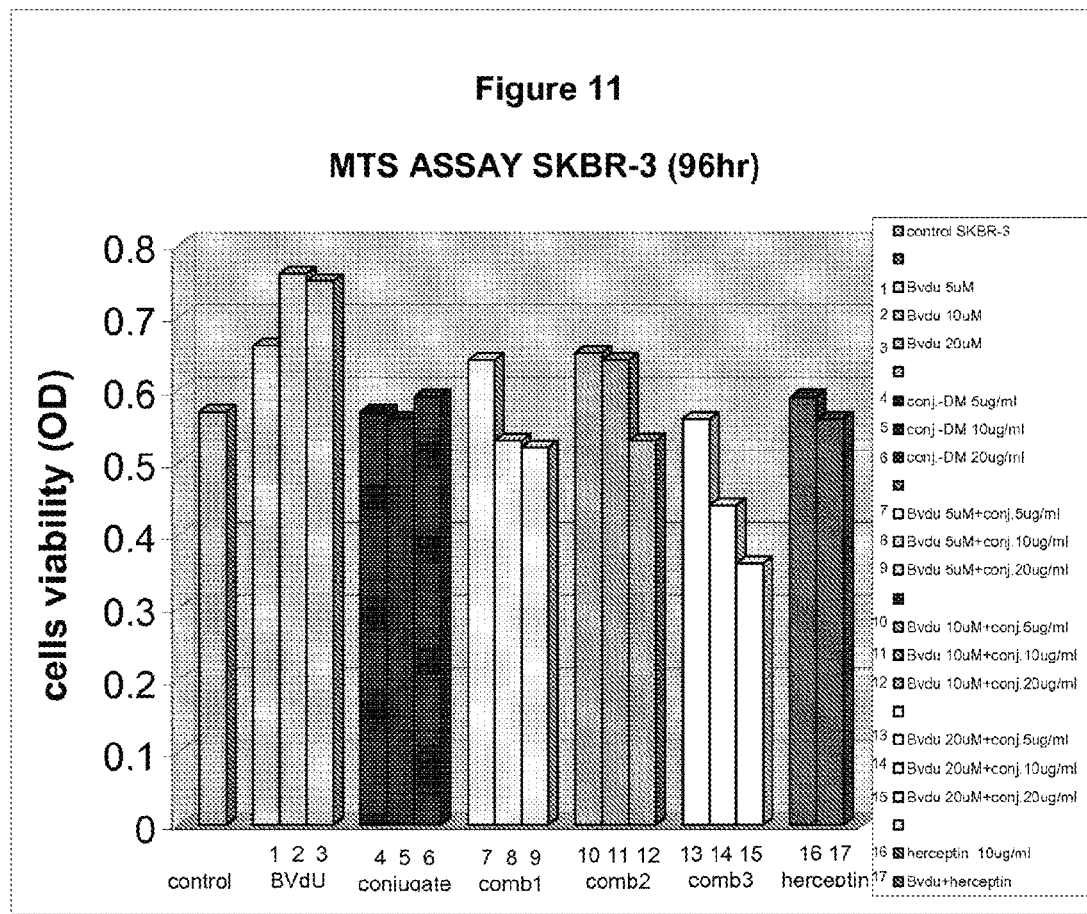
FIG. 11 depicts a bar graph showing the sensitivity of a breast cancer derived cell line (SKBR-3) to the treatment of BVdU alone, HERCEPTIN® and the dCK R104M/D133A (as referred to as "DM" in the figure) variant conjugate alone, or the combination of BVdU and the HERCEPTIN® dCK variant conjugate in a MTS cytotoxicity assay.

As shown in FIG. 11, cells treated with HERCEPTIN®-dCK R104M/D133A conjugate in conjunction with BVdU showed significantly reduced cell viability. HERCEPTIN® alone, or the HERCEPTIN®-dCK R104M/D133A conjugate alone without BVdU had no effect on cell viability. (FIG. 11, lane 16 and lanes 4-6) Similarly, BVdU alone had no detrimental effect on cell proliferation; in fact, cells seemed to grow faster in the presence of BVdU. (FIG. 11, lanes 1-3) BVdU in combination with HERCEPTIN®, without the mutant dCK R104M/D133A, had no effect on cell viability. (FIG. 11, lane 17) Thus, untreated cells were not sensitive to BVdU or HERCEPTIN®. However, the combination of the HERCEPTIN®-dCK R104M/D133A conjugate with BVdU resulted in decreased cell proliferation. (FIG. 11, lanes 7-15) The effect was most pronounced at the highest concentration of the HERCEPTIN®-dCK R104M/D133A conjugate and at the highest dose of BVdU (FIG. 11, lanes 13-15), where a decrease in cell proliferation by about 40% was observed. Thus, dCK R104M/D133A targeted and delivered to the cell by HERCEPTIN® was shown to convert BVdU into a toxic metabolite in human cells. Similar experiments can be conducted using an antibody-dCK conjugate with other amino acid substitutions as described herein.

Example 9

Modified Human dCK Mutant with R104Q/D133A Substitutions Exhibited Enhanced Catalytic Activities and Substrate Specificity for Thymidine Next, modified dCK with substitutions other than methionine at position 104 were tested for their ability to enable the enzyme to phosphorylate thymidine. In this experiment, dCK with R104Q/D133A substitutions was generated and tested. The results are shown in Table 6.

TABLE 6

Kinetic data comparing WT dCK and the R104Q-D133A dCK variant

| Nucleoside (200 uM) | $k_{cat}$ WT dCK ($sec^{-1}$) (with 1 mM ATP as donor) | $k_{cat}$ R104Q-D133A dCK ($sec^{-1}$) (with 1 mM ATP as donor) |
|---|---|---|
| Deoxycytidine | 0.03 | 0.06 |
| L-Deoxycytidine | 0.01 | 0.05 |

TABLE 6-continued

Kinetic data comparing WT dCK and the R104Q-D133A dCK variant

| Nucleoside (200 uM) | $k_{cat}$ WT dCK (sec$^{-1}$) (with 1 mM ATP as donor) | $k_{cat}$ R104Q-D133A dCK (sec$^{-1}$) (with 1 mM ATP as donor) |
|---|---|---|
| Deoxythymidine | ND | 0.15 |
| L-Deoxythymidine | ND | 0.24 |

ND—not detectable under the assay conditions used

As shown in Table 6, the rate of thymidine phosphorylation ($k_{cat}$) by wild-type dCK was hardly measurable. In contrast, the dCK variant R104Q/D133A phosphorylated thymidine efficiently. In fact, even the non-physiological L-deoxythymidine can be phosphorylated by this mutant. Note that the R104Q/D133A dCK variant phosphorylated more efficiently both the cytidine and thymidine substrates than the wild-type enzyme. In addition, the R104Q/D133A dCK variant phosphorylated thymidine substrates more efficiently than cytidine substrates.

Additional mutants were tested for the presence of thymidine kinase activity. The results are shown in Table 7. Among the mutant tested, R104M/D133A and R104L/D133A exhibited relatively high thymidine kinase activity, while R104I/D133A and R104Q/D133A exhibited comparatively low thymidine kinase activity. Both mutants can phosphorylate the D- and L-form of thymidine. It was observed that the residue at position 104 determined the specificity: with a methionine, the L-form was

TABLE 7

Kinetic characterization of dCK variants with mutations at positions 104 and 133 with respect to D-L-thymidine.

| Mutant | $^a k_{obs}$ D-dT | Rel $k_{obs}$ | $k_{obs}$ L-dT | Rel $k_{obs}$ |
|---|---|---|---|---|
| WT | 0.008 ± 0.001$^b$ | 1 | 0.017 ± 0.023 | 1 |
| R104M/D133A | 1.15 ± 0.01 | 144 | 1.95 ± 0.09 | 115 |
| R104L/D133A | 2.86 ± 0.09 | 358 | 1.07 ± 0.09 | 63 |
| R104I/D133A | 0.40 ± 0.01 | 50 | 0.19 ± 0.02 | 10 |
| R104Q/D133A | 0.10 ± 0.06 | 12.5 | 0.15 ± 0.02 | 9 |
| R104V/D133A | <0.005 | | <0.005 | |
| R104F/D133A | <0.005 | | <0.005 | |
| R104K/D133A | <0.005 | | <0.005 | |

$^a k_{obs}$ are in sec$^{-1}$ determined for a nucleoside concentration of 200 μM
$^b$ Standard deviation phosphorylated twice as fast as the D-form; conversely, with a leucine at position 104, the D-form was phosphorylated faster by more than 2-fold.

The R104I/D133A, R104Q/D133A, R104V/D133A, and R104F/D133A mutants exhibited detectable activities toward some of the nucleosides or nucleoside analogs when higher concentrations of the nucleosides were used. In a separate experiment, those mutant dCKs were analyzed in the presence of a nucleoside substrate at a concentration of 200 mM, and a phosphoryl donor ATP at a concentration of 1 μM. The results are summarized in Table 8.

TABLE 8

Kinetic analysis of modified human dCK containing selected mutations at positions 104 and 133.

| dCK Variant | | D-dC | D-dG | Gem | D-dT | L-dT | L-dU |
|---|---|---|---|---|---|---|---|
| WT (R104; D133) | | 0.03 | 0.94 | 0.39 | N.D. | N.D. | N.D. |
| R104 = | D133 = | | | | | | |
| Q | D | 0.07 | 0.06 | 0.06 | 0.05 | 0.06 | 0.06 |
| M | A | 1.84 | 0.18 | 2.29 | 1.15 | 1.95 | 1.77 |
| L | A | 0.27 | 0.3 | 2.04 | 2.86 | 1.07 | 2.56 |
| I | A | 0.06 | 0.08 | 0.21 | 0.4 | 0.19 | 0.4 |
| Q | A | 0.08 | 0.06 | 0.17 | 0.1 | 0.15 | 0.14 |
| V | A | 0.03 | 0.03 | N.D. | 0.04 | 0.05 | N.D. |
| F | A | 0.02 | 0.02 | N.D. | 0.02 | 0.02 | N.D. |

N.D.: not detectable under the assay conditions used.

As shown in Table 8, the R104M/D133A dCK mutant phosphorylated gemcitabine at a rate of 2.29 sec$^{-1}$, an increase from the rate of 0.39 sec$^{-1}$ of the wild-type enzyme. Additionally, while the wild type enzyme showed no detectable activity with thymidine or thymidine analog, the R104M/D133A mutant dCK acquired the ability to phosphorylate thymidine: specifically, the R104M/D133A dCK phosphorylated D-thymidine (D-dT) at a rate of 1.15 sec$^{-1}$, L-thymidine (L-dT) at a rate of 1.95 sec$^{-1}$, and L-deoxyuridine (L-dU) at a rate of 1.77 sec$^{-1}$.

Additionally, in the background of the D133A substitution, modified human dCKs with other substitutions at position 104, such as a leucine, isoleucine, or glutamine substitution, not only showed higher activities for deoxycytidine than the wild type dCK, but also exhibited thymidine kinase activity that is absent in wild type dCK. The R104L/D133A dCK mutant showed particular clinical importance since it exhibited differential activity for dT than dC as compared to dCK R104M/D133A. A modified dCK with high thymidine kinase activities allows efficient phosphorylation of a clinically important thymidine analog such as BVdU, whereas the lower activities for the natural substrate dC minimize the perturbation of the nucleotide pool in the cell. Thus, a modified dCK with high selectively high activity for dT, such as dCK R104L/D133A, is a particularly desirable enzyme for clinical purposes because it phosphorylates BVdU with fewer toxic side effects.

In conclusion, the data show that a methionine, a leucine, and to a lesser extent, a glutamine, or an isoleucine substitution at position 104 endowed dCK with thymidine kinase activity. In summary, the results demonstrated that several combinations of substitutions at positions 104 and 133 of human dCK generate mutants with improved and desirable activities. Such dCK mutants could play a role in the specific activation of nucleoside analogs to combat various diseases such as viral infection and cancers.

Example 10

Kinetic Characterization of R104M/D133A and R104L/D133A

The above-described experiments identified the dCK mutants R104M/D133A and R104L/D133A as the most active ones among the mutants tested. The kinetics of these two dCK variants were analyzed with respect to the physiological substrates of dCK (dC, dA, dG), the nucleoside analogs AraC and gemcitabine, and both enantiomeric forms of thymidine. The results are shown in Table 9.

TABLE 9

Comparison of catalytic efficiencies of new mutants with wild type dCK

| | Wild-type | | | R104M/D133A | | | R104L/D133A | | |
|---|---|---|---|---|---|---|---|---|---|
| Substrate | $k_{cat}$ (sec$^{-1}$) | $K_m$ (μM) | $k_{cat}/K_m$ (×10$^{-3}$) | $k_{cat}$ (sec$^{-1}$) | $K_m$ (μM) | $k_{cat}/K_m$ (×10$^{-3}$) | $k_{cat}$ (sec$^{-1}$) | $K_m$ (μM) | $k_{cat}/K_m$ (×10$^{-3}$) |
| D-dC | 0.04 ± 0.01[a] | <3 | >13.3 | 1.80 ± 0.04 | 5.70 ± 0.44 | 315.8 | 0.25 ± 0.14 | 8.0 ± 1.0 | 31.3 |
| D-dA | 2.13 ± 0.35 | 114.6 ± 3.5 | 18.6 | 4.51 ± 0.33 | 1040 ± 117 | 4.3 | 5.72 ± 0.21 | 162.3 ± 20.1 | 35.2 |
| D-dG | 2.60 ± 0.10 | 231.0 ± 20.0 | 11.3 | 1.73 ± 0.12 | 1865 ± 211 | 0.9 | 3.66 ± 0.01 | 2266 ± 823 | 1.6 |
| AraC | 0.34 ± 0.01 | 13.1 ± 1.1 | 26.0 | 1.43 ± 0.03 | 136.5 ± 10.0 | 10.5 | 0.79 ± 0.03 | 50.6 ± 6.1 | 15.6 |
| Gem | 0.39 ± 0.03 | 16.1 ± 3.5 | 24.2 | 2.68 ± 0.07 | 56.2 ± 16.8 | 47.7 | 2.01 ± 0.08 | 33.8 ± 5.3 | 59.5 |
| D-dT | NA | NA | — | 1.74 ± 0.01 | 144.0 ± 10.1 | 12.1 | 3.20 ± 0.07 | 24.3 ± 3.6 | 131.7 |
| L-dT | NA | NA | — | 3.13 ± 0.10 | 138.0 ± 10.1 | 22.7 | 1.33 ± 0.01 | 17.8 ± 1.6 | 74.7 |

[a] standard error
NA: not applicable, due to the very high Km (>3 mM)

As shown in Table 9, the mutant R104M/D133A showed the highest efficiency ($k_{cat}/K_m$) when D-dC was used as a substrate; while the $K_m$ for dC was slightly increased in the mutant, it was offset by a dramatic 45-fold increase in $k_{cat}$. The specificity of R104M/D133A to dC was a result of the much-increased $K_m$ values for both dA and dG (8 to 10-fold larger than the $K_m$ of wild type dCK for the same substrates). In contrast, while the $K_m$ of the R104L/D133A mutant for dG was also dramatically increased as compared to the wild-type, the R104L/D133A mutant's $K_m$ for dA is comparable to wild type dCK.

The enhancement in phosphorylation efficiency ($k_{cat}/K_m$) for gemcitabine by R104M/D133A and R104L/D133A, a 2- and 2.5-fold increase, respectively, was due to a significant improvement in $k_{cat}$, whereas $K_m$ countered this by a moderate increase. Interestingly, the efficiency of AraC phosphorylation by either mutant is less than that of wild type dCK. This suggested that the phosphorylation efficiency of nucleoside analogs by R104M/D133A and R104L/D133A was affected by the substituents at the 2'-position of the sugar ring.

Most interesting was the endowment of R104M/D133A and R104L/D133A with thymidine kinase activity. The $K_m$ for D-dT was reduced from over 3 mM with wild type dCK (Iyidogan, et al., 2008, Biochemistry 47:4711-4720) to less than 150 μM with R104M/D133A and below 25 μM with R104L/D133A. The R104L/D133A variant also had a lower $K_m$ value for the L-form of thymidine than R104M/D133A, and it is primarily this fact that makes this double mutant the most efficient dCK variant for thymidine kinase activity. As a methionine is one atom longer than a leucine, it is possible that this residue is still too long to optimally accommodate the C5-methyl group of the thymine base. However, due to methionine being a non-branched amino acid, thymine can still bind with a reasonable $K_m$ value (as measured for R104M/D133A). The mutant with a glutamine variant at position 104, R104Q/D133A, demonstrated much lower activity than R104L/D133A. Glutamine, apart from being a polar residue, has the same length as a methionine but is branched at the delta-position. This branching is the likely cause for R104Q/D133A having lower thymidine kinase activity. The additional structural data of R104M/D133A with L-dT (see below) aided this analysis, as the electron density for the tip of the methionine side chain was weak, which was consistent with high mobility/disorder caused by proximity of the C5-methyl group of L-dT.

Example 11 dCK with S74E Substitution Exhibits Enhanced Activity in Phosphorylating Thymidine Analog It was reported that dCK undergoes post-translational phosphorylation on Ser74 that increases its activity (Smal et al., 2006, Nucleosides Nucleotides Nucleic Acids 25, 1141-1146). Using the dCK S74E mutant to mimic this phosphorylated state, it was shown that this modification increased the rate of phosphorylation of dC by 11-fold, but had no effects on dA, dG, AraC or gemcitabine phosphorylation (McSorley et al., 2008, FEBS Lett 582:720-724). The mechanism behind the selective rate enhancement of the S74E mutant is unclear, as the serine is a part of the region called the insert, which is not observed in most crystal structures of dCK. As shown above, the R104M/D133A variant also selectively increased the rate of dC phosphorylation. A dCK mutant with the combination of the mutations of R104M, D133A and S74E resulted in a further increase in the rate of dC phosphorylation to ~5 sec$^{-1}$ as compared with the rate of wild-type 0.03 sec$^{-1}$, R104M/D133A 1.84 sec$^{-1}$ and R104L/D133A 0.27 (see Table 8). This suggested that the S74E mutant provides synergistic effects on the enzymatic activity of the modified dCK via mechanisms that are distinct from those for the R104M/D133A and R104L/D133A mutants.

Further, the effects on thymidine phosphorylation of a dCK variant with a serine substitution at amino acid position 74 in the background of dCK mutants described above were analyzed. Wild type dCK with a single S74E substitution did not phosphorylate thymidine or thymidine analogs; however, S74E in the background of R104M/D133A double or A100V/R104M/D133A triple mutation rendered the modified dCK a more efficient thymidine kinase than either of the parent modified dCK enzymes. The kinetics of the modified dCK with a further S74E substitution was analyzed based on the method described above using the S74E/R104M/D133A mutant dCK as an example. In this experiment, the rate of phosphorylation of the thymidine analog BVdU by the dCK S74E/R104M/D133A mutant was 1.2 sec$^{-1}$, three times better than that of dCK R104M/D133A without the S74E substitution (0.43 sec$^{-1}$).

Figure 12:
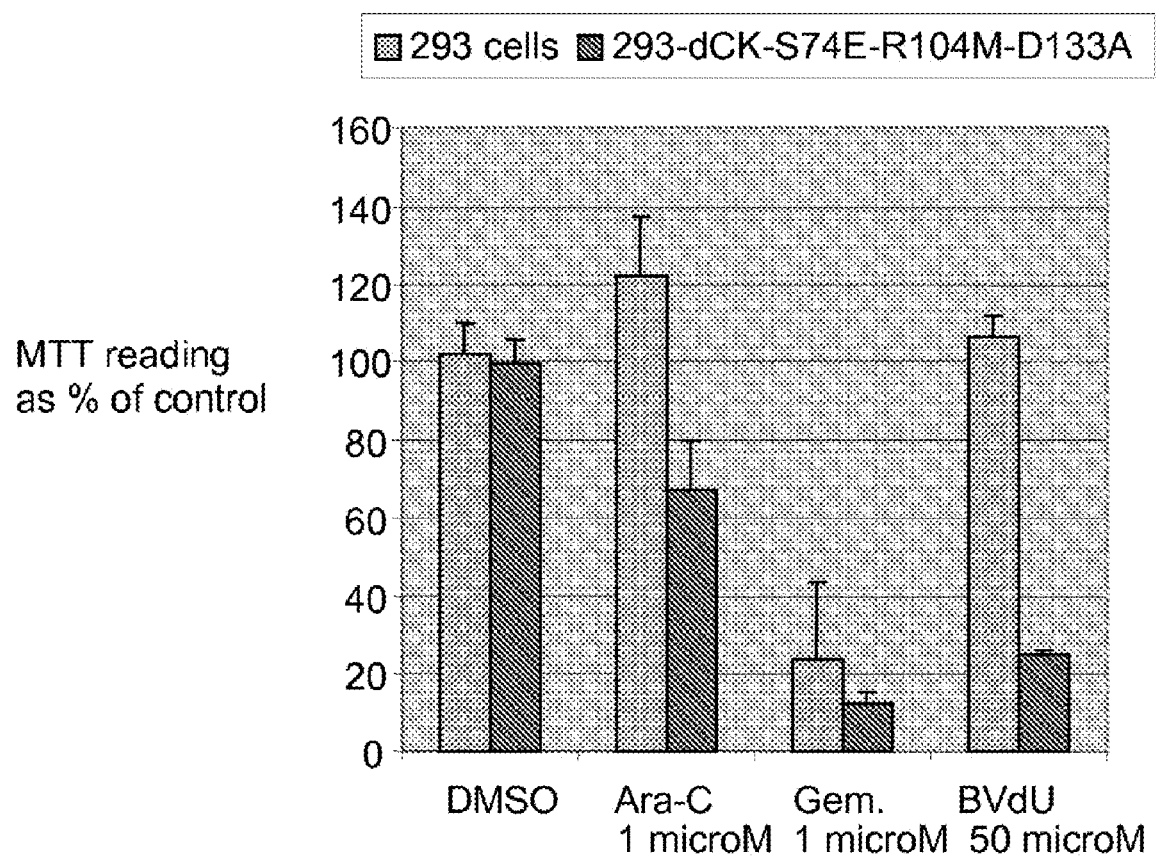
FIG. 12 depicts a graph showing the effect of dCK-S74E/R104M/D133A on cell growth in the presence of AraC, gemcitabine or BVdU.

Next, whether the dCK-S74E/R104M/D133A variant could inhibit cell growth in the presence of NAs including BVdU was tested. Human 293 cells were stably transfected with a recombinant expression construct encoding the dCK-S74E/R104M/D133A protein. The proliferative capacity of the stably transfected cell line was compared to the parental 293 cells after treating the cells with several nucleoside analogs such as AraC, gemcitabine, and BVdU. Since some of the nucleosides were first dissolved in the solvent DMSO, equal amounts of DMSO were used as control. As shown in FIG. 12, DMSO had no effect on proliferation of either the parent 293 cell line, or the 293 dCK variant cell line.

When tested using nucleoside analogs such as AraC and gemcitabine, approved prodrugs for the treatment of several types of cancers, AraC was found to have no inhibitory effect on proliferation of 293 cells at a concentration of 1 µM. In contrast, AraC at the same concentration inhibited the growth of 293 cells expressing the dCK S74E/R104M/D133A variant (FIG. 12). Gemcitabine at 1 µM inhibited growth of the parent 293 cell line by 75%, and further inhibited the growth of 293 cell line expressing the mutant dCK by about 90%. These results showed that expression of the dCK S74E/R104M/D133A variant in cells enhanced the anti-proliferative effect of AraC and gemcitabine.

The thymidine analog BVdU ((E)-5-(2-bromovinyl)-2'-deoxyuridine), an approved anti-viral drug in Germany, is efficiently phosphorylated by viral thymidine kinase, but is very poorly phosphorylated, if at all, by human enzymes. When tested as described above for AraC, the human dCK variant S74E/R104M/D133A efficiently phosphorylated BVdU, and activated BVdU selectively killed cells expressing this dCK mutant. As shown in FIG. 12, BVdU, even at the highest tested concentration of 50 µM, did not inhibit the growth of parent 293 cells; however, BVdU dramatically inhibited the growth of 293 cells expressing the mutant dCK. In other words, BVdU was only toxic to cells that expressed the mutant dCK. These results showed that the dCK S74E/R104M/D133A mutant sensitized cells to BVdU and selectively killed cells that expressed, by transfection or targeted delivery, the dCK S74E/R104M/D133A mutant. Similarly, 293 cells stably expressing S74E/R104M/D133A-dCK were also sensitive to L-dT or L-dU mediated cell killing (data not shown).

Example 12

Structural Analysis of the R104M/D133A Mutant in Complex with L-dT and ADP

To understand how the R104M/D133A and R104L/D133A mutations improved dCK activities, crystal structure of R104M/D133A mutant in complex with ADP at the phosphoryl donor site and the L-form of thymidine at the nucleoside acceptor site was solved with a 2.3 Å resolution. Data collection and refinement statistics are presented in Table 10.

TABLE 10

Data collection and refinement statistics

| | |
|---|---|
| PDB ID | 3EXK |
| Beamline | SERCAT BM-22 |
| Wavelength (Å) | 1.0 |
| Temperature (K) | 100 |
| Resolution Range (Å) | 30.0-2.3 |
| Reflections | |
| Observed | 93997 |
| Unique | 13710 |
| Completeness (%) | 99.3 (98.7)[a] |
| $R_{sym}$(%) | 8.9 (29.8) |
| I/σ(I) | 14.42 (6.93) |
| Space group | P4₃2₁2 |
| Unit cell (Å) | |
| a, b | 79.78 |
| c | 93.70 |
| Molecules per a.u. | 1 |
| Refinement statistics | |
| $R_{cryst}$ (%) | 21.7 |
| $R_{free}$ (%) | 27.8 |
| Number of atoms | |
| Protein | 1838 |
| Nucleoside | 17 |
| ADP | 27 |
| Water | 63 |
| R.m.s. deviation | |
| Bond length (Å) | 0.013 |

TABLE 10-continued

Data collection and refinement statistics

| | |
|---|---|
| Bond angles (°) | 1.437 |
| Average B-factors (Å²) | |
| Protein | 45.0 |
| Main chain | 44.5 |
| Side chain | 45.4 |
| ADP | 35.5 |
| Nucleoside | 35.5 |
| Waters | 47.4 |

[a]values for the highest resolution shell is in parenthesis

Figure 13:
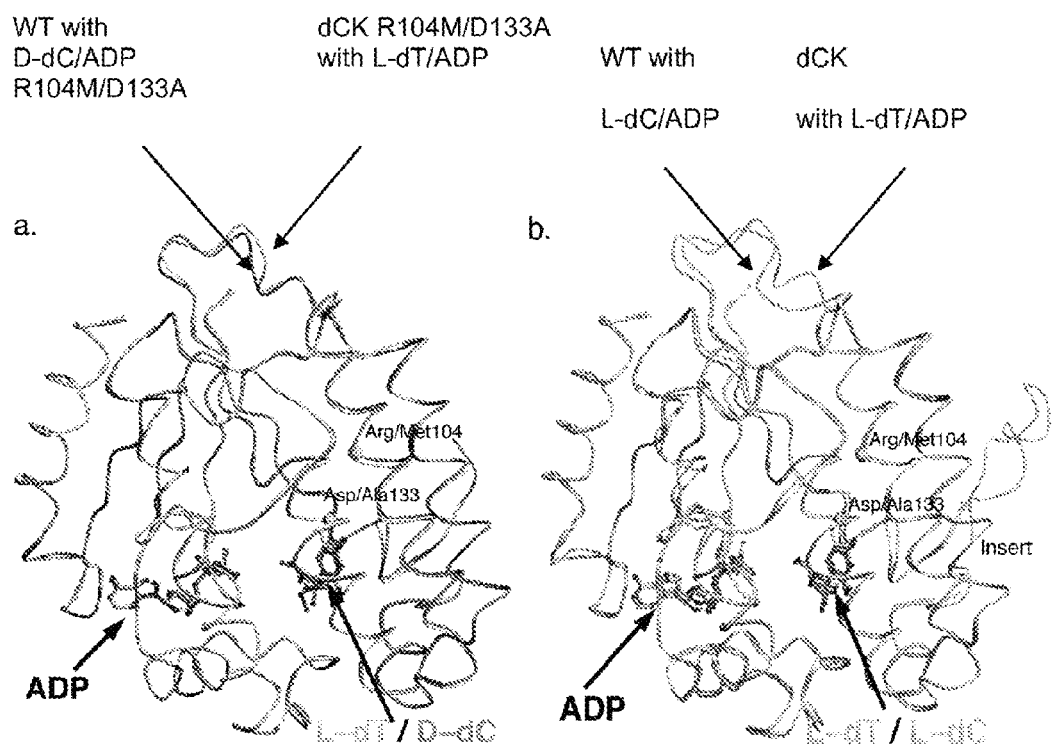
FIG. 13 shows superposition of structure of dCK R104M/D133A in complex with L-dT and ADP with (a) wild-type dCK in complex with D-dC and ADP or (b) wild-type dCK in complex with L-dC and ADP. The location of the mutations is marked by a sphere.

As expected, the dual mutations did not change the overall structure of the enzyme. The Root Mean Square Deviation (RMSD) for these data between R104M/D133A in complex with L-dT+ADP and wild-type dCK in complex with D-dC+ADP is 0.40 Å on 226 atoms (FIG. 13a), and with wild-type dCK in complex with L-dC+ADP is 0.64 Å on 226 atoms (FIG. 13b). The R104M/D133A mutant largely maintained the overall structure of the wild type protein. The local structure of regions proximal to positions 104 and 133 were also nearly identical with that in wild type dCK. The few notable differences between the structures could be accounted by crystal contacts, and were not attributed to the mutations.

Figure 14:
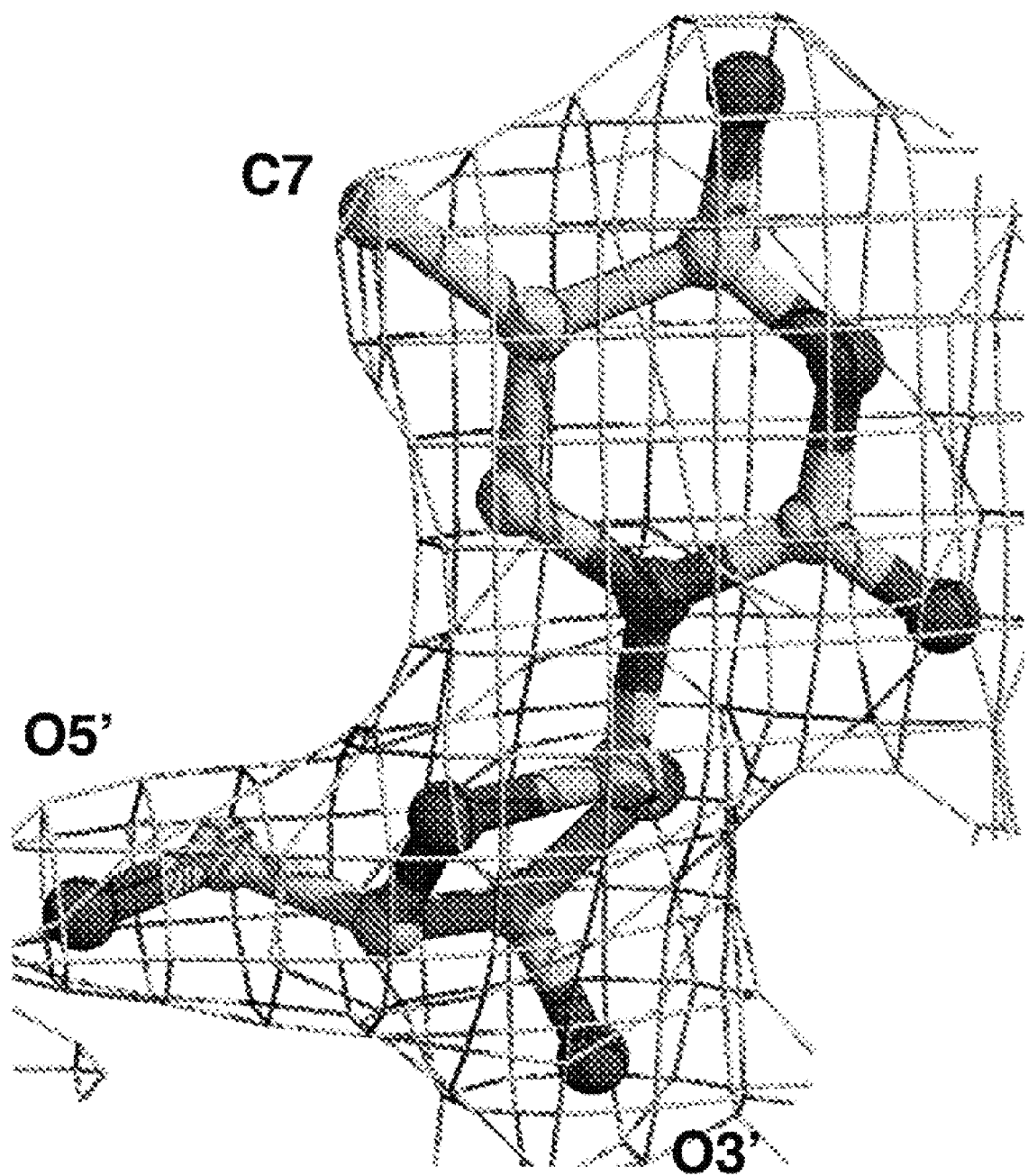
FIG. 14 shows the 2Fo-Fc electron density map for L-dT, contoured at the 1.5 sigma level.
Figure 15:
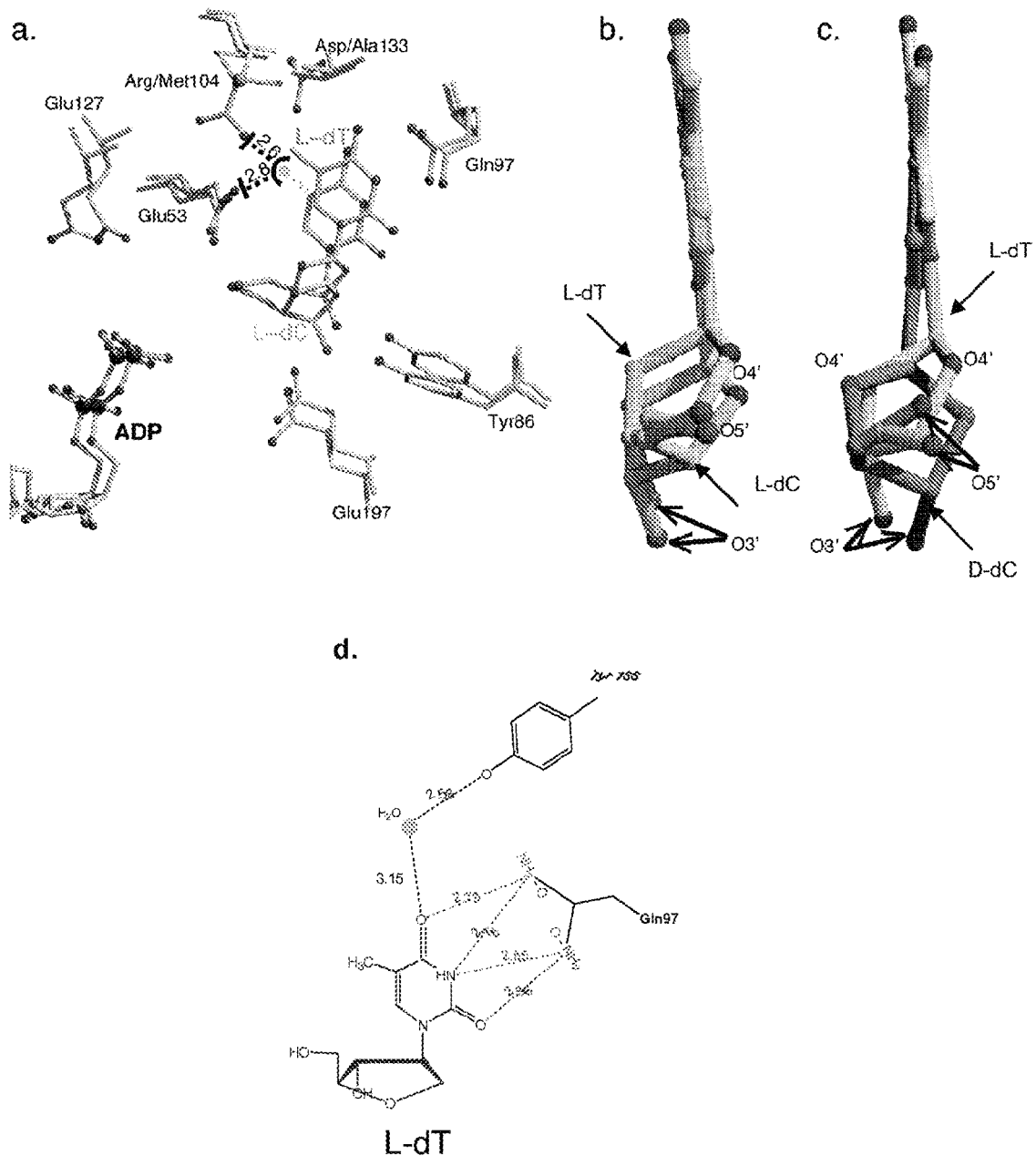
FIG. 15a shows the active site residues of dCK R104M/D133A mutant complexed with L-dT/ADP complex overlaid with those of WT-dCK complexed with L-dC/ADP. The dashed line and sphere schematically imitated the thymine base 5-methyl group in the position taken up by L-dC: in wild-type dCK, this methyl group would be 2.8 Å away from Glu53, and 2.6 Å from Arg104. The mutation at position 104 from arginine to methionine permits L-dT to position itself deeper into the active site, avoiding the steric clash with Glu53.
FIG. 15b represents a ~90 degrees rotated view relative to the orientation in (a) focusing on the nucleoside showing that the base of L-dT is parallel to that of L-dC.
FIG. 15c represents the analogous view of the overlay of L-dT structure on the D-dC structure indicating that the base in L-dT is tilted relative to the base orientation of D-dC, which is a consistent feature of dCK upon binding nucleosides of the L-chirality.
FIG. 15d shows two alternate sets of possible hydrogen bonds between the thymine base and the side chain of Gln97.

The electron density maps for the nucleotide ADP and the nucleoside L-dT is shown in FIG. 14. The thymine base was bound in the anti-conformation, thereby conserving the orientation seen with the dC (Sabin et al., 2003, Nat. Struct. Biol. 10:513-519). However, overlay of the R104M/D133A complex with that of wild type dCK with either the L-form or D-form of dC revealed a surprising result: L-dT bound significantly deeper in the nucleoside binding site of dCK R104M/D133A (FIG. 15). Presumably, the space generated by substituting the arginine side chain by the shorter methionine allowed the nucleoside to penetrate deeper into the pocket. Concomitantly, the ADP molecule shifted in the same direction, and hence the change of position of Glu127. FIG. 15a shows the superposition of the R104M/D133A complex with L-dT and the wild-type dCK complex with L-dC. The side chains of active site residues adjusted their position to preserve the same interactions with L-dT as seen with dC. For example, Tyr86 and Glu197 tracked the shift of the nucleoside and maintained their interactions with the sugar's 3'-hydroxyl group.

The side chain of Gln97 also adjusted somewhat to the deeper orientation of L-dT versus that seen with L-dC. However, the definitive orientation of the side chain of Gln97, that acted both as hydrogen bond donor and acceptor, could not be ascertained by the x-ray data at the resolution of the structure. In the complex with L-dC the Gln97 orientation was unambiguous: based on distance considerations, the side chain carbonyl group interacted with the amino moiety of the base, and the amino group with N3 of the base. In cytosine, N3 is deprotonated, allowing it to accept a hydrogen-bond donor from the Gln97 amino group. In contrast, in the complex with L-dT, the situation was vague, as both orientations—interchanged by rotating the tip of the side chain by 180 degrees—make chemical sense (FIG. 15d). In one orientation, identical to that adopted with L-dC, the carbonyl group of the side chain would interact with N3; (this was a productive interaction as the thymine N3 was protonated) and the amino group with the carbonyl group at position 2. The alternative orientation, the one depicted in FIG. 15a, also had the carbonyl group of the Gln97 side chain interacting with N3, but now the amino group interacted with the carbonyl group at position 4 (FIG. 15d).

The deeper position of L-dT in the nucleoside-binding site of R104M/D133A relative to that of L-dC in wild type dCK explained why thymidine was a very poor substrate of wild type dCK. If L-dT would bind in the same position as L-dC, its C5 methyl group (dashed line and ball, FIG. 15a) would clash with the side chains of Glu53 (2.8 Å) and Arg104 (2.6 Å). The replacement of Arg104 by a methionine created the space into which, following the shift of the L-dT molecule deeper into the active site, the C5 methyl group of thymidine could fit and avoid a steric clash with Glu53. Importantly, the new position adopted by L-dT still allowed the 5'-hydroxyl group to maintain a nearly identical position as seen for L-dC. This is critical, since phosphoryl transfer occurred to this hydroxyl group.

The capability of human dCK to phosphorylate L-nucleosides is directly related to the active site architecture that permits binding mode flexibility. Previous studies have shown that residues flanking the sugar moiety accommodated both enantiomers in the active site, albeit the base moiety must undergo a tilt. The base moiety of L-nucleosides tilted by ~10 degrees relative to the position of their D-counterpart; however, the interactions with the base were preserved. Regardless of the enantiomeric form, the sugar 5'-hydroxyl group maintained close proximity to Glu53, the residue that functioned as the catalytic base. In the R104M/D133A complex with L-dT, while the nucleoside bound deeper into the binding site, L-dT (the structure on the top as indicated in FIG. 15b) retained the same tilt as seen for L-dC (the structure on the bottom as indicated in FIG. 15b) when bound to wild type dCK. The base tilting of L-dT is apparent when compared to D-dC (the structure on the bottom as indicated in FIG. 15c) bound to wild type dCK. This suggests that base tilting of L-nucleosides was a consequence of the sugar's position in the active site—without this tilting the sugar would clash with Leu82. The results showed that even when the nucleoside bound deeper into the nucleoside-binding site, the same restraints on the sugar position necessitated the base to tilt relative to its position in D-nucleosides.

It should be understood that the foregoing disclosure emphasizes certain specific embodiments of the invention and that all modifications or alternatives equivalent thereto are within the spirit and scope of the invention as set forth in the appended claims.

What is claimed is:

1. A modified human deoxycytidine kinase having amino acid substitutions at amino acid positions 104 and 133, optionally and in addition at amino acid position 74, and optionally and in addition at amino acid position 100, wherein the substitution at amino acid position 104 is glutamine, leucine, or isoleucine, and the substitution at amino acid position 133 is alanine, and wherein the amino acids are identified according to the numbering of wild type human deoxycytidine kinase identified by SEQ ID NO:1.

2. The modified human deoxycytidine kinase of claim 1, wherein the modified human deoxycytidine kinase has the amino acid sequence identified by SEQ ID NO:8, SEQ ID NO:10 or SEQ ID NO:12.

3. The modified human deoxycytidine kinase of claim 1, wherein the substitution at amino acid position 104 is leucine and the substitution at amino acid position 133 is alanine.

4. The modified human deoxycytidine kinase of claim 3, wherein the modified human deoxycytidine kinase has the amino acid sequence identified by SEQ ID NO:10.

5. The modified human deoxycytidine kinase of claim 1, further comprising a substitution at amino acid position 100.

6. The modified human deoxycytidine kinase of claim 5 wherein the substitution at amino acid position 100 is valine.

7. The modified human deoxycytidine kinase of claim 6, wherein the modified human deoxycytidine kinase has the amino acid sequence identified by SEQ ID NO:7, SEQ ID NO:9 or SEQ ID NO:11.

8. The modified human deoxycytidine kinase of claim 6 wherein the substitution at amino acid position 104 is leucine.

9. The modified human deoxycytidine kinase of claim 8, wherein the modified human deoxycytidine kinase has the amino acid sequence identified by SEQ ID NO:9.

10. The modified human deoxycytidine kinase of claim 1, further comprising a substitution at amino acid position 74, wherein the substitution at amino acid position 74 is glutamic acid.

11. The modified human deoxycytidine kinase of claim 10 wherein the modified human deoxycytidine kinase has the amino acid sequence identified by SEQ ID NO:14, SEQ ID NO:16 or SEQ ID NO:18.

12. The modified human deoxycytidine kinase of claim 10 wherein the substitution at amino acid position 104 is leucine.

13. The modified human deoxycytidine kinase of claim 12, wherein the modified human deoxycytidine kinase has the amino acid sequence identified by SEQ ID NO:16.

14. The modified human deoxycytidine kinase of claim 10, further comprising a substitution at amino acid position 100, wherein the substitution at amino acid 100 is valine.

15. The modified human deoxycytidine kinase of claim 14 wherein the modified human deoxycytidine kinase has the amino acid sequence identified by SEQ ID NO:13, SEQ ID NO:15 or SEQ ID NO:17.

16. The modified human deoxycytidine kinase of claim 14 wherein the substitution at amino acid position 104 is leucine.

17. The modified human deoxycytidine kinase of claim 16, wherein the modified human deoxycytidine kinase has the amino acid sequence identified by SEQ ID NO:15.

18. The modified human deoxycytidine kinase of claim 1, wherein said modified human deoxycytidine kinase phosphorylates a D-type or L-type thymidine analog.

19. The modified human deoxycytidine kinase of claim 18, wherein the thymidine analog is (E)-5-(2-bromovinyl)-2'-deoxyuridine (BVdU).

20. A modified human deoxycytidine kinase having amino acid substitutions at amino acid positions 74, 104 and 133, and optionally and in addition at amino acid position 100, wherein the substitution at amino acid position 74 is glutamic acid, the substitution at amino acid position 104 is methionine, and the substitution at amino acid position 133 is alanine, and wherein the amino acids are identified according to the numbering of wild type human deoxycytidine kinase identified by SEQ ID NO:1.

21. The modified human deoxycytidine kinase of claim 20, wherein the modified human deoxycytidine kinase has the amino acid sequence identified by SEQ ID NO:20.

22. The modified human deoxycytidine kinase of claim 20, further comprising a substitution at amino acid position 100, wherein the substitution at amino acid position 100 is valine.

23. The modified human deoxycytidine kinase of claim 22, wherein the modified human deoxycytidine kinase has an amino acid sequence identified by SEQ ID NO:19.

24. The modified human deoxycytidine kinase of claim 20, wherein said modified human deoxycytidine kinase phosphorylates a D-type or L-type thymidine analog.

25. The modified human deoxycytidine kinase of claim 24, wherein the thymidine analog is (E)-5-(2-bromovinyl)-2'-deoxyuridine (BVdU).

26. A conjugate comprising an antibody and a modified human deoxycytidine kinase of claim 1, wherein the antibody recognizes a cell surface antigen.

27. The conjugate of claim 26 wherein the antibody is Trastuzumab or HuM195.

28. The conjugate of claim 26 wherein the modified human deoxycytidine kinase has the sequence identified by SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18.

29. The conjugate of claim 28, wherein the modified human deoxycytidine kinase has the sequence identified by SEQ ID NO:15 or SEQ ID NO:16.

30. A pharmaceutical composition comprising the conjugate of claim 26, and a pharmaceutically acceptable carrier.

31. A kit for inhibiting or reducing proliferation of tumor cells comprising the conjugate of claim 26 in at least one container.

32. The kit of claim 31 further comprising a prodrug.

33. The kit of claim 32, wherein the prodrug is a D-type or L-type thymidine analog.

34. The kit of claim 33 wherein the thymidine analog is (E)-5-(2-bromovinyl)-2'-deoxyuridine (BVdU).

35. A conjugate comprising an antibody and a modified human deoxycytidine kinase of claim 20, wherein the antibody recognizes a cell surface antigen.

36. The conjugate of claim 35 wherein the antibody is Trastuzumab or HuM195.

37. The conjugate of claim 35 wherein the modified human deoxycytidine kinase has the sequence identified by SEQ ID NO:19 or SEQ ID NO:20.

38. The conjugate of claim 37, wherein the modified human deoxycytidine kinase has the sequence identified by SEQ ID NO:20.

39. A pharmaceutical composition comprising the conjugate of claim 35, and a pharmaceutically acceptable carrier.

40. A kit for inhibiting or reducing proliferation of tumor cells comprising the conjugate of claim 35 and at least one container.

41. The kit of claim 40 further comprising a prodrug.

42. The kit of claim 41, wherein the prodrug is a D-type or L-type thymidine analog.

43. The kit of claim 42 wherein the thymidine analog is (E)-5-(2-bromovinyl)-2'-deoxyuridine (BVdU).

44. An isolated polynucleotide comprising a nucleotide sequence encoding the modified human deoxycytidine kinase of claim 1.

45. The isolated polynucleotide of claim 44 wherein the modified human deoxycytidine kinase has the amino acid sequence identified by SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18.

46. An expression vector comprising the isolated polynucleotide of claim 44 wherein the expression vector is capable of expressing the modified human deoxycytidine kinase.

47. A host cell comprising the expression vector of claim 46.

48. A method for producing a modified human deoxycytidine kinase polypeptide comprising steps of:
 a. culturing the host cell of claim 47 under conditions effective to allow expression of the modified human deoxycytidine kinase polypeptide; and
 b. recovering the modified human deoxycytidine kinase polypeptide from the cell culture.

49. An isolated polynucleotide comprising a nucleotide sequence encoding the modified human deoxycytidine kinase of claim 20.

50. The isolated polynucleotide of claim 49 wherein the modified human deoxycytidine kinase has the amino acid sequence identified by SEQ ID NO:19 or SEQ ID NO:20.

51. An expression vector comprising the isolated polynucleotide of claim 49 wherein the expression vector is capable of expressing the modified human deoxycytidine kinase.

52. A host cell comprising the expression vector of claim 51.

53. A method for producing a modified human deoxycytidine kinase polypeptide comprising steps of:
 a. culturing the host cell of claim 52 under conditions effective to allow the expression of the modified human deoxycytidine kinase polypeptide; and
 b. recovering the modified human deoxycytidine kinase polypeptide from the cell culture.

54. A method of reducing or inhibiting proliferating of a tumor cell, comprising the step of contacting the tumor cell with a prodrug and the conjugate of claim 26, wherein the conjugate comprises an antibody and a modified human deoxycytidine kinase that converts the prodrug to a therapeutically active drug.

55. The method of claim 54, wherein the antibody is Trastuzumab or HuM195.

56. The method of claim 54, wherein the prodrug is a D-type or L-type thymidine analog.

57. The method of claim 56, wherein the thymidine analog is (E)-5-(2-bromovinyl)-2'-deoxyuridine (BVdU).

58. The method of claims 54, wherein the modified human deoxycytidine kinase has the amino acid sequence identified by SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18.

59. The method of claim 58 wherein the modified human deoxycytidine kinase has an amino acid sequence identified by SEQ ID NO:15.

60. The method of claim 54 wherein the tumor cell is a breast tumor cell or a leukemia cell.

61. A method of reducing or inhibiting proliferating of a tumor cell, comprising a step of contacting the tumor cell with a prodrug and the conjugate of claim 35, wherein the conjugate comprises an antibody and a modified human deoxycytidine kinase that converts the prodrug to a therapeutically active drug.

62. The method of claim 61, wherein the antibody is Trastuzumab or HuM195.

63. The method of claim 61, wherein the prodrug is a D-type or L-type thymidine analog.

64. The method of claim 63, wherein the thymidine analog is (E)-5-(2-bromovinyl)-2'-deoxyuridine (BVdU).

65. The method of claims 61, wherein the modified human deoxycytidine kinase has the amino acid sequence identified by SEQ ID NO:19 or SEQ ID NO:20.

66. The method of claim 65 wherein the modified human deoxycytidine kinase has the amino acid sequence identified by SEQ ID NO:20.

67. The method of claim 61 wherein the tumor cell is a breast tumor cell or a leukemia cell.

* * * * *